US011304769B2

(12) United States Patent
Cooper et al.

(10) Patent No.: US 11,304,769 B2
(45) Date of Patent: *Apr. 19, 2022

(54) SIDE LOOKING MINIMALLY INVASIVE SURGERY INSTRUMENT ASSEMBLY

(71) Applicant: INTUITIVE SURGICAL OPERATIONS, INC., Sunnyvale, CA (US)

(72) Inventors: Thomas G. Cooper, Menlo Park, CA (US); David J. Rosa, Sunnyvale, CA (US); Matthew R. Williams, Walnut Creek, CA (US); Eugene F. Duval, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 16/567,276

(22) Filed: Sep. 11, 2019

(65) Prior Publication Data
US 2020/0000317 A1    Jan. 2, 2020

Related U.S. Application Data

(60) Continuation of application No. 14/943,216, filed on Nov. 17, 2015, now Pat. No. 10,448,813, which is a
(Continued)

(51) Int. Cl.
*A61B 34/00*    (2016.01)
*A61B 1/00*    (2006.01)
(Continued)

(52) U.S. Cl.
CPC .............. *A61B 34/70* (2016.02); *A61B 1/002* (2013.01); *A61B 1/0016* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 3,557,780 A * 1/1971 Sato ..................... A61B 1/0055
600/141
4,401,123 A * 8/1983 Baba ........................ A61B 8/12
600/462
(Continued)

FOREIGN PATENT DOCUMENTS

JP    S57190549 A    11/1982
JP    S6483238 A    3/1989
JP    2000166936 A    6/2000

OTHER PUBLICATIONS

Advisory Action dated Oct. 21, 2010 for U.S. Appl. No. 11/762,132, filed Jun. 13, 2007.
(Continued)

*Primary Examiner* — Ryan N Henderson
(74) *Attorney, Agent, or Firm* — Artegis Law Group, LLP

(57) ABSTRACT

A surgical instrument is inserted through a guide tube. The surgical instrument exits at an intermediate position of the guide tube and is oriented to be substantially parallel to the guide tube's longitudinal axis as it exits. A stereoscopic image capture component is on the guide tube between the intermediate position and the guide tube's distal end. The image capture component's field of view is generally perpendicular to the guide tube's longitudinal axis. The guide tube is jointed to allow the image capture component to be moved. The surgical instruments and the guide tube are telemanipulatively controlled.

11 Claims, 37 Drawing Sheets

Related U.S. Application Data continuation of application No. 13/316,060, filed on Dec. 9, 2011, now Pat. No. 9,215,967, which is a division of application No. 11/762,132, filed on Jun. 13, 2007, now Pat. No. 8,083,667.

(60) Provisional application No. 60/813,172, filed on Jun. 13, 2006, provisional application No. 60/813,173, filed on Jun. 13, 2006, provisional application No. 60/813,207, filed on Jun. 13, 2006, provisional application No. 60/813,030, filed on Jun. 13, 2006, provisional application No. 60/813,129, filed on Jun. 13, 2006, provisional application No. 60/813,328, filed on Jun. 13, 2006, provisional application No. 60/813,126, filed on Jun. 13, 2006, provisional application No. 60/813,075, filed on Jun. 13, 2006, provisional application No. 60/813,028, filed on Jun. 13, 2006, provisional application No. 60/813,131, filed on Jun. 13, 2006, provisional application No. 60/813,198, filed on Jun. 13, 2006, provisional application No. 60/813,029, filed on Jun. 13, 2006, provisional application No. 60/813,125, filed on Jun. 13, 2006.

(51) Int. Cl.

| | |
|---|---|
| *A61B 1/005* | (2006.01) |
| *A61B 34/37* | (2016.01) |
| *A61B 34/30* | (2016.01) |
| *A61B 1/018* | (2006.01) |
| *A61B 90/10* | (2016.01) |
| *A61B 1/002* | (2006.01) |
| *A61B 5/00* | (2006.01) |
| *A61B 8/12* | (2006.01) |
| *A61B 1/04* | (2006.01) |
| *A61B 1/06* | (2006.01) |
| *A61B 1/05* | (2006.01) |
| *A61B 17/00* | (2006.01) |
| *A61B 90/00* | (2016.01) |
| *A61B 17/34* | (2006.01) |
| *A61B 34/20* | (2016.01) |

(52) U.S. Cl.
CPC ........ *A61B 1/0051* (2013.01); *A61B 1/00087* (2013.01); *A61B 1/00149* (2013.01); *A61B 1/00154* (2013.01); *A61B 1/00165* (2013.01); *A61B 1/00193* (2013.01); *A61B 1/018* (2013.01); *A61B 1/04* (2013.01); *A61B 1/05* (2013.01); *A61B 1/06* (2013.01); *A61B 5/0086* (2013.01); *A61B 8/12* (2013.01); *A61B 17/00234* (2013.01); *A61B 34/30* (2016.02); *A61B 34/37* (2016.02); *A61B 34/71* (2016.02); *A61B 34/72* (2016.02); *A61B 90/10* (2016.02); *A61B 1/0055* (2013.01); *A61B 90/361* (2016.02); *A61B 2017/0034* (2013.01); *A61B 2017/00314* (2013.01); *A61B 2017/00323* (2013.01); *A61B 2017/3447* (2013.01); *A61B 2034/2061* (2016.02); *A61B 2034/301* (2016.02); *A61B 2034/305* (2016.02); *A61B 2034/306* (2016.02)

(58) Field of Classification Search
CPC ... A61B 1/0056; A61B 1/0057; A61B 1/0058; A61B 1/008; A61B 1/00147; A61B 1/00149; A61B 1/00154; A61B 1/0016; A61B 34/30; A61B 34/32; A61B 34/35; A61B 34/37; A61B 34/70–72; A61B 34/74; A61B 2017/2908

See application file for complete search history.

(56) References Cited

U.S. PATENT DOCUMENTS

| | | | |
|---|---|---|---|
| 4,557,255 A * | 12/1985 | Goodman | A61B 1/307 600/104 |
| 4,653,476 A * | 3/1987 | Bonnet | A61B 1/00098 600/106 |
| 4,854,301 A * | 8/1989 | Nakajima | A61B 1/00147 600/102 |
| 4,868,644 A * | 9/1989 | Yabe | A61B 1/0052 348/76 |
| 4,873,965 A * | 10/1989 | Danieli | A61B 1/0055 600/141 |
| 5,184,601 A * | 2/1993 | Putman | B25J 9/042 312/209 |
| 5,257,617 A * | 11/1993 | Takahashi | A61B 1/00142 600/123 |
| 5,305,203 A * | 4/1994 | Raab | A61B 17/00 606/1 |
| 5,346,504 A * | 9/1994 | Ortiz | A61B 34/70 600/116 |
| 5,417,210 A * | 5/1995 | Funda | A61B 1/00193 348/65 |
| 5,520,678 A * | 5/1996 | Heckele | A61B 17/29 606/1 |
| 5,536,236 A * | 7/1996 | Yabe | A61B 1/00089 600/125 |
| 5,624,380 A * | 4/1997 | Takayama | A61B 1/0058 600/141 |
| 5,665,096 A | 9/1997 | Yoon | |
| 5,674,182 A * | 10/1997 | Suzuki | A61B 1/00057 600/121 |
| 5,693,003 A * | 12/1997 | Wolfelschneider | A61B 1/00165 600/117 |
| 5,695,448 A * | 12/1997 | Kimura | A61B 1/0005 600/114 |
| 5,697,939 A * | 12/1997 | Kubota | A61B 90/50 606/130 |
| 5,752,973 A | 5/1998 | Kieturakis et al. | |
| 5,813,976 A * | 9/1998 | Filipi | A61B 1/0055 600/102 |
| 5,833,656 A * | 11/1998 | Smith | B25J 9/06 604/95.01 |
| 5,855,569 A | 1/1999 | Komi et al. | |
| 5,876,325 A * | 3/1999 | Mizuno | A61B 1/00188 600/102 |
| 5,916,146 A * | 6/1999 | Allotta | A61B 1/0051 600/141 |
| 5,928,143 A * | 7/1999 | McNaughton | A61B 5/24 600/373 |
| 6,024,695 A * | 2/2000 | Taylor | A61B 34/20 600/102 |
| 6,071,232 A * | 6/2000 | Knighton | A61B 17/00008 600/104 |
| 6,071,233 A * | 6/2000 | Ishikawa | A61B 1/0014 600/104 |
| 6,106,511 A * | 8/2000 | Jensen | B25J 9/1065 600/102 |
| 6,120,433 A * | 9/2000 | Mizuno | A61B 34/70 600/102 |
| 6,352,503 B1 * | 3/2002 | Matsui | A61B 17/1285 600/104 |
| 6,371,952 B1 | 4/2002 | Madhani et al. | |
| 6,450,950 B2 | 9/2002 | Irion | |
| 6,458,074 B1 * | 10/2002 | Matsui | A61B 1/00098 600/104 |
| 6,527,753 B2 * | 3/2003 | Sekine | A61B 1/00135 600/104 |
| 6,569,084 B1 * | 5/2003 | Mizuno | A61B 1/00149 248/325 |

(56) References Cited

U.S. PATENT DOCUMENTS

| | | | |
|---|---|---|---|
| 6,574,355 B2 | 6/2003 | Green | |
| 6,594,552 B1* | 7/2003 | Nowlin | B25J 9/1689 |
| | | | 700/260 |
| 6,648,816 B2* | 11/2003 | Irion | A61B 1/00183 |
| | | | 600/104 |
| 6,659,939 B2* | 12/2003 | Moll | A61B 34/37 |
| | | | 600/102 |
| 6,666,847 B2 | 12/2003 | Secrest et al. | |
| 6,699,180 B2* | 3/2004 | Kobayashi | A61B 1/00089 |
| | | | 600/104 |
| 6,723,106 B1* | 4/2004 | Charles | B25J 9/1065 |
| | | | 606/130 |
| 6,758,843 B2* | 7/2004 | Jensen | B25J 9/1065 |
| | | | 600/102 |
| 6,786,896 B1 | 9/2004 | Madhani et al. | |
| 6,817,974 B2 | 11/2004 | Cooper et al. | |
| 6,878,106 B1* | 4/2005 | Herrmann | A61B 1/00073 |
| | | | 600/104 |
| 6,991,603 B2 | 1/2006 | Krupa et al. | |
| 6,997,866 B2* | 2/2006 | Payandeh | A61B 90/11 |
| | | | 600/102 |
| 7,029,435 B2* | 4/2006 | Nakao | A61B 1/00071 |
| | | | 600/104 |
| 7,066,926 B2 | 6/2006 | Wallace et al. | |
| 7,090,637 B2* | 8/2006 | Danitz | A61B 1/0055 |
| | | | 600/141 |
| 7,090,683 B2* | 8/2006 | Brock | A61B 17/0469 |
| | | | 606/1 |
| 7,171,279 B2 | 1/2007 | Buckingham et al. | |
| 7,198,599 B2* | 4/2007 | Goto | A61B 1/0125 |
| | | | 600/154 |
| 7,220,227 B2* | 5/2007 | Sasaki | A61B 1/00137 |
| | | | 600/102 |
| 7,670,281 B2* | 3/2010 | Kronner | A61B 90/50 |
| | | | 600/102 |
| 7,762,949 B2* | 7/2010 | Nakao | A61B 1/00105 |
| | | | 600/153 |
| 7,833,156 B2* | 11/2010 | Williams | A61B 1/00052 |
| | | | 600/184 |
| 7,850,600 B1* | 12/2010 | Piskun | A61B 17/3423 |
| | | | 600/114 |
| 7,901,399 B2* | 3/2011 | Brock | A61B 34/35 |
| | | | 606/1 |
| 7,931,661 B2* | 4/2011 | Saadat | A61B 17/06166 |
| | | | 606/144 |
| 7,942,868 B2 | 5/2011 | Cooper et al. | |
| 7,947,035 B2* | 5/2011 | Miyamoto | A61B 90/36 |
| | | | 606/1 |
| 8,057,385 B2 | 11/2011 | Cooper et al. | |
| 8,083,667 B2 | 12/2011 | Cooper et al. | |
| 8,182,491 B2* | 5/2012 | Selover | A61B 90/13 |
| | | | 606/104 |
| 8,221,306 B2* | 7/2012 | Okada | A61B 1/00087 |
| | | | 600/106 |
| 8,277,373 B2* | 10/2012 | Maahs | A61B 1/0008 |
| | | | 600/107 |
| 8,287,554 B2* | 10/2012 | Cerier | A61B 17/00234 |
| | | | 606/142 |
| 8,353,815 B2* | 1/2013 | Okada | A61B 1/012 |
| | | | 600/104 |
| 8,518,024 B2* | 8/2013 | Williams | A61B 1/00128 |
| | | | 606/1 |
| 8,672,833 B2 | 3/2014 | Cooper et al. | |
| 8,679,099 B2 | 3/2014 | Cooper et al. | |
| 8,753,262 B2* | 6/2014 | Sugiyama | A61B 1/018 |
| | | | 600/114 |
| 8,986,196 B2 | 3/2015 | Larkin et al. | |
| 9,215,967 B2 | 12/2015 | Cooper et al. | |
| 9,510,734 B2 | 12/2016 | Cooper et al. | |
| 10,448,813 B2 | 10/2019 | Cooper et al. | |
| 2001/0018550 A1* | 8/2001 | Boebel | A61B 1/018 |
| | | | 600/107 |
| 2001/0027313 A1* | 10/2001 | Shimmura | A61B 90/50 |
| | | | 606/1 |
| 2002/0007110 A1* | 1/2002 | Irion | A61B 1/05 |
| | | | 600/170 |
| 2002/0062063 A1* | 5/2002 | Ogura | A61B 1/0055 |
| | | | 600/148 |
| 2002/0111534 A1* | 8/2002 | Suzuki | A61B 17/0469 |
| | | | 600/102 |
| 2002/0156345 A1* | 10/2002 | Eppler | A61B 1/313 |
| | | | 600/114 |
| 2003/0040657 A1* | 2/2003 | Yamaya | A61B 90/30 |
| | | | 600/107 |
| 2003/0135204 A1* | 7/2003 | Lee | A61B 90/36 |
| | | | 606/1 |
| 2003/0135230 A1* | 7/2003 | Massey | A61B 1/12 |
| | | | 606/190 |
| 2003/0176880 A1* | 9/2003 | Long | A61B 10/04 |
| | | | 606/167 |
| 2003/0233024 A1* | 12/2003 | Ando | A61B 1/00096 |
| | | | 600/111 |
| 2004/0015050 A1* | 1/2004 | Goto | A61B 18/1492 |
| | | | 600/104 |
| 2004/0024387 A1* | 2/2004 | Payandeh | A61B 90/11 |
| | | | 606/1 |
| 2004/0106850 A1* | 6/2004 | Yamaya | A61B 1/00098 |
| | | | 600/107 |
| 2004/0193146 A1* | 9/2004 | Lee | A61B 34/71 |
| | | | 606/1 |
| 2004/0236316 A1* | 11/2004 | Danitz | A61B 34/70 |
| | | | 606/1 |
| 2005/0049455 A1 | 3/2005 | Ootawara et al. | |
| 2005/0049580 A1* | 3/2005 | Brock | A61B 90/50 |
| | | | 606/1 |
| 2005/0059960 A1 | 3/2005 | Simaan et al. | |
| 2005/0075536 A1* | 4/2005 | Otsuka | A61B 90/50 |
| | | | 600/102 |
| 2005/0090709 A1* | 4/2005 | Okada | A61B 1/042 |
| | | | 600/104 |
| 2005/0096502 A1* | 5/2005 | Khalili | A61B 1/313 |
| | | | 600/106 |
| 2005/0107663 A1* | 5/2005 | Saadat | A61B 1/0055 |
| | | | 600/104 |
| 2005/0107667 A1* | 5/2005 | Danitz | A61B 17/07207 |
| | | | 600/139 |
| 2005/0113640 A1 | 5/2005 | Saadat et al. | |
| 2005/0124912 A1* | 6/2005 | Griego | A61B 17/29 |
| | | | 600/564 |
| 2005/0137529 A1 | 6/2005 | Mantell | |
| 2005/0165272 A1* | 7/2005 | Okada | A61B 1/00087 |
| | | | 600/114 |
| 2005/0192475 A1* | 9/2005 | Okada | A61B 1/0052 |
| | | | 600/106 |
| 2005/0222493 A1 | 10/2005 | Kohno et al. | |
| 2005/0222554 A1* | 10/2005 | Wallace | A61B 8/4461 |
| | | | 606/1 |
| 2005/0228224 A1* | 10/2005 | Okada | A61B 1/00135 |
| | | | 600/104 |
| 2005/0234293 A1* | 10/2005 | Yamamoto | A61B 90/57 |
| | | | 600/102 |
| 2005/0234294 A1* | 10/2005 | Saadat | A61B 1/00098 |
| | | | 600/104 |
| 2005/0234296 A1* | 10/2005 | Saadat | A61B 1/00183 |
| | | | 600/129 |
| 2005/0234435 A1* | 10/2005 | Layer | A61B 17/3403 |
| | | | 606/1 |
| 2005/0250989 A1* | 11/2005 | Suzuki | A61B 17/29 |
| | | | 600/106 |
| 2005/0256371 A1* | 11/2005 | Schara | A61B 1/313 |
| | | | 600/102 |
| 2005/0267335 A1* | 12/2005 | Okada | A61B 1/00188 |
| | | | 600/173 |
| 2005/0272975 A1* | 12/2005 | McWeeney | A61B 1/00103 |
| | | | 600/113 |
| 2005/0272977 A1* | 12/2005 | Saadat | A61B 1/018 |
| | | | 600/114 |

(56) References Cited

U.S. PATENT DOCUMENTS

| | | | |
|---|---|---|---|
| 2005/0273084 A1* | 12/2005 | Hinman | A61B 17/00 606/1 |
| 2005/0273085 A1* | 12/2005 | Hinman | A61M 25/0105 606/1 |
| 2006/0036267 A1 | 2/2006 | Saadat et al. | |
| 2006/0079864 A1* | 4/2006 | Kronner | A61B 90/50 606/1 |
| 2006/0084945 A1* | 4/2006 | Moll | A61B 34/71 606/1 |
| 2006/0095022 A1* | 5/2006 | Moll | A61B 46/10 606/1 |
| 2006/0100610 A1* | 5/2006 | Wallace | A61B 8/4254 606/1 |
| 2006/0111210 A1* | 5/2006 | Hinman | A61B 17/07207 474/206 |
| 2006/0111615 A1* | 5/2006 | Danitz | A61B 1/00135 600/141 |
| 2006/0155262 A1* | 7/2006 | Kishi | A61B 34/71 606/1 |
| 2006/0178560 A1* | 8/2006 | Saadat | A61B 1/0055 600/114 |
| 2006/0189845 A1* | 8/2006 | Maahs | A61B 1/0051 600/146 |
| 2006/0195070 A1* | 8/2006 | Hagn | A61B 34/70 606/1 |
| 2006/0235458 A1* | 10/2006 | Belson | A61M 25/0032 606/191 |
| 2006/0293643 A1* | 12/2006 | Wallace | A61B 34/37 606/1 |
| 2007/0032701 A1 | 2/2007 | Fowler et al. | |
| 2007/0043338 A1* | 2/2007 | Moll | A61B 17/062 606/1 |
| 2007/0060879 A1* | 3/2007 | Weitzner | A61M 25/10184 604/95.04 |
| 2007/0072466 A1* | 3/2007 | Miyamoto | A61B 90/36 439/188 |
| 2007/0167679 A1* | 7/2007 | Miyamoto | A61B 1/0055 600/106 |
| 2007/0167680 A1* | 7/2007 | Miyamoto | A61B 1/0055 600/106 |
| 2007/0197864 A1* | 8/2007 | Dejima | A61B 17/3421 600/106 |
| 2007/0197896 A1* | 8/2007 | Moll | A61B 1/00039 600/407 |
| 2007/0225554 A1* | 9/2007 | Maseda | A61B 1/00108 600/104 |
| 2007/0244514 A1* | 10/2007 | Weizman | A61B 10/06 606/205 |
| 2007/0260114 A1* | 11/2007 | Miyamoto | A61B 17/29 600/114 |
| 2007/0270636 A1* | 11/2007 | Spera | A61B 1/018 600/104 |
| 2008/0051629 A1* | 2/2008 | Sugiyama | A61B 1/018 600/114 |
| 2008/0140087 A1* | 6/2008 | Barbagli | B25J 13/02 606/130 |
| 2008/0215067 A1 | 9/2008 | Dupont et al. | |
| 2009/0171271 A1* | 7/2009 | Webster | A61M 25/0108 604/95.01 |
| 2010/0217076 A1* | 8/2010 | Ratnakar | A61B 1/0125 600/104 |
| 2010/0249774 A1* | 9/2010 | Truckai | A61B 17/12136 606/41 |
| 2012/0029277 A1* | 2/2012 | Sholev | A61B 1/045 600/102 |
| 2016/0066773 A1* | 3/2016 | Cooper | A61B 1/00165 600/104 |

OTHER PUBLICATIONS

Advisory Action dated Jul. 29, 2010 for U.S. Appl. No. 11/762,135, filed Jun. 13, 2007.
Examiner Interview Summary dated Sep. 9, 2010 for U.S. Appl. No. 11/762,135, filed Jun. 13, 2007.
Examiner Interview Summary dated Oct. 19, 2010 for U.S. Appl. No. 11/762,132, filed Jun. 13, 2007.
Final Office Action dated Aug. 14, 2013 for U.S. Appl. No. 13/248,930, filed Sep. 29, 2011.
Final Office Action dated Aug. 15, 2013 for U.S. Appl. No. 13/614,659, filed Sep. 13, 2012.
Final Office Action dated Aug. 19, 2010 for U.S. Appl. No. 11/762,132, filed Jun. 13, 2007.
Final Office Action dated Jun. 19, 2017 for U.S. Appl. No. 14/943,216, filed Nov. 17, 2015, 22 pages.
Final Office Action dated Aug. 20, 2013 for U.S. Appl. No. 13/316,060, filed Dec. 9, 2011.
Final Office Action dated Apr. 22, 2019 for U.S. Appl. No. 14/943,216, filed Nov. 17, 2015, 11 pages.
Final Office Action dated May 24, 2010 for U.S. Appl. No. 11/762,135, filed Jun. 13, 2007.
Non-Final Office Action dated Mar. 2, 2011 for U.S. Appl. No. 11/762,135, filed Jun. 13, 2007.
Non-final Office Action dated Mar. 7, 2017 for U.S. Appl. No. 14/943,216, filed Nov. 17, 2015, 17 pages.
Non-Final Office Action dated Mar. 9, 2010 for U.S. Appl. No. 11/762,132, filed Jun. 13, 2007.
Non-final Office Action dated Jan. 10, 2019 for U.S. Appl. No. 14/943,216, filed Nov. 17, 2015, 22 pages.
Non-Final Office Action dated Mar. 13, 2013 for U.S. Appl. No. 13/614,659, filed Sep. 13, 2012.
Non-Final Office Action dated Mar. 15, 2013 for U.S. Appl. No. 13/248,930, filed Sep. 29, 2011.
Non-Final Office Action dated Feb. 16, 2011 for U.S. Appl. No. 11/762,132, filed Jun. 13, 2007.
Non-Final Office Action dated Mar. 21, 2013 for U.S. Appl. No. 13/316,060, filed Dec. 9, 2011.
Non-Final Office Action dated Nov. 30, 2009 for U.S. Appl. No. 11/762,132, filed Jun. 13, 2007.
Notice of Allowance dated Jun. 24, 2011 for U.S. Appl. No. 11/762,135, filed Jun. 13, 2007.
Notice of Allowance dated Aug. 25, 2011 for U.S. Appl. No. 11/762,132, filed Jun. 13, 2007.
Notice of Allowance dated Jun. 25, 2019 for U.S. Appl. No. 14/943,216, filed Nov. 17, 2015.
Notice of Allowance dated Oct. 29, 2013 for U.S. Appl. No. 13/614,659, filed Sep. 13, 2012.
Notice of Allowance dated Oct. 30, 2013 for U.S. Appl. No. 13/248,930, filed Sep. 29, 2011.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

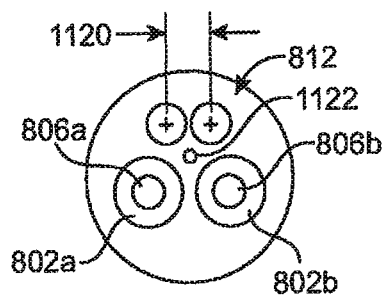
FIG. 11A
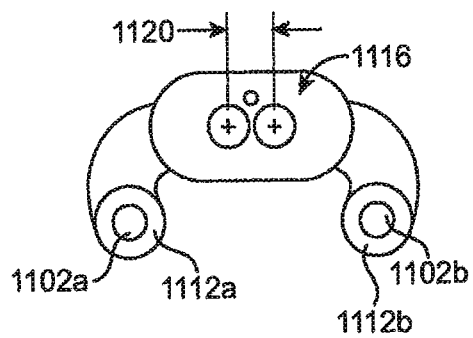
FIG. 11B
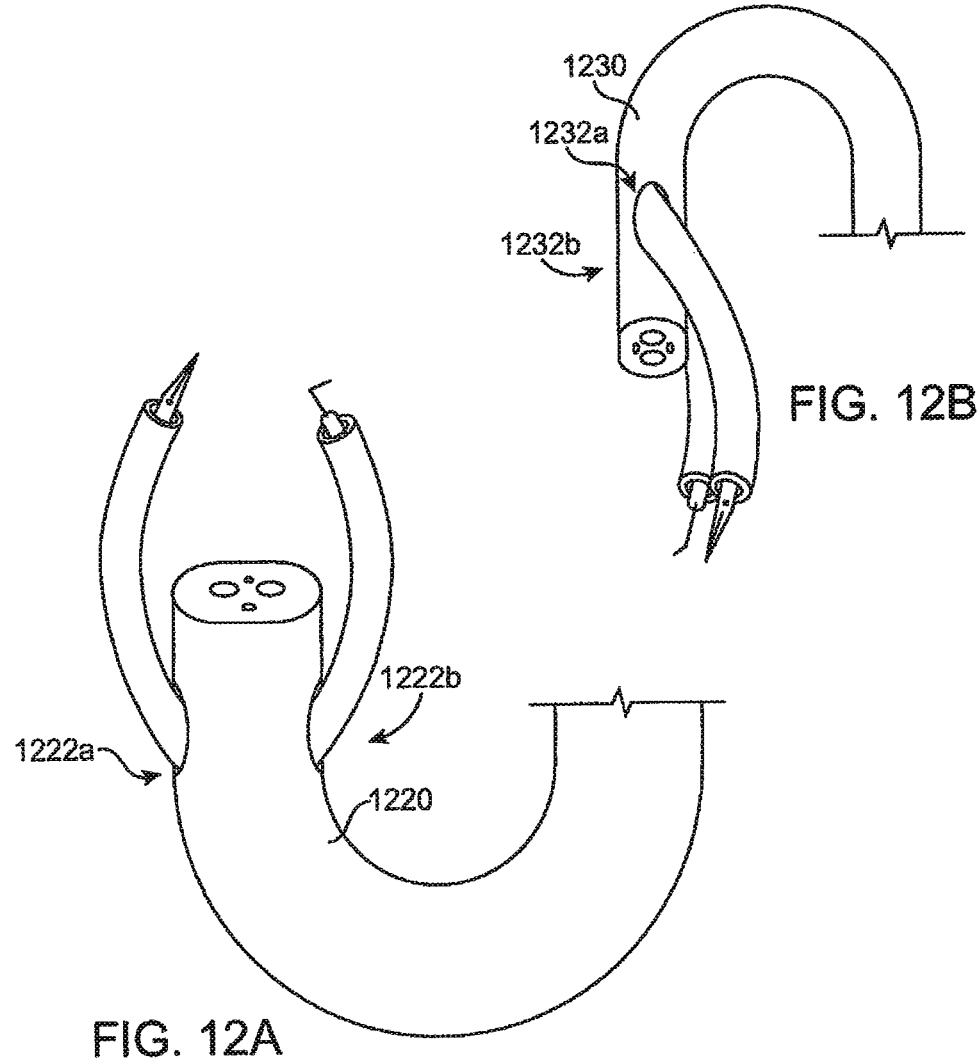
FIG. 12B
FIG. 12A

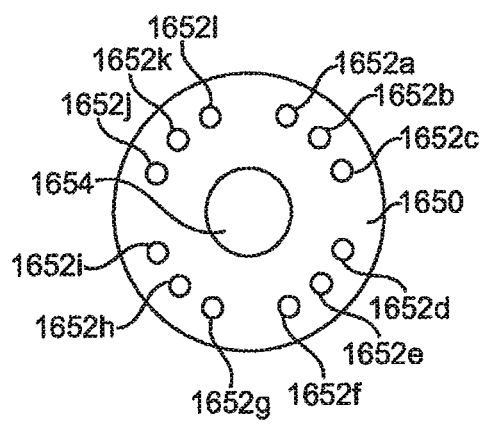
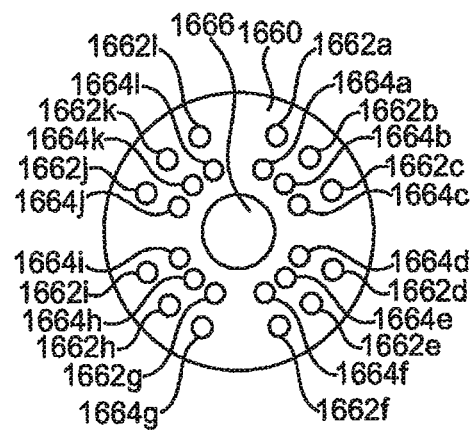
FIG. 16F  FIG. 16G
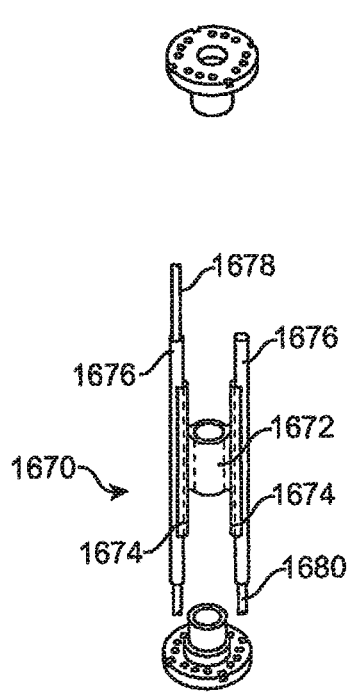
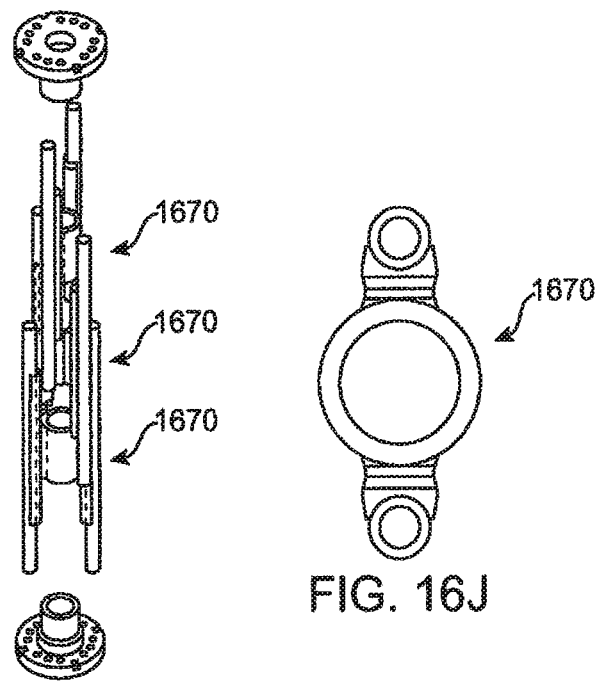
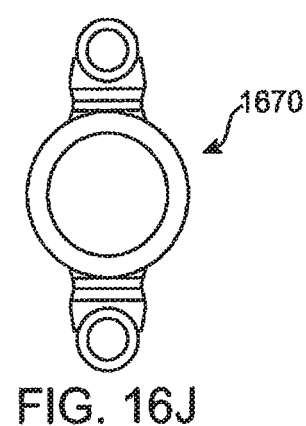
FIG. 16H  FIG. 16I  FIG. 16J

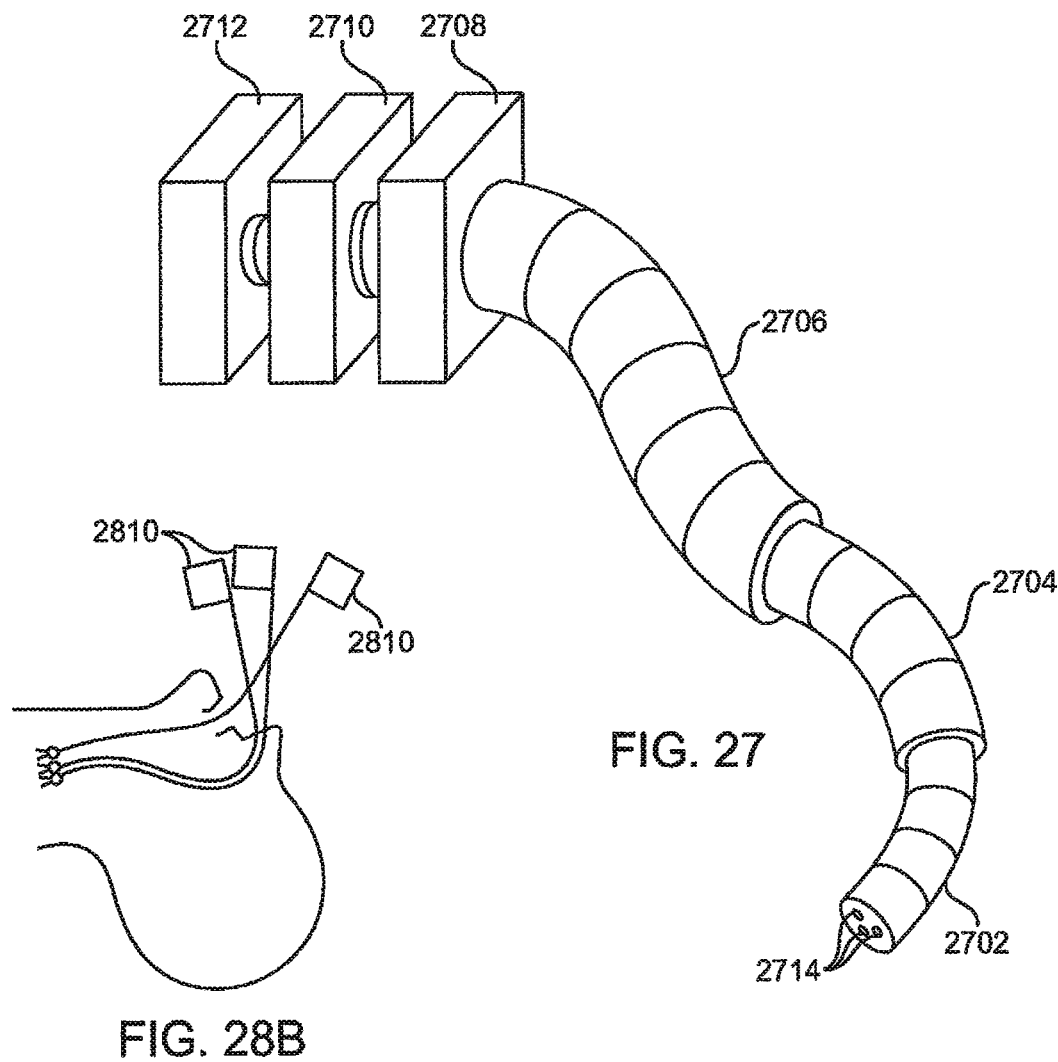
FIG. 27
FIG. 28B
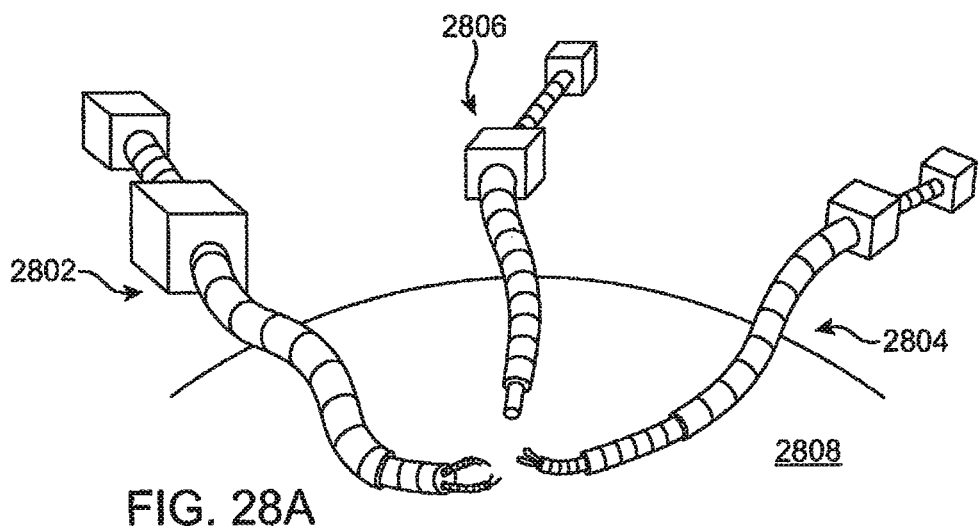
FIG. 28A

SIDE LOOKING MINIMALLY INVASIVE SURGERY INSTRUMENT ASSEMBLY

CROSS REFERENCE TO RELATED APPLICATIONS

This application is a continuation of U.S. patent application Ser. No. 14/943,216 (filed Nov. 17, 2015), which is a continuation of U.S. patent application Ser. No. 13/316,060 (filed Dec. 9, 2011 and now U.S. Pat. No. 9,215,967), which is a divisional of U.S. patent application Ser. No. 11/762,132 (filed Jun. 13, 2007 and now U.S. Pat. No. 8,083,667), which are all incorporated herein by reference, and which claims the priority benefit of the following United States Provisional Patent Applications, all of which are incorporated by reference:

U.S. Patent Application No. 60/813,028 entitled "Single port system 2" filed 13 Jun. 2006 by Cooper et al.;

U.S. Patent Application No. 60/813,029 entitled "Single port surgical system 1" filed 13 Jun. 2006 by Larkin;

U.S. Patent Application No. 60/813,030 entitled "Independently actuated optical train" filed 13 Jun. 2006 by Larkin et al.;

U.S. Patent Application No. 60/813,075 entitled "Modular cannula architecture" filed 13 Jun. 2006 by Larkin et al.;

U.S. Patent Application No. 60/813,125 entitled "Methods for delivering instruments to a surgical site with minimal disturbance to intermediate structures" filed 13 Jun. 2006 by Larkin et al.;

U.S. Patent Application No. 60/813,126 entitled "Rigid single port surgical system" filed 13 Jun. 2006 by Cooper;

U.S. Patent Application No. 60/813,129 entitled "Minimum net force actuation" filed 13 Jun. 2006 by Cooper et al.;

U.S. Patent Application No. 60/813,131 entitled "Side working tools and camera" filed 13 Jun. 2006 by Duval et al.;

U.S. Patent Application No. 60/813,172 entitled "Passing cables through joints" filed 13 Jun. 2006 by Cooper;

U.S. Patent Application No. 60/813,173 entitled "Hollow smoothly bending instrument joints" filed 13 Jun. 2006 by Larkin et al.;

U.S. Patent Application No. 60/813,198 entitled "Retraction devices and methods" filed 13 Jun. 2006 by Mohr et al.;

U.S. Patent Application No. 60/813,207 entitled "Sensory architecture for endoluminal robots" filed 13 Jun. 2006 by Diolaiti et al.; and U.S. Patent Application No. 60/813,328 entitled "Concept for single port laparoscopic surgery" filed 13 Jun. 2006 by Larkin et al.

In addition, this application is related to the following concurrently filed United States Patent Applications, all of which are incorporated by reference:

U.S. patent application Ser. No. 11/762,217 entitled "Retraction of tissue for single port entry, robotically assisted medical procedures" by Mohr;

U.S. patent application Ser. No. 11/762,222 entitled "Bracing of bundled medical devices for single port entry, robotically assisted medical procedures" by Mohr et al.;

U.S. patent application Ser. No. 11/762,231 entitled "Extendable suction surface for bracing medical devices during robotically assisted medical procedures" by Schena;

U.S. patent application Ser. No. 11/762,236 entitled "Control system configured to compensate for non-ideal actuator-to-joint linkage characteristics in a medical robotic system" by Diolaiti et al.;

U.S. patent application Ser. No. 11/762,185 entitled "Surgical instrument actuation system" by Cooper et al.;

U.S. patent application Ser. No. 11/762,172 entitled "Surgical instrument actuator" by Cooper et al.;

U.S. patent application Ser. No. 11/762,165 entitled "Minimally invasive surgical system" by Larkin et at;

U.S. patent application Ser. No. 11/762,161 entitled "Minimally invasive surgical instrument advancement" by Larkin et al.;

U.S. patent application Ser. No. 11/762,158 entitled "Surgical instrument control and actuation" by Cooper et al.;

U.S. patent application Ser. No. 11/762,154 entitled "Surgical instrument with parallel motion mechanism" by Cooper;

U.S. patent application Ser. No. 11/762,149 entitled "Minimally invasive surgical apparatus with side exit instruments" by Larkin;

U.S. patent application Ser. No. 11/762,170 entitled "Minimally invasive surgical apparatus with side exit instruments" by Larkin;

U.S. patent application Ser. No. 11/762,143 entitled "Minimally invasive surgical instrument system" by Larkin;

U.S. patent application Ser. No. 11/762,135 entitled "Side looking minimally invasive surgery instrument assembly" by Cooper et al.;

U.S. patent application Ser. No. 11/762,127 entitled "Guide tube control of minimally invasive surgical instruments" by Larkin et al.;

U.S. patent application Ser. No. 11/762,123 entitled "Minimally invasive surgery guide tube" by Larkin et al.;

U.S. patent application Ser. No. 11/762,120 entitled "Minimally invasive surgery guide tube" by Larkin et al.;

U.S. patent application Ser. No. 11/762,118 entitled "Teleoperated surgical retractor system" by Larkin;

U.S. patent application Ser. No. 11/762,114 entitled "Minimally invasive surgical illumination" by Schena et al.;

U.S. patent application Ser. No. 11/762,110 entitled "Retrograde instrument" by Duval et al.;

U.S. patent application Ser. No. 11/762,204 entitled "Retrograde instrument" by Duval et al.;

U.S. patent application Ser. No. 11/762,202 entitled "Preventing instrument/tissue collisions" by Larkin;

U.S. patent application Ser. No. 11/762,189 entitled "Minimally invasive surgery instrument assembly with reduced cross section" by Larkin et al.;

U.S. patent application Ser. No. 11/762,191 entitled "Minimally invasive surgical system" by Larkin et at;

U.S. patent application Ser. No. 11/762,196 entitled "Minimally invasive surgical system" by Duval et al.; and U.S. patent application Ser. No. 11/762,200 entitled "Minimally invasive surgical system" by Diolaiti, issued as U.S. Pat. No. 7,725,215 on May 25, 2010.

STATEMENT REGARDING FEDERALLY SPONSORED RESEARCH OR DEVELOPMENT

None.

BACKGROUND

1. Field of Invention

Aspects of the invention are associated with systems and procedures used for minimally invasive surgery, and more particularly to telemanipulative systems used for such surgery.

2. Background Art

Minimally invasive surgery is known under various names (e.g., endoscopy, laparoscopy, arthroscopy, endovascular, keyhole, etc.), often specific to the anatomical area in which work is done. Such surgery includes the use of both hand-held and teleoperated/telemanipulated/telepresence (robot assisted/telerobotics) equipment, such as the da Vinci® Surgical System made by Intuitive Surgical, Inc. of Sunnyvale, Calif. Both diagnostic (e.g., biopsy) and therapeutic procedures are done. Instruments may be inserted into a patient percutaneously via surgical incision or via natural orifice. A new, experimental minimally invasive surgery variation is Natural Orifice Transluminal Endoscopic Surgery (NOTES), in which instruments enter via a natural orifice (e.g., mouth, nostril, ear canal, anus, vagina, urethra) and continue to a surgical site via a transluminal incision (e.g., in a gastric or colonic wall) within the body. Although teleoperative surgery using the da Vinci® Surgical System provides great benefits over, for instance, many hand-held procedures, for some patients and for some anatomical areas the da Vinci® Surgical System is unable to effectively access a surgical site. In addition, further reducing the size and number of incisions aids patient recovery and helps reduce patient trauma and discomfort.

The number of degrees of freedom (DOFs) is the number of independent variables that uniquely identify the pose/configuration of a system. Since robotic manipulators are kinematic chains that map the (input) joint space into the (output) Cartesian space, the notion of DOF can be expressed in any of these two spaces. In particular, the set of joint DOFs is the set of joint variables for all the independently controlled joints. Without loss of generality, joints are mechanisms that provide a single translational (prismatic joints) or rotational (revolute joints) DOF. Any mechanism that provides more than one DOF motion is considered, from a kinematic modeling perspective, as two or more separate joints. The set of Cartesian DOFs is usually represented by the three translational (position) variables (e.g., surge, heave, sway) and by the three rotational (orientation) variables (e.g. Euler angles or roll/pitch/yaw angles) that describe the position and orientation of an end effector (or tip) frame with respect to a given reference Cartesian frame.

For example, a planar mechanism with an end effector mounted on two independent and perpendicular rails has the capability of controlling the x/y position within the area spanned by the two rails (prismatic DOFs). If the end effector can be rotated around an axis perpendicular to the plane of the rails, then there are then three input DOFs (the two rail positions and the yaw angle) that correspond to three output DOFs (the x/y position and the orientation angle of the end effector).

Although the number of Cartesian DOFs is at most six, a condition in which all the translational and orientational variables are independently controlled, the number of joint DOFs is generally the result of design choices that involve considerations of the complexity of the mechanism and the task specifications. Accordingly, the number of joint DOFs can be more than, equal to, or less than six. For non-redundant kinematic chains, the number of independently controlled joints is equal to the degree of mobility for the end effector frame. For a certain number of prismatic and revolute joint DOFs, the end effector frame will have an equal number of DOFs (except when in singular configurations) in Cartesian space that will correspond to a combination of translational (x/y/z position) and rotational (roll/pitch/yaw orientation angle) motions.

The distinction between the input and the output DOFs is extremely important in situations with redundant or "defective" kinematic chains (e.g., mechanical manipulators). In particular, "defective" manipulators have fewer than six independently controlled joints and therefore do not have the capability of fully controlling end effector position and orientation. Instead, defective manipulators are limited to controlling only a subset of the position and orientation variables. On the other hand, redundant manipulators have more than six joint DOFs. Thus, a redundant manipulator can use more than one joint configuration to establish a desired 6-DOF end effector pose. In other words, additional degrees of freedom can be used to control not just the end effector position and orientation but also the "shape" of the manipulator itself. In addition to the kinematic degrees of freedom, mechanisms may have other DOFs, such as the pivoting lever movement of gripping jaws or scissors blades.

It is also important to consider reference frames for the space in which DOFs are specified. For example, a single DOF change in joint space (e.g., the joint between two links rotates) may result in a motion that combines changes in the Cartesian translational and orientational variables of the frame attached to the distal tip of one of the links (the frame at the distal tip both rotates and translates through space). Kinematics describes the process of converting from one measurement space to another. For example, using joint space measurements to determine the Cartesian space position and orientation of a reference frame at the tip of a kinematic chain is "forward" kinematics. Using Cartesian space position and orientation for the reference frame at the tip of a kinematic chain to determine the required joint positions is "inverse" kinematics. If there are any revolute joints, kinematics involves non-linear (trigonometric) functions.

SUMMARY

In accordance with aspects of the invention, a surgical instrument is inserted through a guide tube. The surgical instrument exits at an intermediate position of the guide tube and is oriented to be substantially parallel to the guide tube's longitudinal axis as it exits. A stereoscopic image capture component is on the guide tube between the intermediate position and the guide tube's distal end. The image capture component's field of view is generally perpendicular to the guide tube's longitudinal axis. The guide tube is jointed to allow the image capture component to be moved. The surgical instruments and the guide tube are telemanipulatively controlled.

BRIEF DESCRIPTION OF THE DRAWINGS

FIGS. 11A and 11B are diagrammatic end views of surgical instrument assemblies.

FIGS. 12A and 12B are diagrammatic views of retroflexive positions.

FIGS. 16F and 16G are diagrammatic end views of link disks in a parallel motion mechanism.

FIGS. 16H and 16I are diagrammatic perspective views of stiffening brackets in a parallel motion mechanism.

FIG. 16J is a diagrammatic end view of a stiffening bracket.

FIG. 27 is a diagrammatic view of transmission mechanisms associated with flexible coaxial guide tubes and instruments.

FIG. 28A is a diagrammatic view of multi-port surgery.

FIG. 28B is another diagrammatic view of multi-port surgery.

DETAILED DESCRIPTION

Figure 1:
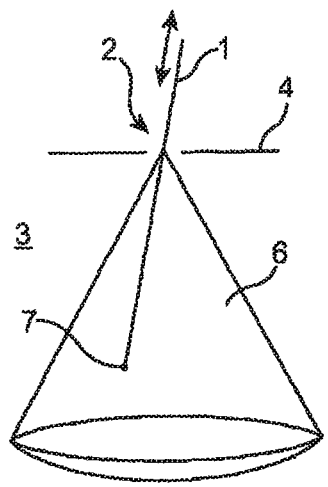
FIG. 1 is a diagrammatic view of a minimally invasive surgical instrument and its motion about a pivot point represented by an incision or natural orifice.

This description and the accompanying drawings that illustrate aspects and embodiments of the present invention should not be taken as limiting—the claims define the protected invention. Various mechanical, compositional, structural, electrical, and operational changes may be made without departing from the spirit and scope of this description and the claims. In some instances, well-known circuits, structures, and techniques have not been shown in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Telemanipulation and like terms generally refer to an operator manipulating a master device (e.g., an input kinematic chain) in a relatively natural way (e.g., a natural hand or finger movement), whereupon the master device movements are made into commands that are processed and transmitted in real time to a slave device (e.g., an output kinematic chain) that reacts nearly instantaneously to the commands and to environmental forces. Telemanipulation is disclosed in U.S. Pat. No. 6,574,355 (Green), which is incorporated by reference.

To avoid repetition in the figures and the descriptions below of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description.

Accordingly, several general aspects apply to various descriptions below. For example, at least one surgical end effector is shown or described in various figures. An end effector is the part of the minimally invasive surgical instrument or assembly that performs a specific surgical function (e.g., forceps/graspers, needle drivers, scissors, electrocautery hooks, staplers, clip appliers/removers, etc.). Many end effectors have a single DOF (e.g., graspers that open and close). The end effector may be coupled to the surgical instrument body with a mechanism the provides one or more additional DOFs, such as "wrist" type mechanisms. Examples of such mechanisms are shown in U.S. Pat. No. 6,371,952 (Madhani et al.) and in U.S. Pat. No. 6,817,974 (Cooper et al.), both of which are incorporated by reference, and may be known as various Intuitive Surgical, Inc. Endowrist® mechanisms as used on both 8 mm and 5 mm instruments for the da Vinci® Surgical System. Although the surgical instruments described herein generally include end effectors, it should be understood that in some aspects an end effector may be omitted. For example, the distal tip of an instrument body shaft may be used to retract tissue. As another example, suction or irrigation openings may exist at the distal tip of a body shaft or the wrist mechanism. In these aspects, it should be understood that descriptions of positioning and orienting an end effector include positioning and orienting the tip of a surgical instrument that does not have an end effector. For example, a description that addresses the reference frame for a tip of an end effector should also be read to include the reference frame of the a tip of a surgical instrument that does not have an end effector.

Throughout this description, it should be understood that a mono- or stereoscopic imaging system/image capture component/camera device may be placed at the distal end of an instrument wherever an end effector is shown or described (the device may be considered a "camera instrument"), or it may be placed near or at the distal end of any guide tube or other instrument assembly element. Accordingly, the terms "imaging system" and the like as used herein should be broadly construed to include both image capture components and combinations of image capture components with associated circuitry and hardware, within the context of the aspects and embodiments being described. Such endoscopic imaging systems (e.g., optical, infrared, ultrasound, etc.) include systems with distally positioned image sensing chips and associated circuits that relay captured image data via a wired or wireless connection to outside the body. Such endoscopic imaging systems also include systems that relay images for capture outside the body (e.g., by using rod lenses or fiber optics). In some instruments or instrument assemblies a direct view optical system (the endoscopic image is viewed directly at an eyepiece) may be used. An example of a distally positioned semiconductor stereoscopic imaging system is described in U.S. patent application Ser. No. 11/614,661 "Stereoscopic Endoscope" (Shafer et al.), which is incorporated by reference. Well-known endoscopic imaging system components, such as electrical and fiber optic illumination connections, are omitted or symbolically represented for clarity. Illumination for endoscopic imaging is typically represented in the drawings by a single illumination port. It should be understood that these depictions are exemplary. The sizes, positions, and numbers of illumination ports may vary. Illumination ports are typically arranged on multiple sides of the imaging apertures, or completely surrounding the imaging apertures, to minimize deep shadows.

In this description, cannulas are typically used to prevent a surgical instrument or guide tube from rubbing on patient tissue. Cannulas may be used for both incisions and natural orifices. For situations in which an instrument or guide tube does not frequently translate or rotate relative to its insertion (longitudinal) axis, a cannula may not be used. For situations that require insufflation, the cannula may include a seal to prevent excess insufflation gas leakage past the instrument or guide tube. For example, for thoracic surgery that does not require insufflation, the cannula seal may be omitted, and if instruments or guide tube insertion axis movement is minimal, then the cannula itself may be omitted. A rigid guide tube may function as a cannula in some configurations for instruments that are inserted relative to the guide tube. Cannulas and guide tubes may be, e.g., steel or extruded plastic. Plastic, which is less expensive than steel, may be suitable for one-time use.

Various instances and assemblies of flexible surgical instruments and guide tubes are shown and described. Such flexibility, in this description, is achieved in various ways. For example, a segment or an instrument or guide tube may be a continuously curving flexible structure, such as one based on a helical wound coil or on tubes with various segments removed (e.g., kerf-type cuts). Or, the flexible part may be made of a series of short, pivotally connected segments ("vertebrae") that provide a snake-like approximation of a continuously curving structure. Instrument and guide tube structures may include those in U.S. Patent Application Pub. No. US 2004/0138700 (Cooper et al.), which is incorporated by reference. For clarity, the figures and associated descriptions generally show only two segments of instruments and guide tubes, termed proximal (closer to the transmission mechanism; farther from the surgical site) and distal (farther from the transmission mechanism; closer to the surgical site). It should be understood that the instruments and guide tubes may be divided into three or more segments, each segment being rigid, passively flexible, or actively flexible. Flexing and bending as described for a distal segment, a proximal segment, or an entire mechanism also apply to intermediate segments that have been omitted for clarity. For instance, an intermediate segment between proximal and distal segments may bend in a simple or compound curve. Flexible segments may be various lengths. Segments with a smaller outside diameter may have a smaller minimum radius of curvature while bending than segments with a larger outside diameter. For cable-controlled systems, unacceptably high cable friction or binding limits minimum radius of curvature and the total bend angle while bending. The guide tube's (or any joint's) minimum bend radius is such that it does not kink or otherwise inhibit the smooth motion of the inner surgical instrument's mechanism. Flexible components may be, for example, up to approximately four feet in length and approximately 0.6 inches in diameter. Other lengths and diameters (e.g., shorter, smaller) and the degree of flexibility for a specific mechanism may be determined by the target anatomy for which the mechanism has been designed.

In some instances only a distal segment of an instrument or guide tube is flexible, and the proximal segment is rigid. In other instances, the entire segment of the instrument or guide tube that is inside the patient is flexible. In still other instances, an extreme distal segment may be rigid, and one or more other proximal segments are flexible. The flexible segments may be passive or they may be actively controllable ("steerable"). Such active control may be done using, for example, sets of opposing cables (e.g., one set controlling "pitch" and an orthogonal set controlling "yaw"; three cables can be used to perform similar action). Other control elements such as small electric or magnetic actuators, shape memory alloys, electroactive polymers ("artificial muscle"), pneumatic or hydraulic bellows or pistons, and the like may be used. In instances in which a segment of an instrument or guide tube is fully or partially inside another guide tube, various combinations of passive and active flexibility may exist. For instance, an actively flexible instrument inside a passively flexible guide tube may exert sufficient lateral force to flex the surrounding guide tube. Similarly, an actively flexible guide tube may flex a passively flexible instrument inside it. Actively flexible segments of guide tubes and instruments may work in concert. For both flexible and rigid instruments and guide tubes, control cables placed farther from the center longitudinal axis may provide a mechanical advantage over cables placed nearer to the center longitudinal axis, depending on compliance considerations in the various designs.

The flexible segment's compliance (stiffness) may vary from being almost completely flaccid (small internal frictions exist) to being substantially rigid. In some aspects, the compliance is controllable. For example, a segment or all of a flexible segment of an instrument or guide tube can be made substantially (i.e., effectively but not infinitely) rigid (the segment is "rigidizable" or "lockable"). The lockable segment may be locked in a straight, simple curve or in a compound curve shape. Locking may be accomplished by applying tension to one or more cables that run longitudinally along the instrument or guide tube that is sufficient to cause friction to prevent adjacent vertebrae from moving. The cable or cables may run through a large, central hole in each vertebra or may run through smaller holes near the vertebra's outer circumference. Alternatively, the drive element of one or more motors that move one or more control cables may be soft-locked in position (e.g., by servocontrol) to hold the cables in position and thereby prevent instrument or guide tube movement, thus locking the vertebrae in place. Keeping a motor drive element in place may be done to effectively keep other movable instrument and guide tube components in place as well. It should be understood that the stiffness under servocontrol, although effective, is generally less than the stiffness that may be obtained with braking placed directly on joints, such as the braking used to keep passive setup joints in place. Cable stiffness generally dominates because it is generally less than servosystem or braked joint stiffness.

In some situations, the compliance of the flexible segment may be continuously varied between flaccid and rigid states. For example, locking cable tension can be increased to increase stiffness but without locking the flexible segment in a rigid state. Such intermediate compliance may allow for telesurgical operation while reducing tissue trauma that may occur due to movements caused by reactive forces from the surgical site. Suitable bend sensors incorporated into the flexible segment allow the telesurgical system to determine instrument and/or guide tube position as it bends. U.S. Patent Application Pub. No. US 2006/0013523 (Childers et al.), which is incorporated by reference, discloses a fiber optic position shape sensing device and method. U.S. patent application Ser. No. 11/491,384 (Larkin et al.), which is incorporated by reference, discloses fiber optic bend sensors (e.g., fiber Bragg gratings) used in the control of such segments and flexible devices.

A surgeon's inputs to control aspects of the minimally invasive surgical instrument assemblies, instruments, and end effectors as described herein are generally done using an intuitive, camera referenced control interface. For example, the da Vinci® Surgical System includes a Surgeon's console with such a control interface, which may be modified to control aspects described herein. The surgeon manipulates one or more master manual input mechanisms having, e.g., 6 DOFs to control the slave instrument assembly and instrument. The input mechanisms include a finger-operated grasper to control one or more end effector DOFs (e.g., closing grasping jaws). Intuitive control is provided by orienting the relative positions of the end effectors and the endoscopic imaging system with the positions of the surgeon's input mechanisms and image output display. This orientation allows the surgeon to manipulate the input mechanisms and end effector controls as if viewing the surgical work site in substantially true presence. This teleoperation true presence means that the surgeon views an image from a perspective that appears to be that of an operator directly viewing and working at the surgical site. U.S. Pat. No. 6,671,581 (Niemeyer et al.), which is incorporated by reference, contains further information on camera referenced control in a minimally invasive surgical apparatus.

FIG. 1 is a diagrammatic view of a minimally invasive surgical instrument 1 and its motion. As shown in FIG. 1, surgical instrument 1 is a straight, rigid instrument that is inserted via a small incision 2 into a body cavity (e.g., the abdominal cavity) or lumen 3. Incision 2 is made in a relatively thin body wall tissue structure 4, such as the abdominal wall. A surgeon moves instrument 1 either by hand (e.g., by operating a conventional laparoscopic instrument) or by robotic teleoperation (e.g., using Intuitive Surgical, Inc.'s da Vinci® Surgical System). Since instrument 1 is straight, its movement is partially constrained by incision 2. Instrument 1 may be translated in the direction of its longitudinal axis (inserted or withdrawn) and may be rotated around its longitudinal axis. Instrument 1 also pivots at a center point 5, which is approximately at incision 2, to sweep an end effector 7 through a volume 6. An optional wrist mechanism (not shown) at the distal end of instrument 1 may be used to control end effector 7's orientation. In some situations, however, an intermediate tissue structure (e.g., an organ or vessel, a thick tissue wall 4, a curving body lumen wall, etc.) prevents instrument 1 from pivoting around its center point 5 at incision 2 in some or all directions, which prevents a surgeon from reaching a desired surgical site.

If a minimally invasive surgical instrument is designed to bend between the position at which it enters the patient and the surgical site, then the intermediate tissue structure does not constrain positioning of the instrument's end effector. Such bending may be done in two ways. First, two or more long, rigid body segments are each coupled together by a joint. Second, a flexible mechanism as described above is used. The position of the rigid body segment(s) and the flexible mechanism are actively controlled to position and orient the end effector at the instrument's distal end.

Figure 2A:
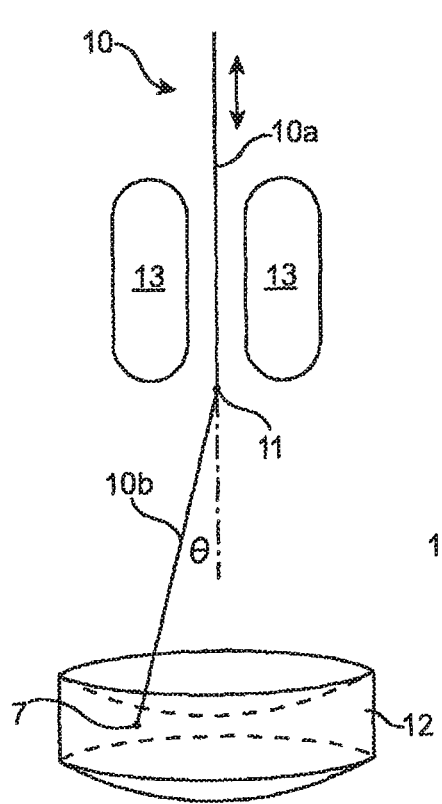
FIG. 2A is a diagrammatic view of another minimally invasive surgical instrument and its motion.

FIG. 2A is a diagrammatic view of another minimally invasive surgical instrument 10 and its motion in accordance with aspects of the invention. As shown in FIG. 2A, instrument 10 includes an illustrative proximal instrument body segment 10a and an illustrative distal instrument body segment 10b. In some aspects, more than two body segments may be used. As depicted, both proximal and distal body segments 10a,10b are straight and rigid. Alternatively, one or both body segments 10a,10b could be curved for a particular path or task. The two body segments 10a,10b are coupled at a joint 11 that allows distal body segment 10b to move. In some aspects joint 11 allows segment 10b to move with a single DOF with reference to segment 10a, and in other aspects joint 11 allows segment 10b to move with two DOFs with reference to segment 10a segment. Instrument 10 can be translated along its longitudinal (insertion) axis. In some aspects, proximal segment 10 can be rolled around its longitudinal axis. Accordingly, end effector 7 positioned at the distal end of distal body segment 10b can be positioned within a volume 12. In some aspects joint 11 provides a single DOF, and so end effector 7 sweeps along a planar curve that rotates as proximal segment 10a rotates around its longitudinal axis. In some aspects joint 11 provides two DOFs, and so end effector 7 sweeps along a curved surface. The height of volume 12 depends on the amount of instrument 10's insertion. Volume 12 is shown as an illustrative cylinder with concave/convex ends. Other volume shapes are possible, depending on the segments and joint motions at instrument 10's distal end. For example, in some aspects distal segment 10b may be displaced by an angle θ from segment 10a' s longitudinal axis that is larger than 90 degrees (this bending back on itself is termed "retroflexive"). An optional wrist mechanism (not shown) may be used to change end effector 7's orientation.

Unlike instrument 1 shown in FIG. 1, instrument 10 is not constrained by a pivot point at a body wall because joint 11 is located deep within the patient. Therefore, instrument 10 can be inserted into a patient past intermediate tissue structures 13 that would otherwise constrain instrument 1's motion (e.g., the esophagus, if gastric surgery is to be performed) or that cannot be disturbed (e.g., brain tissues if neurosurgery is to be performed). Accordingly, aspects of surgical instrument 10 allow a surgeon to reach tissue that cannot be reached or operated upon by using instrument 1. Removing the constraint that the surgical instrument segments be straight and rigid allows even more surgical access to tissue structures.

Figure 2B:
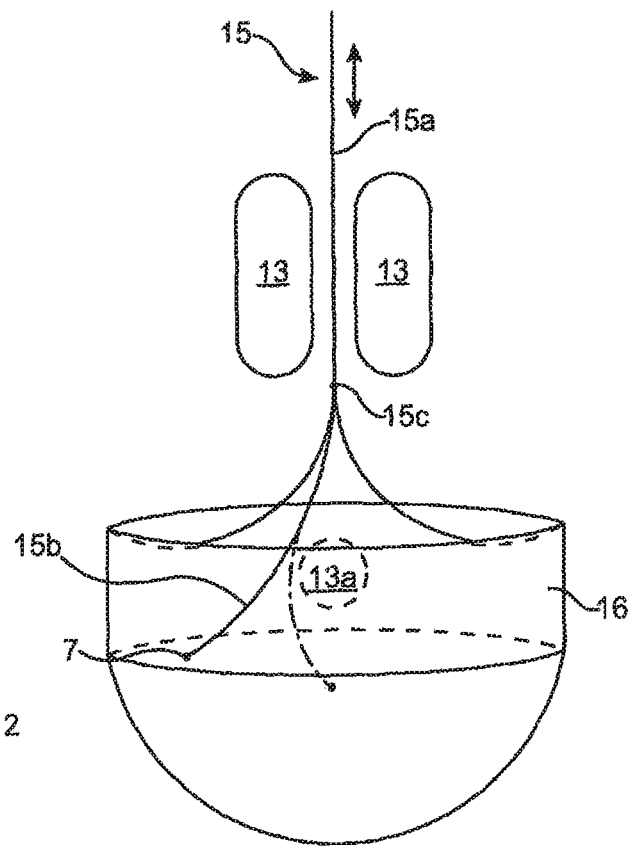
FIG. 2B is a diagrammatic view of yet another minimally invasive surgical instrument and its motion.

Instead of using only rigid instrument body segments, one or more flexible segments may be used. FIG. 2B is a diagrammatic view of another minimally invasive surgical instrument 15 and its motion in accordance with aspects of the invention. As shown in FIG. 2B, surgical instrument 15 has a proximal instrument body segment 15a and a distal instrument body segment 15b. Instead of being straight and rigid, distal body segment 15b is flexible as described above. In some aspects flexible distal segment 15b is coupled to straight (or, alternatively, curved), rigid proximal segment 15a at an intermediate position 15c. In other aspects, both proximal instrument body segment 15a and distal instrument body segment 15b are flexible, and intermediate instrument body position 15c is illustrative of the position at which the two segments are jointed. Instrument body segment 15b is shown with an illustrative simple curve. In other aspects as discussed below body segment 15b may be a compound curve in either two or three dimensions.

During surgery, instrument 15 positions end effector 7 at various positions in illustrative volume 16. Instrument body segment 15a remains constrained by intermediate tissue structures 13 and instrument body segment 15b flexes. Distal segment 15b's length and bend radius determines if instrument 15 can operate retroflexively. It can be seen that compound bending of instrument body segment 15b will allow a surgeon to maneuver around another intermediate tissue structure 13a within volume 16. (A similar action may be performed if instrument 10 (FIG. 2A) has two or more distal segments.) An optional wrist mechanism (not shown) is used to control end effector 7's orientation. In addition, in some aspects if flexible segment 15b is designed to transmit roll, then end effector 7 can be rolled by rolling instrument 15 (either with or without a wrist mechanism).

The surgical instruments 10 and 15 illustrated in FIGS. 2A and 2B are not limited to single instruments. The architectures illustrated by instruments 10 and 15 may be applied to assemblies that combine one or more of various guide tubes, surgical instruments, and guide probes such as those described below. And, one or more imaging systems (endoscopes) may be added to such instruments and instrument assemblies. The aspects described below in association with the figures are illustrative of aspects generally described in FIGS. 2A and 2B. Therefore, aspects of the invention provide multiple telemanipulated surgical instruments, each surgical instrument working independently of the other and each having an end effector with at least six actively controlled DOFs in Cartesian space (i.e., surge, heave, sway, roll, pitch, yaw), via a single entry port in a patient. Further, aspects of the invention provide multiple telemanipulated surgical instruments, each surgical instrument working independently of the other and each having an end effector with at least six actively controlled DOFs in Cartesian space (i.e., surge, heave, sway, roll, pitch, yaw), via a single entry port in a patient and past intermediate tissue that restricts lateral movement of a rigid instrument body. The end effectors' six DOFs in Cartesian space are in addition to DOFs provided by, e.g., moving a guide tube through which the instruments extend to reach a surgical site.

Surgical Instrument Assemblies

Figure 3:
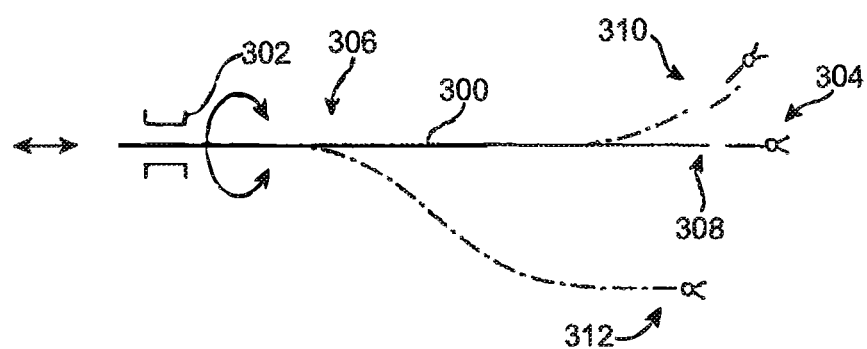
FIG. 3 is a schematic view of a minimally invasive surgical instrument.

FIG. 3 is a schematic view of a minimally invasive surgical instrument 300. Surgical instrument 300 is typically inserted into a patient's body via a cannula 302 or via a natural orifice or incision. An end effector 304 is mounted at the end of instrument 300. In some instances instrument 300's body is passively flexible along its entire length in a manner similar to existing flexible minimally invasive surgical instruments. For example, a cable axially runs through a helical wound wire coil and outer sheath that protects the cable, and the cable translates within the coil to operate the end effector (e.g., a "Bowden" cable). As another example, a series of small, annular vertebra segments may be used to make instrument 300 flexible. In other instances, instrument 300's body may be separated into a proximal segment 306 and a distal segment 308. Each instrument body segment 306,308 may be rigid, passively flexible, or actively flexible. Flexible segments may be made rigid ("rigidizable" or "lockable") in various straight or curved positions. As shown in FIG. 3, for example, proximal segment 306 may be inherently or lockably rigid, and distal segment 308 may be passively or actively flexible. In other instances, both proximal and distal segments 306,308 (essentially the entire segment of instrument 302 that is inside the patient's body) may be passively or actively flexible and rigidizable in various combinations.

The surgical instrument 300 shown in FIG. 3 provides various degrees of freedom for end effector 304. To control end effector 304's position, for example, a combination of instrument 300 insertion and distal segment 308 bending is specified. To control end effector 304's orientation, a combination of instrument 300 roll and distal segment 308 bending is specified. Accordingly, if distal segment 308 can only be placed in a simple curve (as illustrated by alternate position 310), then 4 DOFs are available. If end effector 304 position is specified, then end effector 304 pitch and yaw is a function of the position. If end effector 304 orientation is specified, then the heave and sway position is a function of the orientation. Therefore, a distal wrist mechanism is added to control end effector 304's orientation so that both position and orientation may be specified. If distal segment 308 can be placed in a compound curve (as illustrated by alternate position 312), then 6 DOFs are available, and end effector 304's position and orientation may be specified. Even though end effector 304's position and orientation may be independently specified in such a 6 DOF instrument, a distal wrist mechanism may be added to provide enhanced control over end effector 304's orientation. This enhanced control allows, e.g., a pitch and yaw displacement that is larger than provided by the various poses that distal segment 308 can assume, pitch and yaw displacement while distal segment 308 remains in a particular pose, and pitch and yaw displacement in surgical situations where tissue constrains the shape of distal segment 308's pose.

Figure 4:
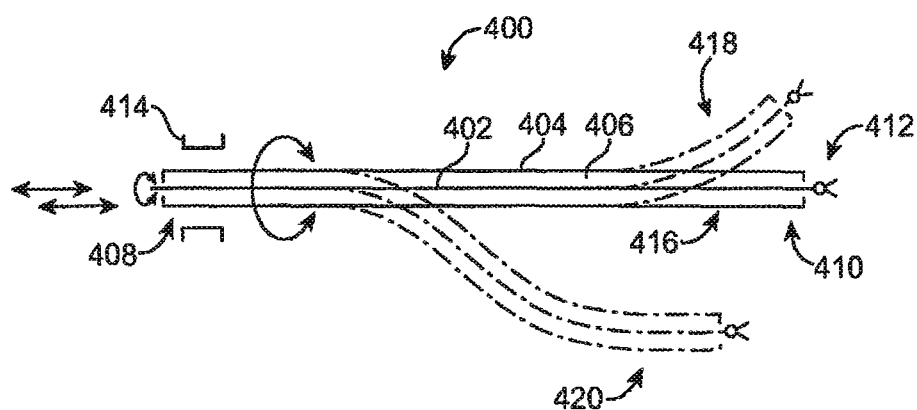
FIG. 4 is a schematic view that illustrates aspects of a minimally invasive surgical instrument assembly.

FIG. 4 is a schematic view that illustrates aspects of a minimally invasive surgical instrument assembly 400. Instrument assembly 400 includes a surgical instrument 402, which may be similar to surgical instrument 300 as described with reference to FIG. 3, and a guide tube 404. Guide tube 404 has at least one longitudinal channel 406, which may be fully or partially enclosed, that runs from proximal end 408 to distal end 410. Surgical instrument 402 runs through channel 406 and may be, for example, snap-fitted into a non-rotating socket to maintain position within guide tube 404. Guide tube 404 may have other channels (not shown) through which, e.g., irrigation or suction may be provided to a surgical site, in addition to channels associated with active control mechanisms (e.g., cables for steering or locking). End effector 412 is coupled to the distal end of surgical instrument 402. Instrument assembly 400 is inserted into a patient via cannula 414 or via natural orifice or incision. In some instances, a cannula-type guide may be used to assist insertion via natural orifice. Cannula 414 and such cannula-type guides may be straight or curved to facilitate insertion (e.g., for laryngeal surgery). Surgical instrument assembly 400's cross section may be circular or other shape (e.g., elliptical, rounded polygon). Various combinations of surgical instrument 402 and guide tube 404 may be rigid, passively flexible, and actively flexible, as well as variably compliant and/or lockable, as described above. In some instances, an optional endoscopic imaging system (not shown) may be at the distal end of guide tube 404.

Just as some or all of surgical instrument 300 (FIG. 3) may be flexed to move its end effector to various positions and orientations, surgical instrument assembly 400 may be similarly flexed to move end effector 412 to various positions and orientations. Distal end segment 416, or the entire length of instrument assembly 400, may be actively flexed to heave and/or sway end effector 412. Combinations of bending and rolling may also be used to displace end effector 412. Compound bends may prevent end effector 412 from pitching and/or yawing during lateral translations as described above. Alternate positions 418 and 420 illustrate these active flexings. In accordance with an aspect of the invention, in some instances distal segment 416 of guide tube 404 provides small, wrist-like pitch and yaw orientation for end effector 412. Other segments of instrument assembly 400 provide end effector roll and position.

Surgical instrument assembly 400 potentially provides more DOFs, some redundant, for end effector 412 than surgical instrument 300 provides for end effector 304, as described with reference to FIG. 3. As shown in FIG. 4, in some aspects surgical instrument 402 may rotate within guide tube 404, and/or guide tube 404 may rotate within cannula 414 (or the natural orifice), to cause end effector 412 to be displaced in roll around instrument assembly 400's longitudinal axis. Instrument 402 may translate within guide tube 404, and/or guide tube 404 may translate within cannula 414, to cause end effector 412 to be displaced (surged) along instrument assembly 400's longitudinal axis. Alternatively, instrument 402 is held in position within guide tube 404 as described below. The lateral bending force that the guide tube's distal segment 416 exerts on the surgical instrument's distal end 402 is sufficiently strong to allow end effector 412 to perform its surgical task. In some instances, end effector 412 may be coupled to the distal end of surgical instrument 402 via a wrist mechanism that provides one or more additional DOFs (e.g., roll, pitch, yaw).

FIG. 4 also illustrates that when a guide tube bends, the bend must not bind operation of an instrument or another guide tube that runs inside it. For instance, guide tube 404 must not bend in such a way that a cable operating end effector 412 is frictionally bound or permanently kinked. In some aspects the radius of curvature is mechanically limited by, e.g., the structure of the individual vertebrae that make up the flexible guide tube. In other aspects the radius of curvature is limited by a control system, described below, to provide, e.g., a smoother behavior during actuation. Further, in some aspects cables for inner instruments or guide tubes must not shift to a shorter path between their proximal and distal ends so that the components they control are not affected as the guide tube bends (such shifting may be compensated for by using distal bend/shape sensors and a control system that maintains proper cable length). Cable path lengths may be stabilized by using sheathes (e.g. Bowden cables) for cables running through the center of the flexible joints or by routing cables through the joint peripheries as described below for virtual pivot point joints.

In some instances surgical instrument 402 is removable and may be replaced with a different surgical instrument that has a structure similar to instrument 402 but a different end effector so as to perform a different surgical task. Accordingly, a single guide tube 404 may be used to provide wrist-like DOFs for one or more interchangeable surgical instruments 402. In some instances the surgical instruments may be interchanged while guide tube 404 remains in the patient. Such interchangability is described in more detail below. The guide tube allows the newly inserted instrument to be positioned directly at the surgical site, regardless of the trajectory. And, one guide tube 404 may be withdrawn and replaced with another during surgery, either with or without an instrument 402 fully or partially inserted. Since some or all of the controllable DOFs are in the guide tube, in some aspects the instrument can be inexpensively made and therefore disposable, and the guide tube can be made sterilizable and reusable.

Figure 4A:
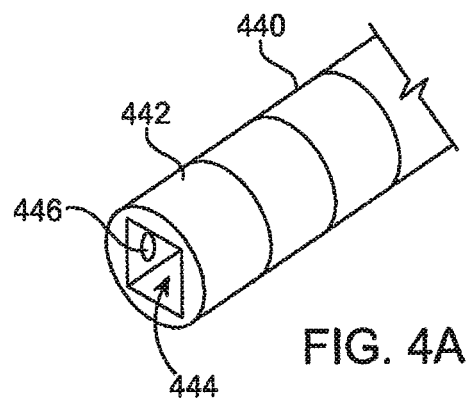
FIGS. 4A and 4B are diagrammatic perspective views that illustrate aspects of a removable instrument that is held in place within guide tube.
Figure 4B:
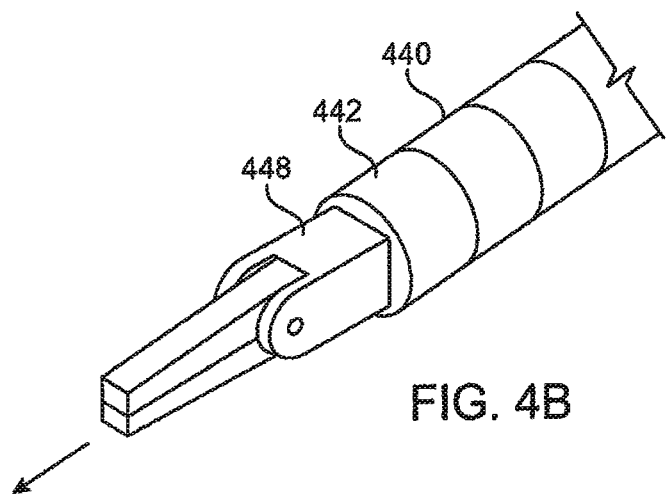

FIGS. 4A and 4B are diagrammatic perspective views that illustrate aspects of a removable instrument that is held in place within guide tube 440. The distal end 442 of guide tube 440 has an opening 444 though which the distal end of the instrument passes. Opening 444 is optionally made non-round to prevent the instrument from rolling within guide tube 440. An optional fitting 446 (e.g., a spring that snaps into a detent, etc.) holds the instrument's end effector 448 in position to keep the instrument from translating through the guide tube. A round opening 444 allows the instrument to roll while fitting 446 keeps the instrument from translating. When the fitting 446 releases the instrument (e.g., when sufficient pulling force is applied), the instrument may be withdrawn from the guide tube. Distal end 442 may be a wrist mechanism for the instrument's end effector in some aspects. The roll prevention configuration and the fitting are illustratively shown at the distal end of the guide tube but may be placed at various positions (e.g., at the insertion end of the guide tube). The roll prevention configuration and the fitting can be used in the various aspects described below for other instrument and guide tube combinations, with the understanding that the roll preventing configuration and the fitting will remove a redundant insertion DOF and/or a redundant roll DOF.

Instrument assembly 400 may be inserted in a rigidized or locked state, or it may be actively steered during insertion in order to reach a target surgical site. In some aspects instrument 402 and guide tube 404 are alternatively coaxially advanced. For example, instrument 402 is actively steered part way along the trajectory to the surgical site and then locked (only the distal section of the instrument (or guide tube) need be actively steerable; the more proximal sections may be passive or may use curve propagation as the instrument (or guide tube) advances). Curve propagation is disclosed in, e.g., Ikuta, K. et al., "Shape memory alloy servo actuator system with electric resistance feedback and application for active endoscope," 1988 IEEE International Conference on Robotics and Automation, Apr. 24-29, 1988, Vol. 1, pages 427-430, which is incorporated by reference. Guide tube 404 is then passively advanced to the distal end of instrument 402 and locked to support further advancement of instrument 402. The coaxial alternating advancing and locking continues until the surgical site is reached along the desired trajectory. Alternatively, guide tube 404 is actively steerable and lockable, and instrument 402 is passively advanced and locked within guide tube until the surgical site is reached. If both surgical instrument 402 and guide tube 404 are actively steerable, then they may "leapfrog" each other as they coaxially advance and lock along the trajectory to the surgical site. Such coaxial insertion may also be used with any combination of two or more instruments and guide tubes described herein.

Figure 5:
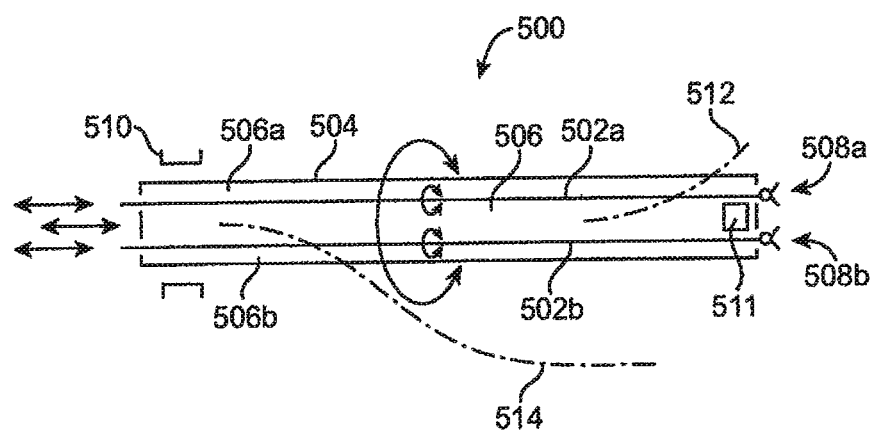
FIG. 5 is a schematic view that illustrates aspects of a second minimally invasive surgical instrument assembly.

FIG. 5 is a schematic view that illustrates aspects of a second minimally invasive surgical instrument assembly 500. Surgical instrument assembly 500 illustrates that two or more surgical instruments 502a,502b may be surrounded by a single guide tube 504. Surgical instruments 502a,502b may run longitudinally through guide tube 504 in a single channel 506. Or, surgical instruments 502a,502b may each run through guide tube 504 in unique, individual channels 506a,506b. End effectors 508a,508b are each coupled to the distal ends of instruments 502a,502b. Instrument assembly 500 is inserted via cannula 510 and as described above. Instrument assembly 500's cross section may be circular, elliptical, or other shape (e.g., rounded rectangle or other polygon). Various combinations of surgical instruments 502a,502b and guide tube 504 may be rigid, passively flexible, and actively flexible, as well as lockable, as described above. An illustrative optional imaging system 511 (e.g., one or more image capture chips with associated optics and electronics) is positioned at the distal end of guide tube 504. The imaging system 511 has a field of view that may be used to assist advancing guide tube 504 and that allows a surgeon to view end effectors 508a,508b working at a surgical site.

Surgical instrument assembly 500 operates in a manner similar to that of surgical instrument assembly 400 (FIG. 4), except that it is illustrative of aspects in which two or more surgical instruments extend through a single guide tube from a proximal to a distal end. Accordingly, the descriptions above of additional channels, active and passive flexibility, locking/rigidizing, various DOFs, the optional use of wrist mechanisms, instrument interchangeability, alternating coaxial advancing, and cannulas apply to instrument assembly 500. Distal end segment and entire assembly flexibility are illustrated by alternate position lines 512 and 514, similar to those shown in the preceding figures as described above. Compound bending of guide tube 504 provides at least 6 DOFs for end effectors 508a,508b as described above. Alternating coaxial advancement may done as described above. Various ways of such advancing are possible. For example, in some aspects both instruments may be used and the guide tube slides over both instruments; in other aspects first one instrument is advanced and locked, then the guide tube is advanced and locked, then the other instrument is advanced and locked, etc.

Figure 6:
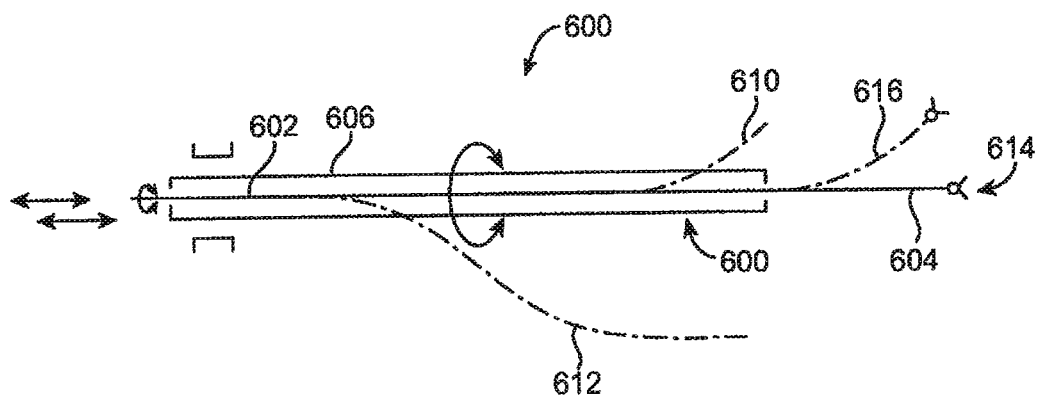
FIG. 6 is a schematic view that illustrates aspects of a third minimally invasive surgical instrument assembly.

FIG. 6 is a schematic view that illustrates aspects of a third minimally invasive surgical instrument assembly 600. Surgical instrument assembly 600 operates in a manner similar to that of surgical instrument assembly 400 (FIG. 4), except that it is illustrative of aspects in which a surgical instrument 602's actively flexible distal segment 604 extends beyond the distal end of guide tube 606. Active flexibility of guide tube 606's distal end segment 608 and/or of the entire guide tube 606 are illustrated by alternate position lines 610 and 612. Active flexibility of instrument 602's distal segment 604 moves end effector 614 to illustrative alternate position 616. Accordingly, end effector 614 experiences wrist-like DOFs (e.g., roll, pitch, yaw) from the movement of instrument 602's distal segment 604, from the movement of guide tube 606's distal segment 608, and/or from a combination of movements by distal segments 604, 608. Thus, instrument assembly 600 illustrates aspects in which combinations of instruments and guide tubes provide redundant position and orientation DOFs for end effector 614. The descriptions above of additional channels, active and passive flexibility, locking/rigidizing, various degrees of freedom, increased lateral force application and stiffness, the optional use of wrist mechanisms and imaging systems, instrument interchangeability, alternating coaxial advancing, and cannulas apply to instrument assembly 600.

Figure 7:
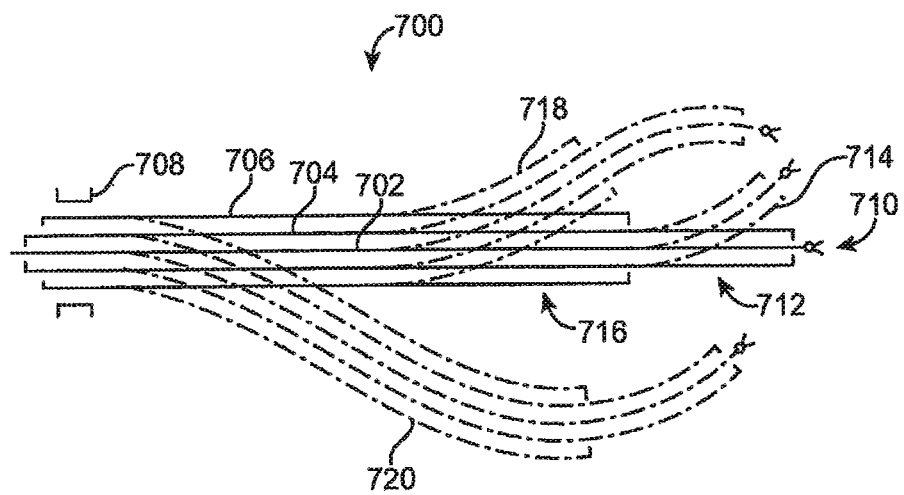
FIG. 7 is a schematic view that illustrates aspects of a fourth minimally invasive surgical instrument assembly.

FIG. 7 is a schematic view that illustrates aspects of a fourth minimally invasive surgical instrument assembly 700. As shown in FIG. 7, surgical instrument 702 extends through primary guide tube 704 along instrument assembly 700's longitudinal axis. In addition, primary guide tube 704 extends through secondary guide tube 706 along the longitudinal axis. In some instances surgical instrument assembly 700 is inserted via a cannula 708. End effector 710 is coupled to the distal end of surgical instrument 702 so that it extends just beyond primary guide tube 704's distal end.

End effector 710's redundant DOFs, other than the inherent one or more DOFs associated with its specific task (e.g., gripping), are provided in various ways. Surgical instrument 702 may rotate within primary guide tube 704, and/or primary guide tube 704 may rotate within secondary guide tube 706, and/or secondary guide tube 706 may rotate within cannula 708 (or a natural orifice or incision), which causes end effector 710 to be displaced in roll around instrument assembly 700's longitudinal axis. Surgical instrument 702 may translate within primary guide tube 704, and/or primary guide tube 704 may translate within secondary guide tube 706, and/or secondary guide tube 706 may translate within cannula 708, to displace (surge) end effector 710 along instrument assembly 700's longitudinal axis.

As shown in FIG. 7, an actively flexible distal segment 712 of primary guide tube 704 extends beyond secondary guide tube 706's distal end. Distal segment 712 may cause end effector 710 to be heaved and/or swayed (with incidental pitch and yaw as discussed above), adding one or two additional degrees of freedom as illustrated by alternate position 714. Similarly, an actively flexible distal segment 716 of secondary guide tube 706, or the entire secondary guide tube 706, may cause end effector 710 to be heaved and/or swayed, adding one or two more degrees of freedom as illustrated by alternate positions 718 and 720. Since instrument assembly 700 provides various combinations of roll, heave, and sway displacements for end effector 710, a wrist-type mechanism may not be required to couple end effector 710 to surgical instrument 702, although such a mechanism may be used to provide an additional one or more degrees of freedom (e.g., roll, pitch, yaw).

As indicated by the alternate position lines in FIG. 7, the primary and secondary guide tubes can maneuver end effector 710 with various combinations of simple and compound bends. In one illustrative embodiment, secondary guide tube 702's active flexibility is used for relatively large movements of end effector 710, and primary guide tube distal segment 712's active flexibility is used for relatively small, wrist-type movements of end effector 710. The amount of such motion depends on the distance that distal segment 712 extends beyond secondary guide tube 706, and so may provide motion similar to that described in FIG. 2B.

In some instances surgical instrument 702 may extend beyond primary guide tube 704 as described in FIG. 6. The descriptions above of additional channels, active and passive flexibility, locking/rigidizing, various DOFs, increased lateral force application and stiffness, instrument interchangeability, alternating coaxial advancing, and cannulas apply to instrument assembly 700. In addition, since secondary guide tube 706 has an even greater outer diameter than primary guide tube 704, actuation and locking mechanisms for secondary guide tube 706 may provide an increased lateral force and stiffness against reaction forces than either instrument 702 or primary guide tube 704 may provide alone or together.

Figure 8:
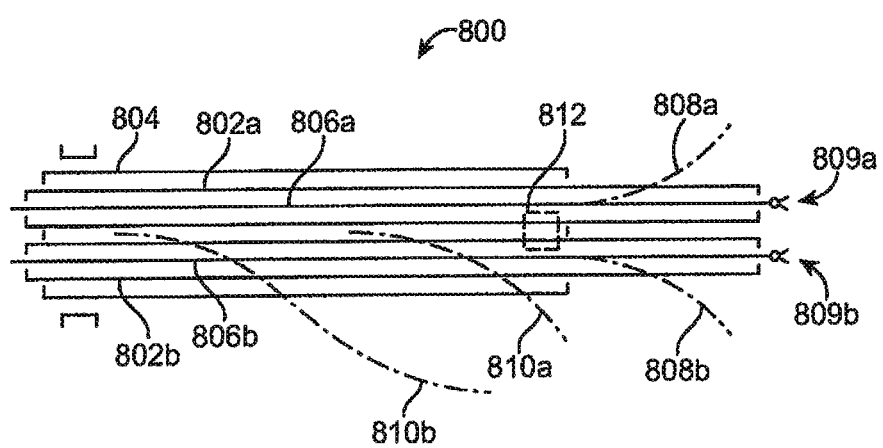
FIG. 8 is a schematic view that illustrates aspects of a fifth minimally invasive surgical instrument assembly.

FIG. 8 is a schematic view that illustrates aspects of a fifth minimally invasive surgical instrument assembly 800. Surgical instrument assembly 800 illustrates that two or more primary guide tubes 802a,802b may be surrounded by a single secondary guide tube 804. An illustrative surgical instrument 806a,806b runs though each of primary guide tubes 802a,802b. The primary guide tubes 802a,802b have an architecture generally similar to surgical instrument assembly 400 (FIG. 4). In some instances, however, one or more primary guide tubes 802 may have an architecture similar to surgical instrument assembly 500 (FIG. 5) or surgical instrument assembly 600 (FIG. 6). Active flexibility of the distal segments of primary guide tubes 802a,802b that extend beyond the distal end of secondary guide tube 804 are illustrated by alternate position lines 808a,808b. The distal segments of primary guide tubes 802a,802b can move end effectors 809a,809b adjacent one another at various positions at a surgical site within a patient so as to perform various surgical tasks. Various active flexibilities of secondary guide tube 804 are illustrated by alternate position lines 810a,810b. The descriptions above of additional channels, active and passive flexibility, locking/rigidizing, various DOFs, increased lateral force application and stiffness, the optional use of wrist mechanisms, instrument interchangeability, alternating coaxial advancing, and cannulas apply to instrument assembly 800.

In some instances an endoscopic imaging system 812, represented schematically by a dashed box, is positioned at secondary guide tube 804's distal end. Imaging system 812 may be mono- or stereoscopic as described above and may have a viewing angle aligned with or angled (e.g., 30 degrees) from instrument assembly 800's longitudinal axis. In some instances imaging system 812 is positioned between primary guide tubes 802a,802b. In other instances imaging system 812 is positioned above, below, or to the side of primary guide tubes 802a,802b to make secondary guide tube 804's cross section more compact (e.g., one stereoscopic lens window above and one below the primary guide tubes 802a,802b; camera referenced control for this configuration is made possible if the primary guide tubes bend out and then inwards towards the surgical site roughly coplanar with the interpupillary axis).

Figure 9:
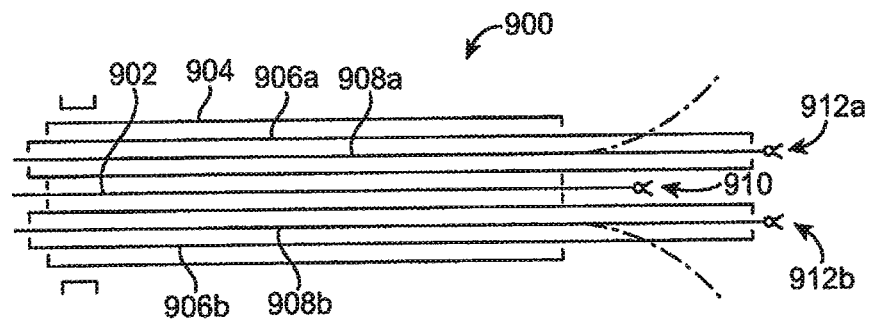
FIG. 9 is a schematic view that illustrates aspects of a sixth minimally invasive surgical instrument assembly.

FIG. 9 is a schematic view that illustrates aspects of a sixth minimally invasive surgical instrument assembly 900. Instrument assembly 900 is similar to instrument assembly 800 (FIG. 8), except that an illustrative additional surgical instrument 902 extends through secondary guide tube 904, but surgical instrument 902 is not surrounded by a primary guide tube. Accordingly, the relationship between surgical instrument 902 and secondary guide tube 904 is similar to that described between the surgical instruments and guide tubes as shown in FIGS. 4 and 6. The relationship between the primary guide tube 906a,906b and instrument 908a,908b assemblies is similar to that described for aspects illustrated by FIGS. 7 and 8. Instrument assembly 900 is illustrative of a secondary guide tube through which extend various combinations of one or more primary guide tube and instrument assemblies as well as one or more instruments without guide tubes.

In some instances surgical instrument 902 is rigid or passively flexible and its end effector 910 is used to grasp and pull tissue to assist the surgical tasks that end effectors 912a,912b at the ends of instruments 908a,908b perform. Although rigid or passively flexible, instrument 902 is capable of pulling with considerable force. In other instances surgical instrument may perform other functions, such as retraction, irrigation, suction, etc. Further, if an endoscopic imaging system is placed at the distal end of secondary guide tube 904, as illustrated by instrument assembly 800 (FIG. 8), then instrument 902 may be used to service (e.g., clean with a jet of fluid) the imaging system's window(s).

Figure 9A:
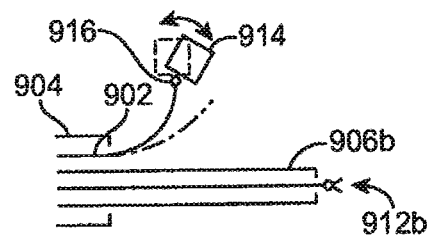
FIG. 9A is a schematic view that illustrates a detail of an alternate aspect of FIG. 9.

In still other instances, as mentioned above, surgical instrument 902's distal end is actively flexible, and end effector 910 is replaced by an endoscopic imaging system 914 as shown in FIG. 9A. In these instances a distal imaging device may be coupled to the actively flexible end of surgical instrument 902 with a wrist-type mechanism 916 that provides at least a DOF in pitch. Such an architecture allows the image sensing device to be moved out from between the distal ends of primary guide tubes 906a,906b and then the viewing angle is pitched (and/or yawed) to align the center of the visual field with the area at which the end effectors 912a,912b are working. This architecture enables a surgeon to work, at a surgical site via a single entry port into the body, with two independently actuated surgical end effectors and an endoscopic imaging system that is independent of the surgical instruments. Another benefit of the independently controlled imaging system illustrated in FIG. 9A is tissue retraction, as shown and described more fully with reference to FIG. 17A below.

Figure 10:
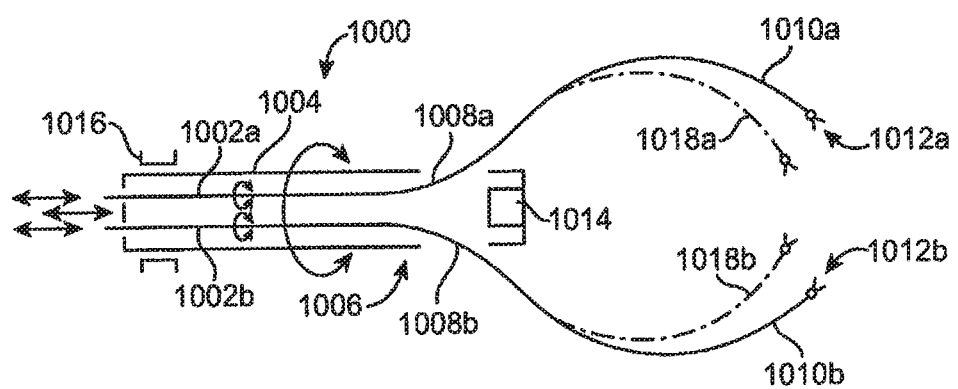
FIG. 10 is a schematic view that illustrates aspects of a seventh minimally invasive surgical assembly.

In accordance with aspects described above, one or more surgical instruments exit at the distal end of an guide tube, which may be a flat face or other shape, square or inclined to the assembly's longitudinal axis. In accordance with other aspects, one or more surgical instruments exit from the side of a guide tube. FIG. 10 is a schematic view that illustrates such aspects in a seventh minimally invasive surgical assembly 1000.

As shown in FIG. 10, two surgical instruments 1002a, 1002b (illustrative of two or more instruments) extend longitudinally through guide tube 1004. Instruments 1002a, 1002b exit guide tube 1004's distal segment 1006 via side exit ports 1008a,1008b instead of at guide tube 1004's extreme distal end. The side exit ports 1008a,1008b may be oriented to be generally opposite each other (i.e., displaced approximately 180 degrees from each other) or they may be separated by a lesser angle (e.g., 120 degrees). And, the side exit ports may have various angular orientations around distal segment 1006 in aspects in which more than two exit ports are used for one, two, or more than two instruments 1002. In one aspect, one side exit port is farther from guide tube 104's distal tip than another side exit port. Instrument 1002a's distal segment 1010a and instrument 1002b's distal segment 1010b are each independently actively flexible so as to move end effectors 1012a,1012b for work at a surgical site. Various combinations of simple or compound bending with instrument roll and insertion, along with optional wrist mechanisms, provide the required end effector DOFs. An endoscopic imaging system 1014 is positioned at the distal end of guide tube 1004. Imaging system 1014's viewing angle may be aligned with instrument assembly 1000's longitudinal axis, or the viewing angle may be angled (e.g., 30 degrees) from the longitudinal axis. In some aspects the viewing angle may be actively changed during a surgical procedure using, e.g., one or move movable reflecting surfaces (mirrors, prisms). The descriptions above of additional channels, active and passive flexibility, locking/rigidizing, various DOFS, increased lateral force and stiffness, the optional use of wrist mechanisms, instrument interchangeability, and cannulas apply to instrument assembly 1000.

Surgical assembly 1000 is inserted into a patient via incision or natural orifice, in some instances through cannula 1016 or a similar guiding structure as described above. As guide tube 1004 is inserted, in some instances surgical instruments 1002a,1002b are either fully or partly retracted so that they do not extend beyond openings 1008a,1008b as guide tube 1004 advances towards a surgical site. Images from imaging system 1014 may assist advancement. Once guide tube 1004 is in position at the surgical site, instruments 1002a,1002b may then be inserted and/or advanced within guide tube 1004 to reach the surgical site. Guide tube 1004 may be actively flexed during a surgical procedure to provide gross movements at the surgical site while instrument distal segments 1010a,1010b perform fine movements to complete the surgical task, as illustrated by alternate position lines 1018a,1018b. The surgeon views images from imaging system 1014 while performing surgical tasks with end effectors 1012a,1012b. Since the surgeon cannot see images from imaging system 1014 of distal segments 1010a, 1010b as they exit side ports 1008a,1008b, in some aspects a control system, described below, controls distal segments 1010a,1010b as they exit from guide tube 1004 so that they curve to meet in front of imaging system 1014. In other aspects, a luminal space is mapped as described below, and the control system uses the mapping data to guide the end effectors into imaging system 1014's field of view. In still other aspects the distal end of the guide tube may be moved, e.g., to the left from a known space, thereby allowing the right instrument to be inserted into the "safe" space to the right of the guide tube. Then, likewise, the distal end of guide tube is moved to the right and the left instrument is moved into the "safe" space to the left of the guide tube. For aspects in which the distal end of the guide tube moves upward independently of the part of the guide tube at which the instruments exit, the instruments may be similarly inserted into the "safe" space underneath the upwardly displaced distal end of the guide tube. For withdrawal, or subsequent large repositioning, instruments 1002a,1002b may be withdrawn through side exit ports 1008a,1008b, either partially into or entirely from guide tube 1004.

Figure 11:
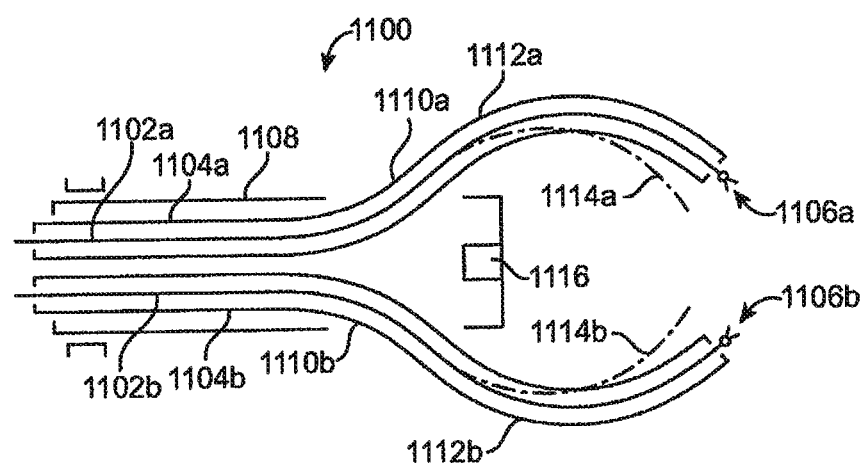
FIG. 11 is a schematic view that illustrates aspects of an eighth minimally invasive surgical assembly.

FIG. 11 is a schematic view that illustrates aspects of an eighth minimally invasive surgical assembly 1100. As shown in FIG. 11, surgical instrument 1102a extends through primary guide tube 1104a along its longitudinal axis. Likewise, surgical instrument 1102b extends through primary guide tube 1104b along its longitudinal axis. End effectors 1106a,1106b are coupled to the distal ends of instruments 1102a,1102b. Primary guide tubes 1104a,1104b extend longitudinally through secondary guide tube 1108. In a manner similar to the way surgical instruments 1002a, 1002b exit side ports 1008a,1008b of guide tube 1004's distal segment 1106, primary guide tubes 1104a,1104b exit side ports 1110a,1110b of secondary guide tube 1108. The distal segments 1112a,1112b of primary guide tubes 1104a, 1104b actively flex to move end effectors 1106a,1106b, as illustrated by alternate position lines 1114a,1114b. An endoscopic imaging system 1116 is positioned at secondary guide tube 1108's distal end. The descriptions above of additional channels, active and passive flexibility, locking/rigidizing, various DOFs, increased lateral force application and stiffness, the optional use of wrist mechanisms, instrument interchangeability, cannulas, and endoscopic imaging systems apply to instrument assembly 1100.

Instrument assembly 1100 operates in a manner similar to instrument assembly 1000 (FIG. 10). The principal difference between the two aspects is the use of both secondary and primary guide tubes in assembly 1100. The relationship between instrument assemblies 1100 and 1000 is therefore akin to the relationship between instrument assemblies 800 (FIG. 8) and 500 (FIG. 5). The descriptions above of insertion, full or partial instrument retraction during insertion and repositioning, use of the imaging system, use of primary and secondary guide tubes, and controlled extension of instruments apply to aspects of instrument assembly 1100.

FIGS. 11A and 11B are diagrammatic end views of surgical instrument assemblies, and they illustrate that a side-exit assembly such as assemblies 1000 (FIG. 10) and 1100 (FIG. 11) may be used to reduce the overall cross-sectional area of a guide tube or secondary guide tube. FIG. 11A is an illustrative view of an assembly, such as assembly 800 (the circular cross-sectional shape is merely illustrative), in which instrument/guide tube combinations 802a, 806a and 802b,806b exit from the distal end of a guide tube or secondary guide tube. In this illustrative example, imaging system 812 is a stereoscopic imaging system with an interpupillary distance 1120 between imaging ports and an illustrative illumination port 1122. As shown in FIG. 11B's illustrative example, the side-exit assembly's instrument/ distal guide tube segment combinations 1102a,1112a and 1102b,1112b have the same cross-sectional dimensions as combinations 802a,806a and 802b,806b shown in FIG. 11A. And, illustrative stereoscopic imaging system 1116 has the same interpupillary distance 1120 as imaging system 812 as shown in FIG. 11A. If the endoscopic image is captured and digitized at the distal end of the guide tube, then the guide tube area proximal of the image capture and digitizing components can be used for instruments and actuation instead of for optics (e.g., fiber bundles, rod lenses, etc.). Consequently, the oblong-shaped cross-sectional area of FIG. 11B's side-exit guide tube is smaller than the cross-sectional area of FIG. 11A's end-exit guide tube, and the imaging system's interpupillary distance is the same. This reduced cross-sectional area may be an advantage for, e.g., the size and location of an incision to be used, for the size of a particular natural orifice, or for the position of intermediate tissue between the entry port and the surgical site. Such an oblong cross-sectional shape can be used in other instrument assembly guide tubes described herein.

Figure 12:
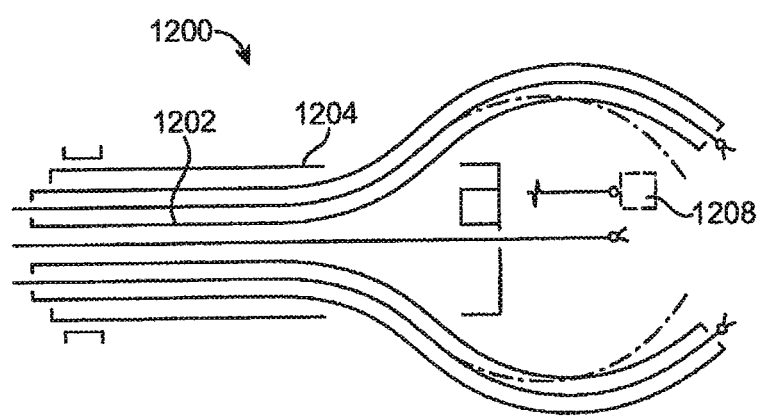
FIG. 12 is a schematic view that illustrates aspects of a ninth minimally invasive surgical instrument assembly.

FIG. 12 is a schematic view that illustrates aspects of a ninth minimally invasive surgical instrument assembly 1200. Instrument assembly 1200 is similar to instrument assembly 1100, with an additional surgical instrument 1202 that extends from the distal end of secondary guide tube 1204. Surgical instrument 1202 operates in a manner similar to surgical instrument 902 (FIG. 9), being in some aspects rigid and in others passively or actively flexible as described above. And, end effector 1206 may be replaced with an endoscopic imaging system as described with reference to FIGS. 9 and 9A or FIGS. 17 and 17A so that in some aspects instrument assembly 1200 has an independently operated, optionally wrist-mounted, endoscopic imaging system 1208 as illustrated in FIG. 12.

FIGS. 12A and 12B are diagrammatic views of embodiments that illustrate retroflexive positions in examples of side-exit guide tubes, similar to retroflexive movement for end-exit guide tubes discussed above. FIG. 12A illustrates that in one aspect the side-exit instrument assembly 1220 actively bends in a plane that is approximately coplanar with the side exit ports 1222a and 1222b (yaw with reference to the visual field reference). FIG. 12B illustrates that in another aspect the side exit instrument assembly 1230 actively bends in a plane that is approximately perpendicular to the side exit ports 1232a and 1232b (hidden) (pitch with reference to the visual field reference). Assembly 1230's bend radius may be smaller than assembly 1220's bend radius, other dimensions being substantially the same, due to the mechanical structure. In some aspects the side-exit instrument assembly may simultaneously yaw and pitch, and the assembly may yaw/pitch distally of the side exit ports.

Figure 13:
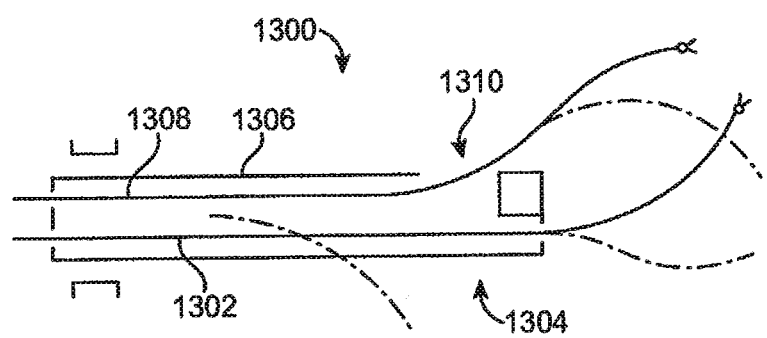
FIG. 13 is a schematic view that illustrates aspects of a tenth minimally invasive surgical instrument assembly.
Figure 14:
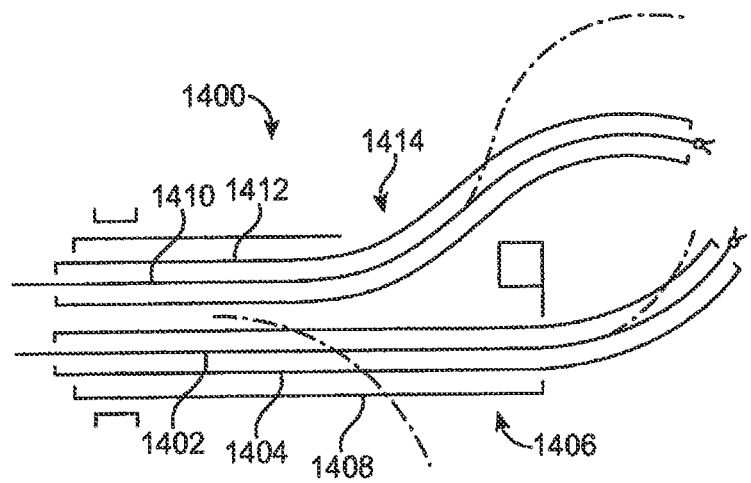
FIG. 14 is a schematic view that illustrates aspects of an eleventh minimally invasive surgical instrument assembly.

FIGS. 13 and 14 are schematic views that illustrate tenth and eleventh aspects of minimally invasive surgical instrument assemblies 1300 (FIG. 13) and 1400 (FIG. 1400). Surgical instrument assemblies 1300 and 1400 combine aspects of surgical instrument assemblies illustrated in FIGS. 3-12B and the associated descriptions. Specifically, instrument assembly 1300 illustrates aspects in which one or more surgical instruments 1302 exit the end of a distal segment 1304 of a guide tube 1306, and one or more other surgical instruments 1308 exit from a side exit port 1310 at guide tube 1306's distal segment 1304. Likewise, instrument assembly 1400 illustrates aspects in which one or more surgical instruments 1402 run coaxially within one or more primary guide tubes 1404 that exit the end of a distal segment 1406 of a secondary guide tube 1408, and one or more other surgical instruments 1410 run coaxially through one or more other primary guide tubes 1412 that run coaxially within secondary guide tube 1408 and exit from one or more side exit ports 1414 at secondary guide tube 1408's distal segment 1406. The descriptions above of additional channels, active and passive flexibility, locking/rigidizing, various DOFs, increased lateral force application and stiffness, the optional use of wrist mechanisms, instrument interchangeability, cannulas, and endoscopic imaging systems apply to instrument assemblies 1300 and 1400.

In many instances an instrument or instrument assembly as described herein can be actively or passively positioned at a surgical site. A sufficiently flexible and maneuverable surgical instrument or surgical instrument assembly, such as those described herein, may be inserted with one or more segments of the instrument or assembly functioning in accordance with the insertion description below. In some instances, however, a guide probe can be used to initially define some or all of the trajectory between the entry port and the surgical site. The guide probe may be maneuvered using, e.g., image data from an imaging system at the guide probe's distal tip, real time image data from an external imaging system (e.g., ultrasound, fluoroscopy, MRI), preoperative image data and computer analysis of likely trajectory, and various combinations of these data.

Figure 15A:
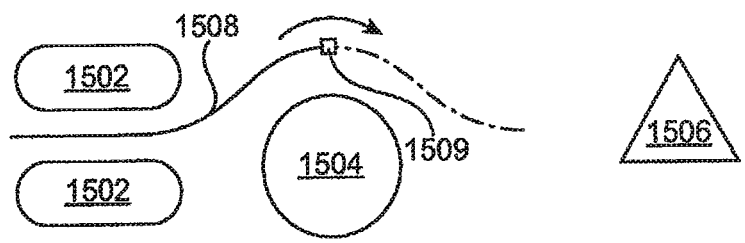
FIGS. 15A-15D are schematic views that illustrate aspects of inserting a flexible, steerable surgical instrument and surgical instrument assembly.

FIGS. 15A-15D are schematic views that illustrate aspects of inserting a flexible, steerable surgical instrument and surgical instrument assembly, such as those described herein, by using a guide probe to maneuver past intermediate tissue structures so as to reach a surgical site within a patient. Insertion may be via natural orifice or incision, either with or without using a cannula (not shown) as described above. As shown in FIG. 15A, a first intermediate tissue structure 1502 prevents a surgical instrument or surgical instrument assembly from operating with a pivoting center point generally where it enters the body, as shown in FIG. 1. In addition, a second intermediate tissue structure 1504 exists between the position where the instrument or instrument assembly passes the first intermediate tissue structure 1502 and the target surgical site 1506, as shown in FIG. 2B. An instrument or instrument assembly must be guided between and around the intermediate tissue structures to reach the surgical site.

Figure 15B:
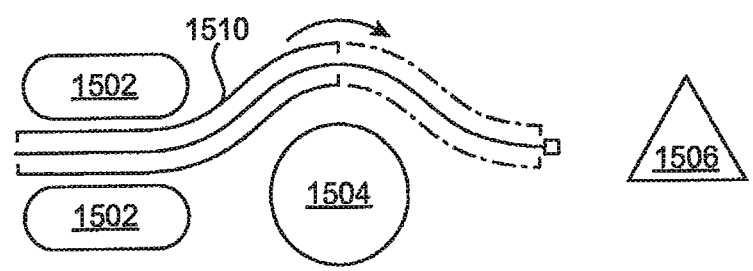
Figure 15C:
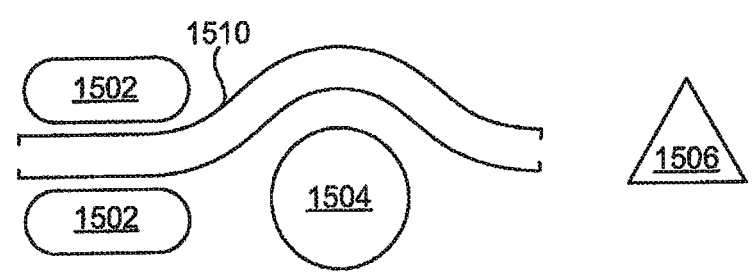
Figure 15D:
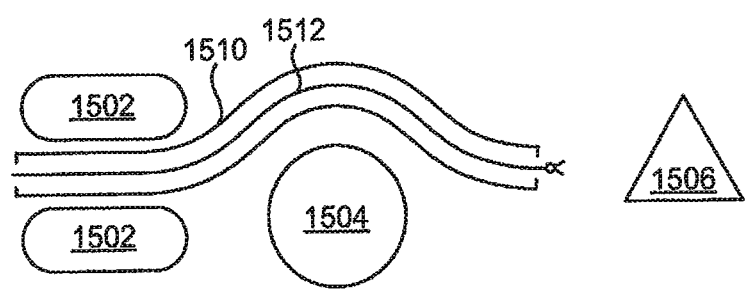

As shown in FIG. 15A, in one aspect a guide probe 1508 is inserted past first intermediate structure 1502 and is then actively maneuvered around second intermediate tissue structure 1504 to reach surgical site 1506 or another desired position. The guide probe's primary function is to establish a trajectory to the surgical site. An optional endoscopic imaging system 1509 may be mounted at guide probe 1508's distal tip. In some aspects curve propagation as described above is used during insertion—curves initially formed by steering the distal end are automatically propagated in a proximal direction on the guide probe as it is advanced towards the surgical site. Such curve propagation is done using, e.g., control systems as described below. Once at its desired position, guide probe 1508 is then rigidized so as to maintain its two- or three-dimensional curved shape. Next, a guide tube 1510 is inserted coaxially over guide probe 1508, as shown in FIG. 15B. The guide tube 1510 may be inserted to an intermediate position as shown, or it may be inserted and maneuvered to a position at surgical site 1506 as shown by the alternate position lines. In some aspects, the guide probe and guide tube may be coaxially inserted, first one, then the other in a repeated, alternating way. Guide tube 1510 is illustrative of various primary and secondary guide tubes, such as those shown in FIGS. 4-14. Once in a desired position, guide tube 1510 is then rigidized to maintain the shape defined by guide probe 1508, which is then withdrawn as shown in FIG. 15C. After the guide probe is withdrawn, a surgical instrument or surgical instrument assembly 1512 may then be inserted through guide tube 1510 to reach surgical site 1506, as shown in FIG. 15D.

To facilitate guide tube insertion, in one aspect the guide probe extends beyond the coaxial guide tube by a distance sufficient to allow the guide probe to enter a patient and reach the surgical site. Then, the guide probe is coaxially inserted. In an alternate aspect, a proximal portion (e.g., the transmission mechanism; see FIG. 27 for an illustrative view) of the guide probe is removable to allow the guide tube to be coaxially inserted over the guide probe.

As an illustrative example in accordance with surgical instrument assembly 400 (FIG. 4), a guide probe is inserted, guide tube 404 is inserted over the guide probe, the guide probe is withdrawn, and then surgical instrument 402 is inserted through guide tube 404. A similar procedure can be used for guide tubes with multiple instrument channels, such as surgical instrument assembly 500 (FIG. 5). As another illustrative example in accordance with surgical instrument assembly 700 (FIG. 7), a guide probe is inserted, primary guide tube 704 is inserted over the guide probe, secondary guide tube 706 is inserted over primary guide tube 704, the guide probe is withdrawn, and instrument 702 is inserted through primary guide tube 704. Alternately, a guide probe having a relatively larger outer diameter is inserted, secondary guide tube 706 is inserted over the guide probe, the guide probe is withdrawn, and primary guide tube 704 and instrument 706 are then inserted through secondary guide tube 706. A similar procedure can be used for secondary guide tubes that have two or more primary guide tube and/or instrument channels. As yet another illustrative example, guide tube 1510 is analogous to cannula 708, and instrument assembly 700 is inserted through guide tube 1510. Many variations in insertion order are possible and are within the scope of the invention.

Referring again to FIG. 2A, it can be seen that a rigid distal segment of a minimally invasive surgical instrument can also provide access to a large volume deep within the body that is accessed through an intermediate tissue structure. Such mechanisms may be mechanically simpler to build and operate, and therefore may be less expensive and easier to control than systems that use flexible technology. And, in some aspects such mechanisms may work back on themselves to provide a capability similar to the retroflexive bending described above.

Figure 16:
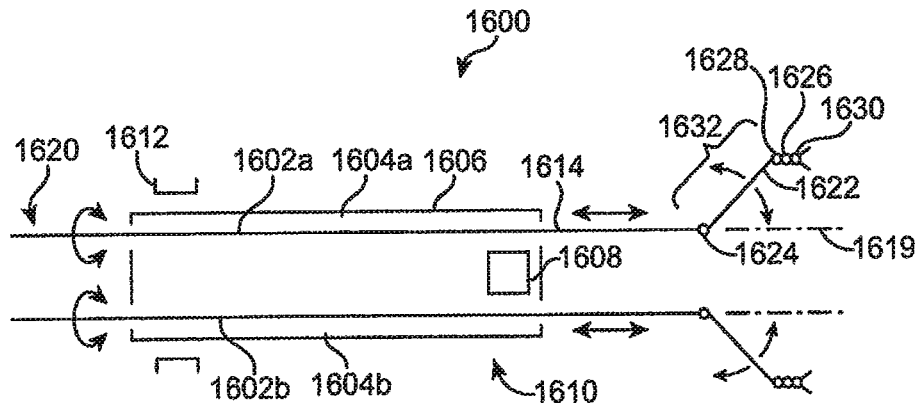
FIG. 16 is a schematic view that illustrates a twelfth aspect of a minimally invasive surgical instrument assembly.

FIG. 16 is a schematic view that illustrates aspects of a twelfth minimally invasive surgical instrument assembly 1600. As shown in FIG. 16, two surgical instruments 1602a, 1602b extend through channels 1604a,1604b that extend longitudinally through rigid guide tube 1606. In some aspects guide tube 1606 is straight and in others it is curved to accommodate a particular insertion port (the instruments are similarly curved to facilitate insertion). Guide tube 1606 may have various cross-sectional shapes (e.g., circular, oval, rounded polygon), and various numbers of surgical instruments and channels may be used. Some optional working channels may be used to provide supporting surgical functions such as irrigation and suction. In some aspects an endoscopic imaging system (e.g., mono- or stereoscopic image capture or direct view) is at guide tube 1606's distal end 1610. In one aspect guide tube 1606 is inserted into a patient via an incision (e.g., approximately 2.0 cm at the umbilicus) or natural orifice, either with or without the use of a cannula 1612 or similar guiding structure. In some aspects guide tube 1606 may rotate within cannula 1612.

As shown in FIG. 16, surgical instruments 1602a and 1602b function in a like manner, and many instrument functions (body roll, wrist operation, end effector operation, etc.) are similar to the surgical instruments used in the da Vinci® Surgical System (both 8 mm and 5 mm instrument body diameters). In other aspects the instruments may function differently and/or have capabilities not embodied in da Vinci® Surgical System instruments (e.g., one instrument may be straight, one instrument may be jointed, one instrument may be flexible, etc.). In the illustrative aspect shown in FIG. 16, instrument 1602a includes a transmission portion (not shown) at its proximal end, an elongated instrument body 1614, one of various surgical end effectors 1616, and a snake-like, two degree of freedom wrist mechanism 1618 that couples end effector 1616 to instrument body 1614. As in the da Vinci® Surgical Systems, in some aspects the transmission portion includes disks that interface with electrical actuators (e.g., servomotors) permanently mounted on a support arm so that instruments may easily be changed. Other linkages such as matching gimbal plates and levers may be used to transfer actuating forces at the mechanical interface. Mechanical mechanisms (e.g., gears, levers, gimbals) in the transmission portion transfer the actuating forces from the disks to cables, wires, and/or cable, wire, and hypotube combinations that run through one or more channels in instrument body 1614 (which may include one or more articulated segments) to control wrist 1618 and end effector 1616 movement. In some aspects, one or more disks and associated mechanisms transfer actuating forces that roll instrument body 1614 around its longitudinal axis 1619 as shown. In some aspects the actuators for a particular instrument are themselves mounted on a single linear actuator that moves instrument body 1614 longitudinally as shown within channel 1604a. The main segment of instrument body 1614 is a substantially rigid single tube, although in some aspects it may be slightly resiliently flexible. This small flexibility allows a proximal body segment 1620 proximal of guide tube 1606 (i.e., outside the patient) be slightly flexed so that several instrument bodies can be spaced more closely within guide tube 1606 than their individual transmission segment housings would otherwise allow, like several cut flowers of equal length being placed in a small-necked vase. This flexing is minimal (e.g., less than or equal to about a 5-degree bend angle in one embodiment) and does not induce significant friction because the bend angle for the control cables and hypotubes inside the instrument body is small.

As shown in FIG. 16, instruments 1602a and 1602b each include a proximal body segment that extends through the guide tube and at least one distal body segment that is positioned beyond the guide tube's distal end. For example, instrument 1602a includes proximal body segment 1620 that extends through guide tube 1606, a distal body segment 1622 that is coupled to proximal body segment 1620 at a joint 1624, a wrist mechanism 1626 that is coupled to distal body segment 1622 at another joint 1628 (the coupling may include another, short distal body segment), and an end effector 1630. In some aspects the distal body segment 1622 and joints 1624 and 1628 function as a parallel motion mechanism 1632 in which the position of a reference frame at the distal end of the mechanism may be changed with respect to a reference frame at the proximal end of the mechanism without changing the orientation of the distal reference frame.

Figure 16A:
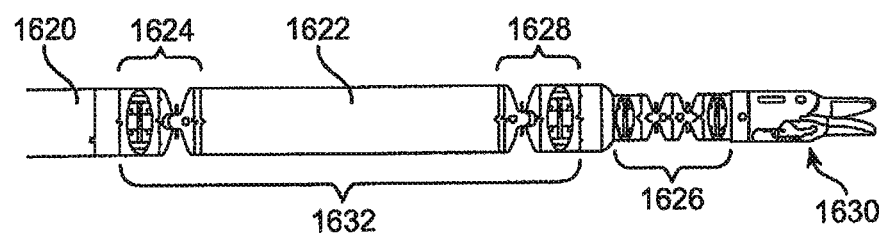
FIG. 16A is a side elevation view of an embodiment of the distal portion of a minimally invasive surgical instrument that includes a parallel motion mechanism.
Figures 16B, 16C:
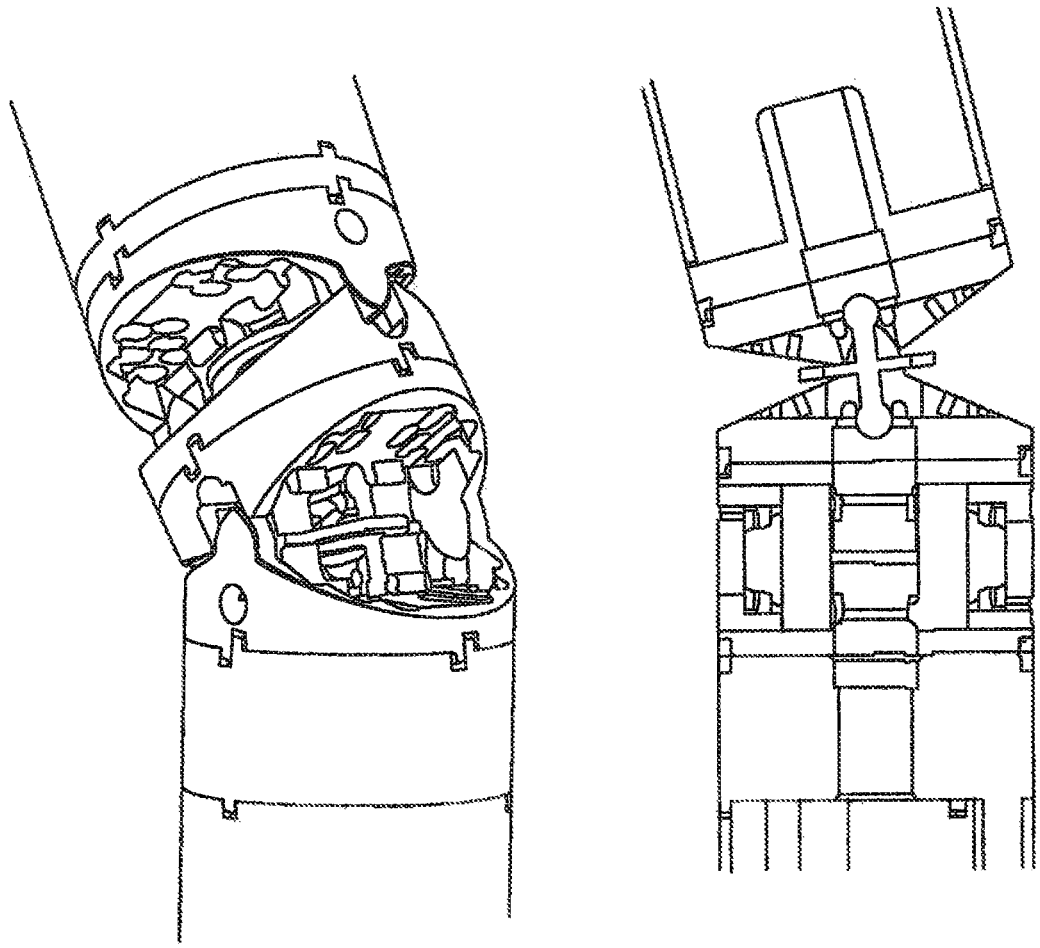
FIG. 16B is a perspective view.
FIG. 16C is a cross-sectional view, of an embodiment of joints in a parallel motion mechanism.

FIG. 16A is a side elevation view of an embodiment of the distal end of instrument 1602a, which includes parallel motion mechanism 1632, wrist mechanism 1626, and end effector 1630. In this illustrative embodiment, parallel motion mechanism 1632's diameter is approximately 7 mm, and wrist 1626's diameter is approximately 5 mm. FIG. 16A shows that joints 1624 and 1628 each have two hinges that pivot around orthogonal axes. As one hinge pivots in joint 1624, the corresponding hinge pivots an equal amount in the opposite direction in joint 1628. Accordingly, as distal body segment 1622 moves, the orientation of wrist 1626 and end effector 1630 remain essentially unaffected. The hinges are constructed with rolling contact so that cable lengths on each side of the pivot remain balanced ("virtual pivot points"); details are disclosed in U.S. Pat. No. 6,817,974 (Cooper et al.), which is incorporated by reference. U.S. Pat. No. 6,817,974 further discloses details about the Yaw-Pitch-Pitch-Yaw (YPPY; alternately PYYP) arrangement of the hinges in parallel motion mechanism 1632 (wrist 1626 is similarly configured), which provides a constant velocity roll configuration. Consequently, roll of proximal body segment 1620 is smoothly transferred to end effector 1630. Cables, wires, or bendable hypotubes are routed through a center channel in body segments 1620,1622, in joints 1624, 1628, and in wrist 1626 to operate end effector 1630 (e.g., opening and closing jaws in a gripper as shown). Cables that operate parallel motion mechanism 1632 and wrist 1626 are routed through openings near the periphery of the joints. FIG. 16B is a perspective view, and FIG. 16C is a cross-sectional view, of an illustrative embodiment of joints 1624, 1628.

As described herein, parallel motion mechanism 1632 includes two joints 1624 and 1628. Since the joints 1624, 1628 are coupled together, however, they do not operate independently of one another. Therefore, in joint space the entire parallel motion mechanism 1632 may be considered a single joint with two degrees of freedom (i.e., pitch and yaw) if "joints" 1624 and 1628 each have two orthogonal hinges (the position of the distal end of the mechanism may change in 3D Cartesian space), or as a single joint with one degree of freedom (i.e., pitch or yaw) if "joints" 1624 and 1628 each have a single hinge (the position of the distal end of the mechanism may change only in 2D Cartesian space). If parallel motion mechanism 1632 has two DOFs in joint space, then it functions as a constant velocity joint and transmits roll. Mechanism 1632's motion is "parallel" because the relative orientations of the proximal and distal ends (frames) of the mechanism remain constant as the mechanism changes the distal end's (frame's) position.

Figure 16D:
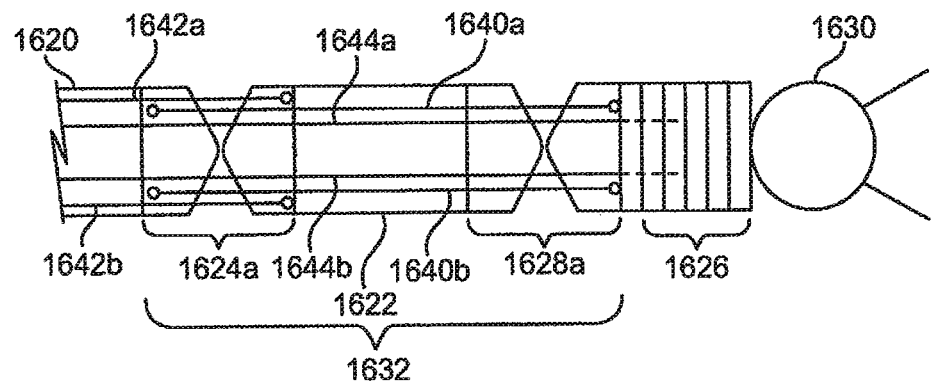
FIGS. 16D and 16E are schematic views that illustrate design and operation aspects of a parallel motion mechanism.
Figure 16E:
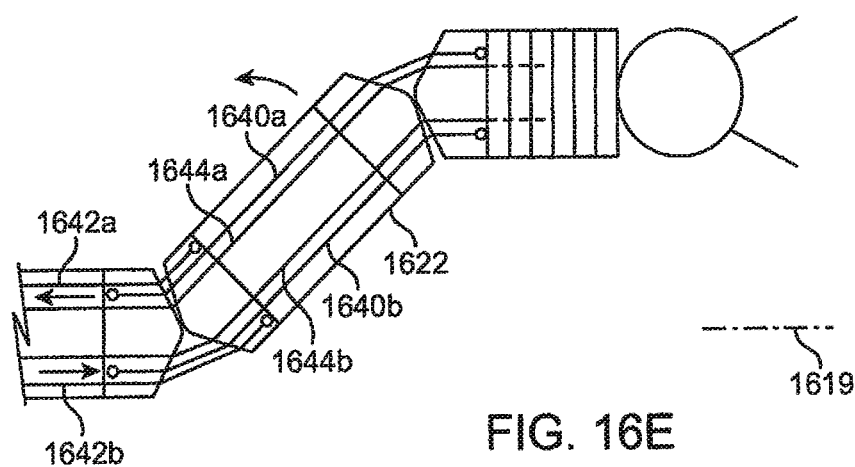

FIGS. 16D and 16E are schematic views that illustrate aspects of parallel motion mechanism 1632's design and operation principles. For clarity, only one set (i.e., PP or YY) of corresponding pivoting hinges is shown. The other set of hinges works the same way. Each hinge has a proximal link disk and a distal link disk. As shown in FIG. 16D, a first set of cables 1640a,1640b are positioned on opposite sides of parallel motion mechanism 1632 and couple the proximal link disk in hinge 1624a to the distal link disk in hinge 1628b. The two cables 1640a,1640b are illustrative of various combinations of cables that may be used (e.g., two cables on each side for increased strength; three cables spaced approximately 120 degrees apart will maintain parallelism in both planes; etc.). A second set of cables 1642a, 1642b are coupled to the distal link disk of hinge 1624a and run back through proximal body segment 1620 to the transmission mechanism (not shown). Other cables that control wrist mechanism 1626 and end effector 1630 are illustrated by a third set of cables 1644a,1644b.

As shown in FIG. 16E, when the transmission mechanism applies a tensile force on cable 1642a (cable 1642b is allowed to pay out), hinge 1624a pivots. The cable 1640a, 1640b coupling between the proximal link disk of hinge 1624a and the distal link disk of hinge 1628a causes hinge

1628*a* to pivot an equal amount in the opposite direction. Consequently, wrist 1626 and end effector 1630 are laterally displaced away from longitudinal axis 1619 of proximal body segment 1620. The lengths of cables 1644*a*,1644*b* are unaffected by the movement because of the hinge design, and so wrist 1626 and end effector 1630 orientation are also unaffected by the movement. If proximal instrument body segment 1620 were to remain stationary, then end effector 1630 translates slightly in a direction aligned with longitudinal axis 1619 (surged) in the patient's reference frame. Therefore, the control system, described below, compensates for this small movement by moving proximate body segment 1620 by an amount necessary to keep end effector 1630 at a constant insertion depth in the patient's reference frame.

In some instances when transmitting roll to the end effector is not required (e.g., for suction or irrigation tools, for an imaging system), each joint in the parallel movement mechanism may have only a single pivoting hinge. Further, skilled artisans will understand that if keeping end effector orientation is not required, then the parallel motion mechanism may be omitted. For instance, a proximal instrument body segment may be coupled to a distal instrument body segment at a joint with a single pivoting axis so that the proximal body segment must be rolled to move an end effector at the distal end of the distal body segment from side to side. Or, two or more elongated distal body segments may be used. If roll is not required, then the cross section of the body segments does not have to be round. In some aspects, the wrist mechanism may be eliminated.

FIG. 16F is a diagrammatic end view of a link disk, and it illustrates aspects of cable routing in a parallel motion mechanism. As shown in FIG. 16F, twelve cable routing holes are placed near the outside perimeter of link disk 1650. The cable routing holes are spaced 22.5 degrees apart from one another between the 3, 6, 9, and 12 O'clock positions on link disk 1650. Holes are not placed at the 3, 6, 9, and 12 O'clock positions because of the hinge components (not shown) on the obverse and reverse sides of link disk 1650. Starting at the 12 O'clock position, the holes are labeled 1652*a*-1652*l*. Four sets of three cables each are dedicated to four functions. A first set of cables maintains the parallel function in the parallel motion mechanism and are routed through holes 1652*a*, 1652*e*, and 1652*i*. A second set of cables are used to move a distal part of a wrist mechanism (e.g., wrist mechanism 1626) and are routed through holes 1652*b*, 1652*f*, and 1652*j*. A third set of cables are used to move the parallel motion mechanism and are routed through holes 1652*c*, 1652*g*, and 1652*k*. A fourth set of cables are used to move a proximal part of the wrist mechanism and are routed through holes 1652*d*, 1652*h*, and 1652*l*. Cables and other components associated with an end effector are routed through central hole 1654 in link disk 1650.

FIG. 16G is another diagrammatic end view of a link disk, and it illustrates further aspects of cable routing in a parallel motion mechanism. As shown in FIG. 16G, a first set of 12 cable routing holes are placed around the outside perimeter of link disk 1660 in a manner similar to those shown in FIG. 16F. In addition, a second set of 12 cable routing holes are placed around a concentric circle inside the first set of holes. Starting at the 12 O'clock position, the outer ring of cable routing holes are labeled 1662*a*-1662*l*, and the inner ring of holes are labeled 1664*a*-1664*l*. Cables associated with the parallel motion mechanism are routed through the outer ring of holes 1662, and cables associated with the wrist mechanism are routed through the inner ring of holes 1664. A first set of three cable pairs maintains the parallel function in the parallel motion mechanism and are routed through adjacent holes 1662*a* and 1662*l*, 1662*d* and 1662*e*, and 1662*h* and 1662*i*. A second set of three cable pairs are used to move the parallel motion mechanism and are routed through adjacent holes 1662*b* and 1662*c*, 1662*f* and 1662*g*, and 1662*j* and 1662*k*. A third set of three cable pairs is used to move a proximal part of the wrist mechanism and are routed through adjacent holes 1664*a* and 1664*l*, 1664*d* and 1664*e*, and 1664*h* and 1664*i*. A fourth set of three cable pairs are used to move a distal part of the wrist mechanism and are routed through adjacent holes 1664*b* and 1664*c*, 1664*f* and 1664*g*, and 1664*j* and 1664*k*. Cables and other components associated with an end effector are routed through central hole 1666 in link disk 1660.

The use of cable pairs as illustrated in FIG. 16G increases actuation stiffness above the stiffness of using a single cable. The increased stiffness allows the instrument components to be more accurately positioned during movement (e.g., the increased stiffness helps to reduce motion hysteresis). In one example, such cable pairs are used for an instrument with a parallel motion mechanism that is approximately 7 mm in diameter. Instruments with smaller diameters (e.g., approximately 5 mm in diameter), however, may not have sufficient internal space to accommodate cable pairs. In these situations, single cables routed in accordance with FIG. 16F may be coupled to a cable on the opposite side of the parallel motion mechanism. Aspects of such coupling are illustrated in FIGS. 16H-16J.

FIG. 16H is a diagrammatic perspective view of a stiffening bracket 1670 that couples cables routed on opposite sides of a parallel motion mechanism's body segment. Bracket 1670 has a cross piece 1672 and two parallel support members 1674 attached (e.g., welded) on opposite sides of cross piece 1672. A hypotube 1676 is attached (e.g., welded) to each support member so that the hypotubes are parallel to each other. The hypotubes 1676 are spaced apart a distance slightly less than the free space distance between the two cables to be coupled. The cable 1678 that maintains the parallel motion mechanism's parallel function is threaded through its associated hypotube 1676 as the cable extends between its two anchor points in the parallel motion mechanism. The hypotube 1676 is crimped to keep cable 1678 in place. The end of cable 1680 that is used to move the parallel motion mechanism is threaded into its associated hypotube 1676, which is crimped to keep cable 1680 in place. Consequently, the distal end of cable 1680 is anchored to a middle position (not necessarily halfway) of cable 1678. Referring to FIG. 16F, cables running through holes 1652*a* and 1652*g* are coupled together, cables running through holes 1652*c* and 1652*i* are coupled together, and cables running through holes 1652*e* and 1652*k* are coupled together. FIG. 16I illustrates an aspect of how multiple brackets 1670 may be positioned within the body of a parallel motion mechanism. That is, each cable that is associated with moving the parallel motion mechanism is coupled to an opposite side cable associated with maintaining the parallel function of the parallel motion mechanism.

Due to the way the hinges are constructed, described above, the cables that maintain the parallel function move within the body of the parallel motion mechanism, even though they are anchored at either end of the parallel motion mechanism. Therefore, for a given motion of the parallel motion mechanism, the cable coupling requires that the cables 1680, which move the parallel motion mechanism, move twice as far as they would if they were anchored to the parallel motion mechanism's body segment as illustrated in, e.g., FIGS. 16D-16E. The effect of this coupling increases joint stiffness approximately four times more than non-coupled cables because the cable moves twice as far, and because the load on the cable is half as great for a given joint torque.

FIG. 16J is a diagrammatic end view of a stiffening bracket 1670. As shown in FIG. 16J, cross piece 1672 is hollow so that cables and other components associated with an end effector may be routed through the cross piece. In one aspect, cross piece 1672 is made using electrical discharge machining. Referring again to FIG. 16, the proximal body portion, parallel motion mechanism, wrist, and end effector are aligned along longitudinal axis 1619 to allow the instrument to be inserted and withdrawn through guide tube 1606. Accordingly, two or more independently operating, exchangeable instruments, each with parallel motion mechanisms, can be simultaneously inserted via guide tube 1606 to allow a surgeon to enter a patient via a single entry port and work within a large volume deep within a patient. Each independent instrument's end effector has a full 6 DOF in Cartesian space (instrument insertion and the parallel motion mechanism provide the translation DOFs, and instrument body roll and the wrist mechanism provide the orientation DOFs). Further, the instruments 1602a,1602b may be partially withdrawn so that, e.g., only the wrist and end effectors extend from the guide tube 1606's distal end 1610. In this configuration, the one or more wrists and end effectors can perform limited surgical work.

Figure 17:
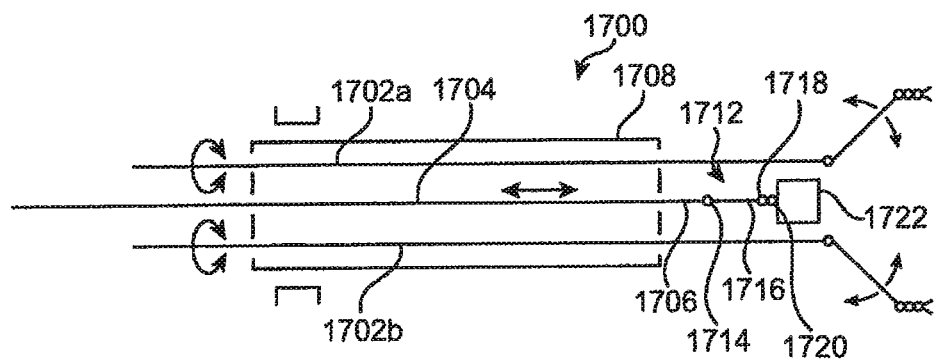
FIG. 17 is a schematic view that illustrates aspects of a thirteenth minimally invasive surgical instrument assembly.

FIG. 17 is a schematic view that illustrates aspects of a thirteenth minimally invasive surgical instrument assembly 1700. Surgical instrument assembly 1700 is similar to instrument assembly 1600 (FIGS. 16-16J) in that surgical instruments 1702a,1702b function similarly to instruments 1602a, 1602b as described above, but instead of a fixed endoscopic imaging system at the end of the guide tube, assembly 1700 has an independently operating endoscopic imaging system 1704.

In one aspect, imaging system 1704 is mechanically similar to surgical instruments 1602 as described above. Summarizing these aspects as shown in FIG. 17, optical system 1704 includes a substantially rigid elongate tubular proximal body segment 1706 that extends through guide tube 1708, and at proximal body segment 1706's distal end there is coupled a 1 or 2 DOF parallel motion mechanism 1712 that is similar to parallel motion mechanism 1622 (FIGS. 16-16J). Parallel motion mechanism 1712 includes a first joint 1714, an intermediate distal body segment 1716, and a second joint 1718. As shown in FIG. 17, in some aspects a wrist mechanism or other active joint (e.g., one DOF to allow changing pitch angle; two DOFs to allow changing pitch and yaw angles) 1720 couples an image capture component 1722 to second joint 1718. Alternatively, in another aspect joint 1714 is an independently controllable one or two DOF joint (pitch/yaw), joint 1718 is another independently controllable one or two DOF joint (e.g., pitch/yaw), and image capture component 1722 is coupled directly at the distal end of the joint 1718 mechanism. An example of a suitable stereoscopic image capture component is shown in U.S. patent application Ser. No. 11/614,661, incorporated by reference above. In some aspects imaging system 1704 moves longitudinally (surges) inside guide tube 1708. Control of imaging system 1704 is further described in concurrently filed U.S. patent application Ser. No. 11/762, 236 entitled "Control System Configured to Compensate for Non-Ideal Actuator-to-Joint Linkage Characteristics in a Medical Robotic System", which is incorporated by reference. In some aspects, roll may be undesirable because of a need to preserve a particular field of view orientation. Having heave, sway, surge, yaw, and pitch DOFs allows the image capture component to be moved to various positions while preserving a particular camera reference for assembly 1700 and viewing alignment for the surgeon.

Figure 17A:
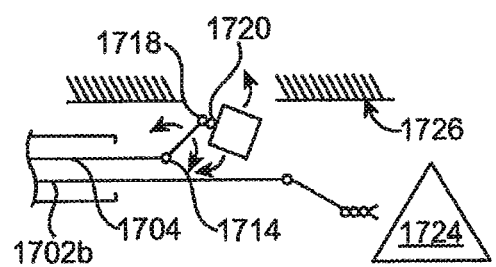
FIG. 17A is a schematic side view of a detail of FIG. 17.

FIG. 17A is, for illustrative purposes only, a side view schematic to FIG. 17's plan view schematic. FIG. 17A shows that parallel motion mechanism 1712 moves image capture component 1722 away from surgical instrument assembly 1700's longitudinal centerline. This displacement provides an improved view of surgical site 1724 because some or all of the instrument body distal segment ends are not present in the image output to the surgeon as would occur in, e.g., instrument assembly 1600 (FIG. 16). The pitch of parallel motion mechanism 1712 and of image capture component 1722 is controllable, as illustrated by the arrows.

Figure 17B:
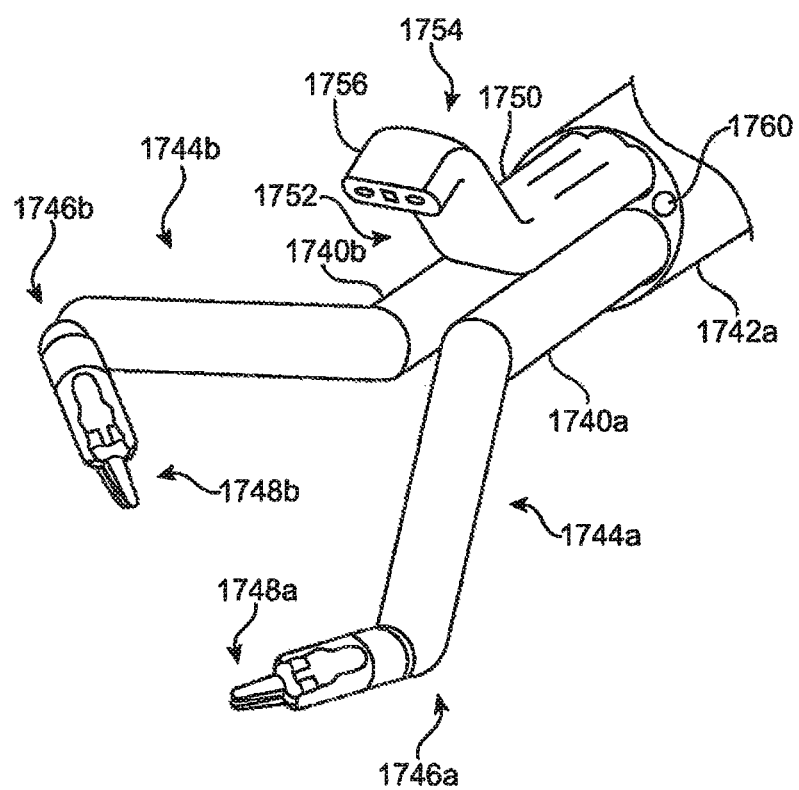
FIG. 17B is a diagrammatic perspective view of a surgical instrument assembly.

FIG. 17B is a diagrammatic perspective view that illustrates an embodiment of surgical instrument assembly 1700. As shown, two independently teleoperated surgical instruments 1740a,1740b (each instrument is associated with a separate master—e.g. one left hand master for the left instrument and one right hand master for the right instrument) run through and emerge at the distal end of a rigid guide tube 1742. Each instrument 1740a,1740b is a 6 DOF instrument, as described above, and includes a parallel motion mechanism 1744a,1744b, as described above, with wrists 1746a,1746b and end effectors 1748a,1748b attached. In addition, an independently teleoperated endoscopic imaging system 1750 runs through and emerges at the distal end of guide tube 1742. In some aspects imaging system 1750 also includes a parallel motion mechanism 1752, a pitch-only wrist mechanism 1754 at the distal end of the parallel motion mechanism 1752 (the mechanism may have either one or two DOFs in joint space), and a stereoscopic endoscopic image capture component 1756 coupled to wrist mechanism 1754. In other aspects, wrist mechanism 1754 may include a yaw DOF. In yet another aspect, the proximal and distal joints in imaging system 1750 are independently controlled. In an illustrative use, parallel motion mechanism 1752 heaves and sways image capture component 1756 up and to the side, and wrist mechanism 1754 orients image capture component 1756 to place the center of the field of view between the instrument tips if the instruments are working to the side of the guide tube's extended centerline. In another illustrative use, the distal body segment of imaging system is independently pitched up (in some aspects also independently yawed), and image capture component 1756 is independently pitched down (in some aspects also independently yawed). As discussed above and below, imaging system 1750 may be moved to various places to retract tissue.

Also shown is an auxiliary channel 1760, through which, e.g., irrigation, suction, or other surgical items may be introduced or withdrawn. In some aspects, one or more small, steerable devices (e.g., illustrated by instrument 902 in FIG. 9) may be inserted via auxiliary channel 1760 to spray a cleaning fluid (e.g., pressurized water, gas) and/or a drying agent (e.g., pressurized air or insufflation gas) on the imaging system's windows to clean them. In another aspect, such a cleaning wand may be a passive device that attaches to the camera before insertion. In yet another aspect, the end of the wand is automatically hooked to the image capture component as the image capture component emerges from the guide tube's distal end. A spring gently pulls on the cleaning wand so that it tends to retract into the guide tube as the imaging system is withdrawn from the guide tube.

FIG. 17A further illustrates that as image capture component 1722 is moved away from assembly 1700's centerline it may press against and move an overlying tissue structure surface 1726, thereby retracting the tissue structure from the surgical site as shown. The use of imaging system 1704 to retract tissue is illustrative of using other surgical instruments, or a device specifically designed for the task, to retract tissue. Such "tent-pole" type retraction may be performed by any of the various movable components described herein, such as the distal end exit or side exit flexible devices and the parallel motion mechanisms on the rigid body component devices, as well as other devices discussed below (e.g., with reference to FIG. 31).

Figure 18:
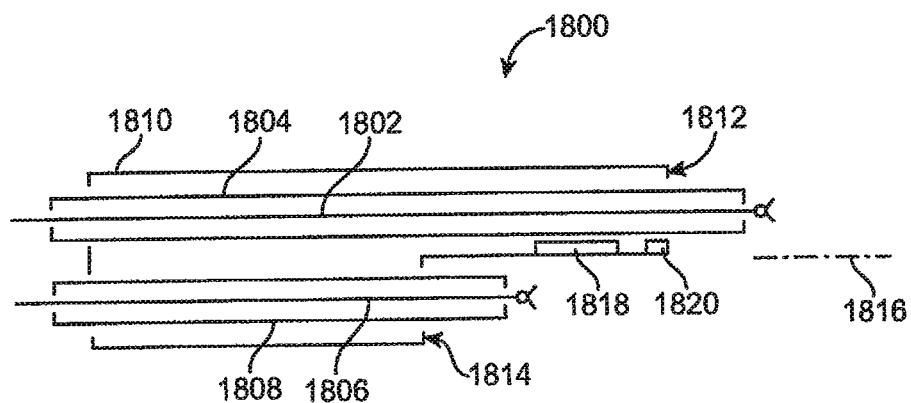
FIG. 18 is a schematic view that illustrates aspects of a fourteenth minimally invasive surgical instrument assembly.

In some aspects, one or more surgical instruments may exit from a guide tube generally aligned with the guide tube's longitudinal axis but not at the guide tube's distal end. FIG. 18 is a schematic view that illustrates aspects of a fourteenth minimally invasive surgical instrument assembly 1800. As shown in FIG. 18, a first surgical instrument 1802 runs coaxially through primary guide tube 1804, and a second surgical instrument 1806 runs coaxially through primary guide tube 1808. Instrument and primary guide tube combinations 1802,1804 and 1806,1808 are illustrative of the various flexible and rigid instruments and instrument/guide tube combinations described above. Instrument/guide tube combination 1802,1804 extends through and exits at secondary guide tube 1810's extreme distal end 1812. Instrument/guide tube combination 1806,1808 extends through secondary guide tube 1810 and exits at an intermediate position 1814 that is proximally spaced from extreme distal end 1812. In contrast to the side exits that direct instruments away from the guide tube's longitudinal axis as shown in, e.g., assemblies 1300 (FIG. 13) and 1400 (FIG. 14), instrument/guide tube combination 1806,1808 exits generally aligned with secondary guide tube 1810's longitudinal axis 1816. The distal and intermediate position guide tube face angles may be other than perpendicular to axis 1816.

FIG. 18 also shows that endoscopic imaging system 1818 is positioned on secondary guide tube 1810 between extreme distal end 1812 and intermediate position 1814. Imaging system 1818's field of view is directed generally perpendicular to longitudinal axis 1816. During surgery (e.g., within a long, narrow space), the surgical site is located within imaging system 1818's field of view and instrument/guide tube combinations 1802,1804 and 1806,1808 (working somewhat retrograde from its distal end 1812 exit) are moved to work at the surgical site. Imaging system 1818 is, in some aspects, an electronic stereoscopic image capture system. In some aspects, a second imaging system 1820 (e.g., a monoscopic system with lower resolution than imaging system 1818) is located to have a field of view generally aligned with axis 1816 to assist instrument assembly 1800 insertion. It can be seen that the architecture illustrated in FIG. 18 allows the guide tube's cross section to be relatively small—enough to accommodate the instruments and/or guide tubes that run through it (see e.g., FIG. 11B and associated description)—but the imaging system dimensions (e.g., the interpupillary distance in a stereoscopic system) can be larger than if positioned at the guide tube's distal end face.

Figure 18A:
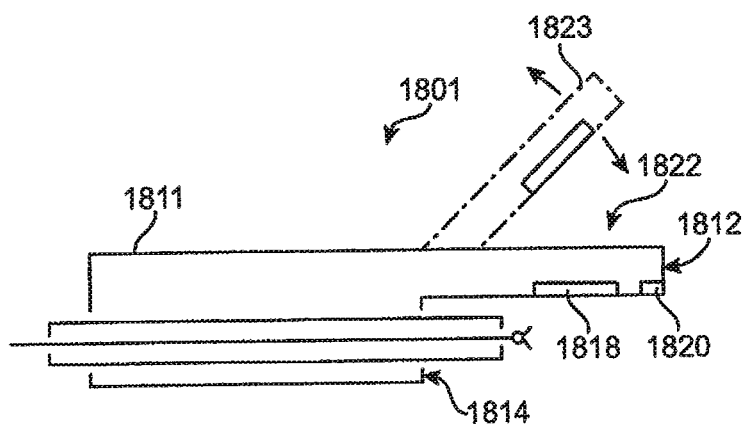
FIG. 18A is a schematic view that illustrates aspects of an imaging system at the distal end of an instrument assembly.

FIG. 18A is a schematic view that illustrates further aspects of an imaging system at the distal end of an illustrative instrument assembly 1801. As shown in FIG. 18A, one or more instruments and/or instrument/guide tube combinations exit from guide tube 1811's intermediate position 1814 as described above. Guide tube 1811's distal end segment 1822 is pivotally mounted so that it can be pitched in relation to guide tube 1811's main segment as shown by alternate position lines 1823, although not necessarily pivoting near the intermediate position as depicted. Alternate position 1823 is illustrative of various movements and mechanisms. For example, in one aspect a parallel motion mechanism as described above is used to displace imaging system 1818. In another example, alternate position 1823 represents positioning and orienting imaging system 1818 with two independently controllable 1 or 2 DOF joints. Other combinations of joints and links may be used. Accordingly, imaging system 1818's field of view direction can be altered, space permitting in the surgical site's vicinity. Distal end 1822 may be positioned above the exit ports as shown in FIG. 18A, or it may be positioned between the exit ports to provide a smaller instrument assembly cross section as illustrated by FIG. 18F.

Figure 18B:
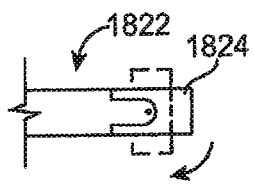
FIG. 18B is a schematic view that shows that illustrates aspects of imaging system movement.

FIG. 18B is another schematic view which shows that an imaging system 1824 may pivot in distal end segment 1822, as shown by the alternate position lines and arrow. Pivoting imaging system 1824 may be at the extreme distal end of the guide tube, or it may be positioned somewhat proximally from the extreme distal end (in which case in some aspects the second imaging system 1820 can be positioned at the distal end to provide viewing along the instrument assembly's longitudinal axis while imaging system 1824 is viewing to the side).

Figure 18C:
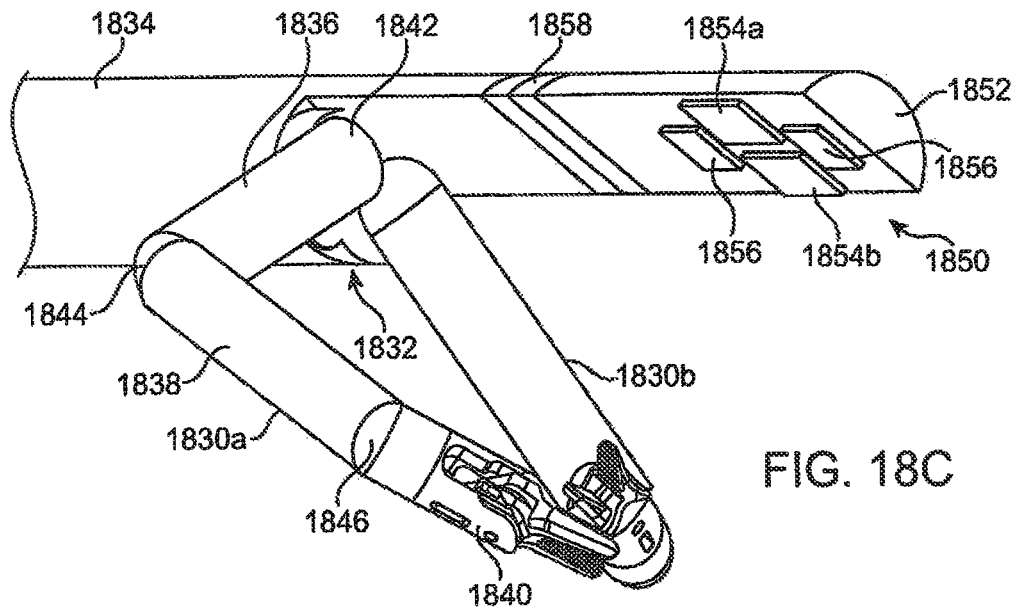
FIG. 18C is a diagrammatic perspective view of a minimally invasive surgical instrument assembly.

FIG. 18C is a diagrammatic perspective view of an embodiment of a minimally invasive surgical instrument assembly that incorporates aspects of instrument assemblies 1800 and 1801. As shown in FIG. 18C, two surgical instruments 1830a,1830b, each with rigid, movable distal links, extend from intermediate position 1832 on guide tube 1834. Each instrument 1830a,1830b includes an upper arm link 1836, a lower arm link 1838, and an end effector 1840 (illustrative grippers are shown). A shoulder joint 1842 couples upper arm link 1836 to the instrument body (not shown) that extends back through guide tube 1834. An elbow joint 1844 couples upper arm link 1836 to lower arm link 1838, and a wrist joint 1846 couples lower arm link 1838 to the end effector 1840. In some aspects, parallel motion mechanisms as described above with reference to FIGS. 16A-16J may be used, and in other aspects the shoulder and elbow joints may be independently controlled, as are the wrist joints 1846. In some aspects only a single arm link is used; in others more than two arm links are used. In some aspects, one or both shoulder joints 1842 are fixed to guide tube 1834 so that there is no associated instrument body.

Figure 18D:
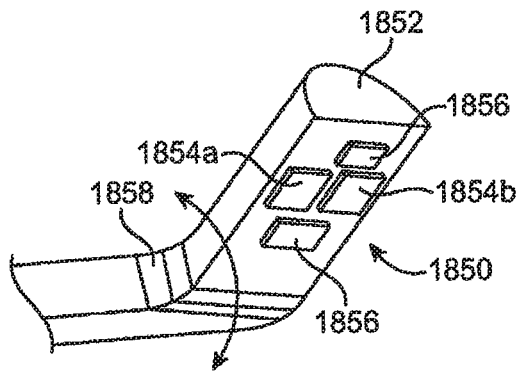
FIG. 18D is a diagrammatic perspective view that illustrates how a distal end of a surgical instrument assembly pitches up and down.

FIG. 18C further shows that a stereoscopic imaging system 1850 is mounted near the extreme distal end 1852 of guide tube 1834. As shown, imaging system 1850 includes right and left image capture elements 1854a,1854b, which may be positioned behind protective imaging ports, and illumination output ports (LEDs, optical fiber ends, and/or associated prisms that direct illumination light as desired) 1856. As described above, imaging system 1850's field of view is generally perpendicular to guide tube 1834's longitudinal axis so that a surgeon clearly sees end effectors 1840 working at a surgical site to the side of guide tube 1834's distal end. And, the axis between the imaging apertures is preferably generally parallel to a line between the surgical instrument tips, an alignment that presents to the surgeon an orientation in which the instrument tips map into natural and comfortable hand positions at the master console. In some aspects, as illustrated in FIG. 18A, guide tube 1834's distal end pivots at a joint 1858 so that imaging system 1850's field of view direction can be changed, as described above. Joint 1858 may be positioned at various locations on guide tube 1834. In one aspect, guide tube 1834 is approximately 12 mm outer diameter, the instruments are approximately 5 mm outer diameter, and imaging system 1850's lenses are about 3 mm across with an interpupillary distance of about 5 mm. FIG. 18D is a diagrammatic perspective view that illustrates how the distal end pitches up and down so that imaging system 1850 can look forwards (toward the distal direction; anterograde viewing) or backwards (toward the proximal direction; retrograde viewing).

As mentioned elsewhere in this description, although many aspects and embodiments are shown and described as having instruments and/or guide tubes that extend through other guide tubes, in other aspects instruments and/or guide tubes may be fixed at the end of, or at intermediate positions on, an instrument assembly structure so as to be integral with that structure. In some aspects, the fixed instruments and/or guide tubes may, however, be replaceable in vitro if the structure is removed from a patient. For example, a surgeon may remove the instrument assembly from the patient, replace one or more instruments that are attached (e.g., using known mechanisms) at the end or at an intermediate position with one or more other instruments, and then reinsert the instrument assembly.

Figure 18E:
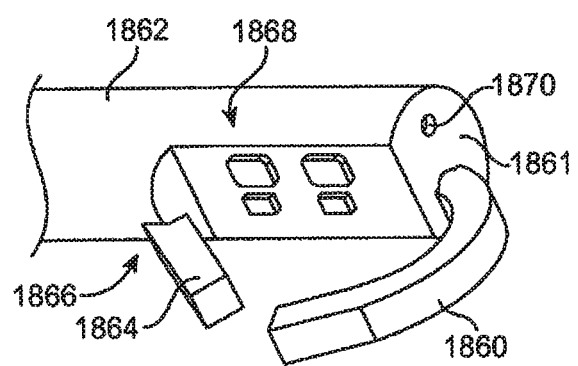
FIG. 18E is another diagrammatic perspective view of a minimally invasive surgical instrument assembly.
Figure 18F:
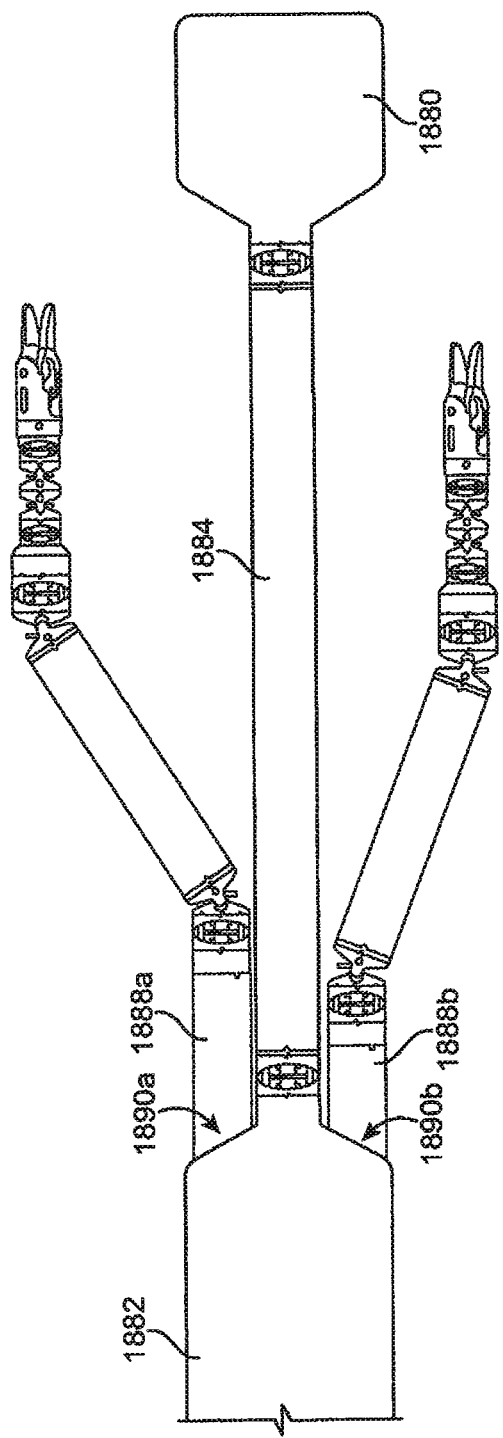
FIG. 18F is a diagrammatic plan view of a surgical instrument assembly with a movable imaging system at the distal tip of a guide tube.

FIG. 18E is a diagrammatic perspective view of an embodiment of a minimally invasive surgical instrument in which a movable surgical instrument 1860 (e.g., a U-Turn instrument as described below, a flexible arm, a multilink arm, and the like) is fixed at the extreme distal end 1861 of a guide tube 1862. Thus, the combination of guide tube 1862 and instrument 1862 functions in a manner similar to segments 15a and 15b of instrument 15 as shown and described in FIG. 2B. In addition, a second surgical instrument 1864 is either fixed at an intermediate position 1866 on guide tube 1862 or is removable as described above. And, as described above, an imaging system 1868 with a field of view direction generally perpendicular to guide tube 1862's longitudinal axis is positioned near guide tube 1862's distal end.

During insertion, in one aspect instrument 1860 is straightened to be generally aligned with the longitudinal axis, and instrument 1864 is either similarly aligned with the longitudinal axis (if fixed; if removably attached) or is at least partially withdrawn into the guide tube. Alternatively, in another aspect instrument 1860 may be retroflexively folded back against guide tube 1862. An optional second imaging system 1870 positioned at distal end 1861 may be used to assist insertion as described above.

FIG. 18F is an illustrative diagrammatic plan view of another aspect of a surgical instrument assembly with a movable imaging system at the distal tip of a guide tube. As depicted in FIG. 18F, an endoscopic image capture component 1880 is at the distal end of parallel motion mechanism 1884, which is coupled at the distal end of guide tube 1882. As shown, parallel motion mechanism 1884 has a single DOF in joint space so that it moves image capture component 1880 out of the page, towards the person looking at the figure. In some aspects, parallel motion mechanism may be thinner (between the two instruments) than shown in the figure since it has only one DOF as shown. In other aspects, parallel motion mechanism 1884 may have two DOFs as described above. Alternatively, two independently controllable joints may be used, with each joint generally placed where the hinges are shown in parallel motion mechanism 1884. In one aspect guide tube 1882 has an oblong cross section, as illustrated by FIG. 11B.

Figure 18G:
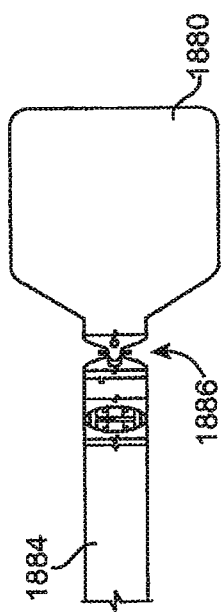
FIG. 18G is a diagrammatic detail that shows an alternate aspect of the surgical instrument assembly shown in FIG. 18F.

Additional DOFs may be used to orient image capture component 1880. For example, FIG. 18G illustrates that an independent yaw joint 1886 may be placed between parallel motion mechanism 1884 and image capture component 1880. Joint 1886 is illustrative of various single and multiple DOF joints that may be used (e.g., pitch or pitch/yaw). As illustrated below in FIG. 19J, in one aspect a flexible arm may be used instead of parallel motion mechanism 1884. Optics in image capture component 1880 may provide a down looking angle (e.g., 30 degrees).

FIG. 18F further shows that in one aspect parallel motion mechanism 1884 is long enough to allow the parallel motion mechanisms, wrist mechanisms, and end effectors of independently controllable instruments 1888a and 1888b to extend though intermediate position exit ports 1890a and 1890b in guide tube 1882 and move while image capture component 1880 is still aligned with the center of guide tube 1882. When parallel motion mechanism 1884 moves image capture component 1880 away from being aligned with guide tube 1882, instruments 1888a and 1888b can extend underneath image capture component 1880 to reach a surgical site.

Figure 19A:
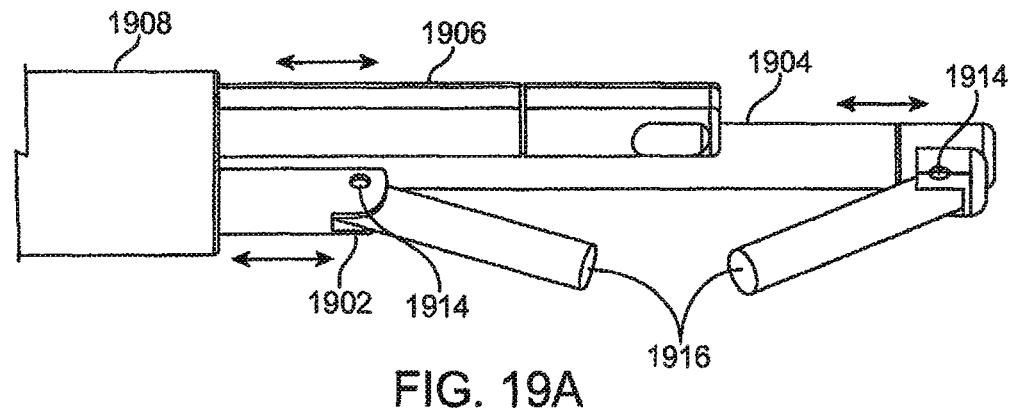
FIG. 19A is another diagrammatic perspective view of the embodiment depicted in FIG. 19.
Figure 19:
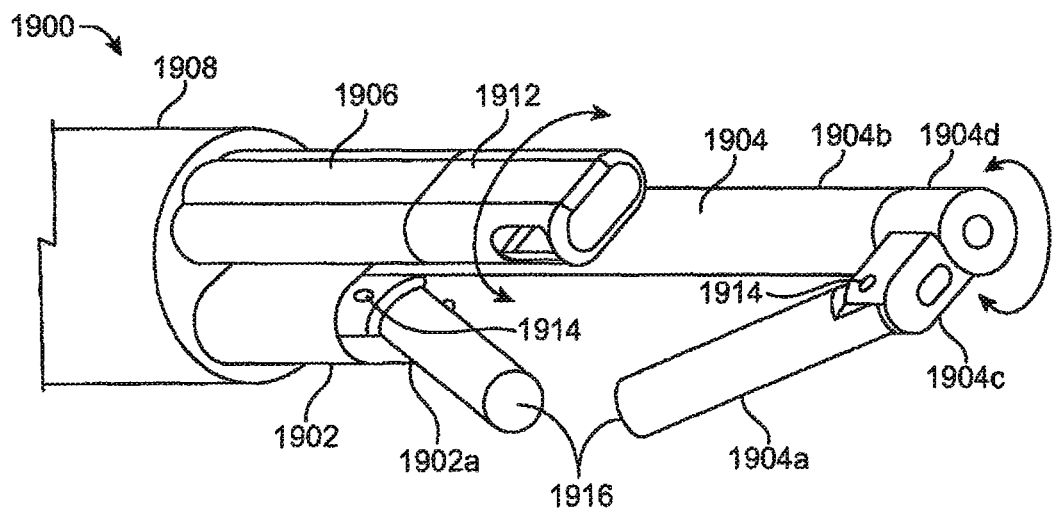
FIG. 19 is a diagrammatic perspective view that illustrates aspects of a fifteenth minimally invasive surgical instrument assembly.

FIG. 19 is a diagrammatic perspective view that illustrates aspects of a fifteenth minimally invasive surgical instrument assembly, showing an illustrative distal segment 1900 of the assembly. This assembly 1900, like some of the variations of assembly 1800 (FIGS. 18-18G), is primarily intended for surgical work to be performed generally to the side of the assembly rather than in front of its distal end. In the embodiment shown in FIG. 19, a first surgical instrument 1902, a second surgical instrument 1904, and an imaging system 1906 extend through a guide tube 1908. Various combinations of instruments and imaging systems may be used, either removable or fixed as described above. Surgical instrument 1902 generally works like the various instruments described above, its distal segment 1902a being rigid or flexible as described. And, instrument 1902 is illustrative of aspects in which is used a primary guide tube and instrument combination as described above. Guide tube 1908 may be rigid or flexible as described above. The surgical instrument bodies are, e.g., about 7 mm in diameter.

The image capture system in imaging system 1906 has a field of view that is generally perpendicular to instrument assembly 1900's longitudinal axis so that the surgeon can work at a site located to the side of the assembly. Imaging system 1906 may translate longitudinally (surge) within a channel defined in guide tube 1908, may be fixed to the distal end of guide tube 1908, or may be an integral part of guide tube 1908 as illustrated by aspects of assembly 1800 (FIGS. 18-18G). In some aspects with a round instrument body, imaging system 1906 may roll within the channel. The round instrument body must be large enough to accommodate, e.g., sensor data wiring (unless a wireless link is used) and an optical fiber illumination bundle. In other aspects the distal end 1912 alone may roll about imaging system 1906's longitudinal axis, as shown by the arrows, so as to place the surgical site within the field of view. If the distal end 1912 alone rolls, then an interface allows the sensor data wiring (unless a wireless link is used) and, e.g., power wires or optical fibers for illumination to bend to accommodate the roll.

Surgical instrument 1904 is designed to work primarily in retrograde. As shown in FIG. 19, the distal segment 1904a of instrument 1904 is joined to a body segment 1904b by a U-Turn mechanism 1904c. Components (such as, e.g., levers, pulleys, gears, gimbals, cables, cable guide tubes, and the like) inside U-turn assembly 1904c transmit mechanical forces (e.g., from cable or cable/hypotube combinations) around the U-turn (not necessarily 180 degrees as shown; other turn angles may be used) to move distal segment 1904*a* and an optional wrist mechanism, and to operate an end effector (not shown). U-Turn mechanism 1904*c* is distinguished from flexible mechanical structures because, e.g., it transmits mechanical forces through a radius of curvature that is significantly less than the minimum radius of curvature of equivalently sized flexible mechanical structures. Further, since the U-Turn mechanism does not itself move, the distance between a point where an actuating force enters the U-Turn mechanism and the point where the actuating force exits the U-Turn mechanism is unchangeable. For aspects in which a joint is placed in body segment 1904*b* so that it is divided into proximal and distal segments, and if instrument body roll is not transmitted through the joint, then the distal tip 1904*d* may be configured to rotate around the distal segment's longitudinal axis.

FIG. 19A is another diagrammatic perspective view of the embodiment depicted in FIG. 19, and it illustrates that during surgical work the distal ends of instruments 1902 and 1904 are generally within imaging system 1906's field of view to the side of assembly 1900.

FIGS. 19 and 19A further show that in some aspects the surgical instrument distal ends are coupled to the main bodies at a single pivot point 1914. Movement in more than one plane is facilitated by, e.g., a ball and socket type joint as illustrated above in FIG. 18C (1842) and below in FIGS. 19B and 19C. In other aspects, joints such as those shown in FIGS. 16A-C are used. End effectors (not shown) may be coupled directly or via wrist mechanisms at the extreme distal ends 1916.

Figure 19K:
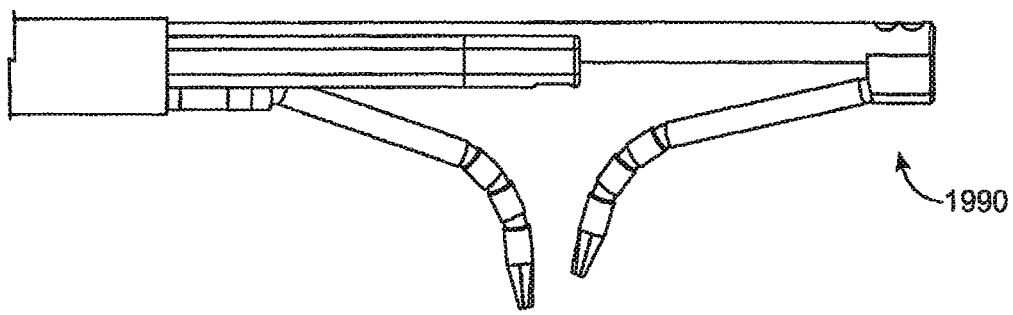
FIG. 19K is a plan view of a surgical instrument assembly.
Figure 19B:
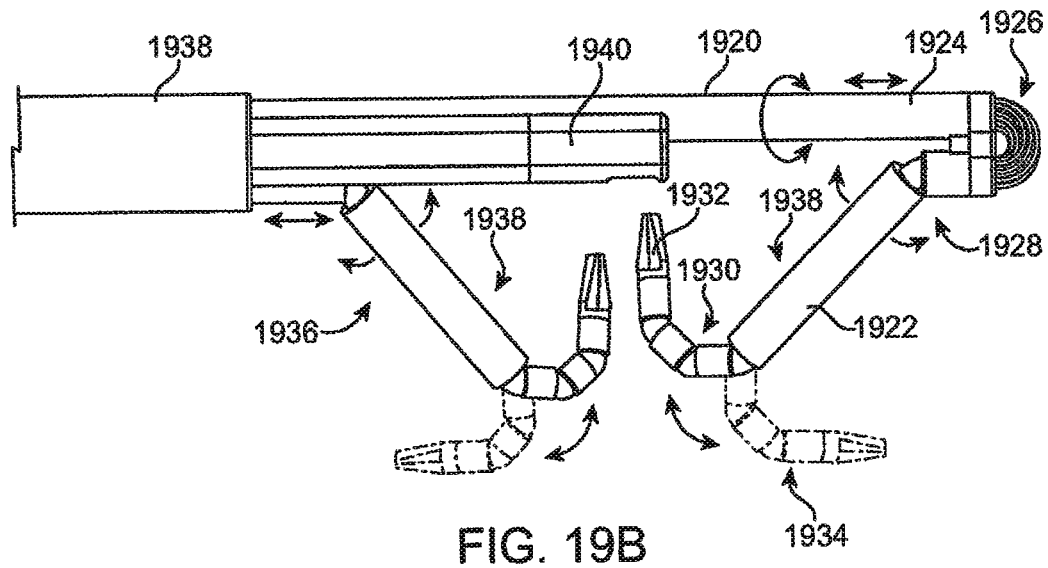
FIG. 19B is a plan view of a surgical instrument assembly.

FIG. 19B is a plan view of a surgical instrument assembly embodiment that incorporates a U-turn surgical instrument 1920. Distal instrument forearm segment 1922 is coupled to instrument main body segment 1924 via U-Turn mechanism 1926 and an illustrative controllable ball joint 1928. Wrist 1930 (ball and annular segment flexible mechanism is shown for illustration; other wrist mechanisms may be used as described above) couples end effector 1932 to the distal end of forearm segment 1922. Cables (not shown) that move forearm 1922, wrist 1930, and end effector 1932 are routed through individual cable guides in U-Turn mechanism 1926, as described in more detail below. The alternate position lines 1934 illustrate that in some instances wrist 1930 can bend at least 135 degrees in three dimensions to enable end effector 1932 to be oriented in various useful ways. An embodiment of such a wrist may incorporate, e.g., three 2-DOF joints of two hinges each, as described above with reference to FIGS. 16A-C. Each 2-DOF joint allows about 45 degrees of pitch and yaw from being aligned with forearm link 1922's longitudinal axis. In some aspects, rather than using the indexed joints as shown, a parallel motion mechanism and wrist combination as described above may be used. The surgical instrument assembly shown in FIG. 19C also incorporates a second surgical instrument 1936 that operates similarly to instrument 1920, except that it does not incorporate the U-Turn mechanism.

Figure 19C:
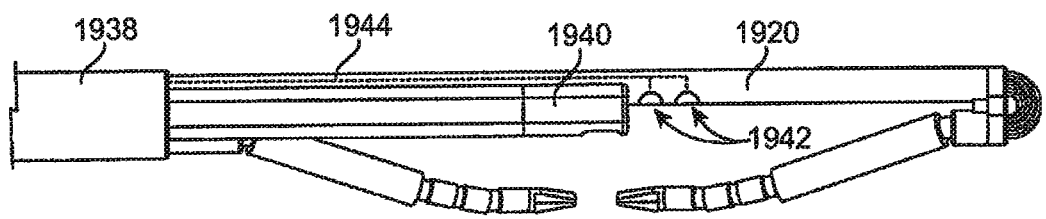
FIG. 19C is another plan view of the surgical instrument assembly shown in FIG. 19B.

FIG. 19C is another plan view of the surgical instrument assembly embodiment shown in FIG. 19B, with surgical instrument 1920 extended farther out of guide tube 1938. In FIG. 19B, the end effectors are working close to and pointing generally at imaging system 1940. In FIG. 19C, the end effectors are still working close to imaging system 1940, but they are now pointing generally perpendicular to imaging system 1940's viewing angle. Thus FIG. 19C illustrates that instrument 1920's extension distance from guide tube 1938 may depend on the end effector angle commanded by a master input control. It can also be seen that in some aspects if a command is given to change the end effector's orientation while maintaining its position, then the instrument body and forearm link must be moved to a new pose.

Figure 19D:
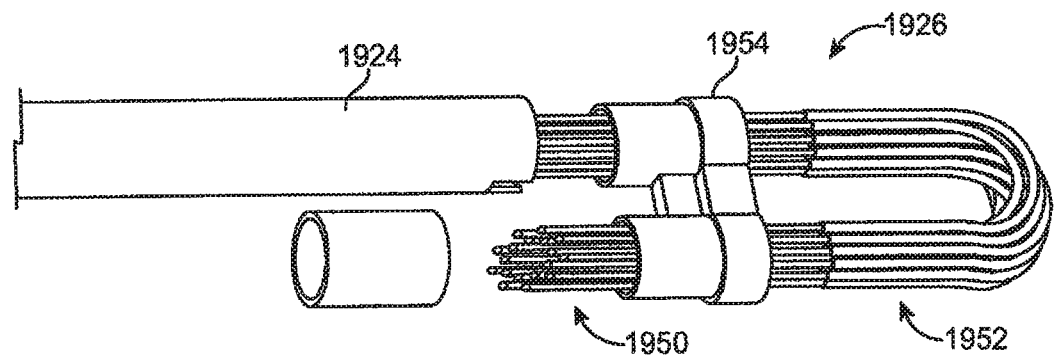
FIG. 19D is an exploded perspective view that illustrates aspects of a surgical instrument mechanism.

FIG. 19D is an exploded perspective view that illustrates aspects of routing cables (the term "cable" is illustrative of various filars (herein, the term "filars" should be broadly construed and includes, e.g., single- and multi-strand threads or even very fine hypotubes) that may be used) that control distal instrument components through a U-Turn mechanism. As shown in FIG. 19D, actuator cables 1950 for, e.g., forearm link 1922, wrist 1930, and end effector 1932 run through instrument main body segment 1924 and are routed through individual cable guide tubes 1952, which route cables 1950 around the U-Turn. The cable guide tubes are, e.g., stainless steel hypotubes. Brace 1954 clamps and therefore stabilizes both ends of the cable guide tubes 1952. Alternatively, or in addition, the cable guide tubes may be soldered or brazed. An outer cover may cover and protect the cable guide tubes and also any tissue against which the U-Turn instrument may press as it extends from its guide tube. In the embodiment shown, each individual cable guide tube is approximately the same length and has approximately the same bend radius (there are some small differences, as shown in the Figures). The approximately equal length and bend radius tubes make each cable's compliance, a function of diameter and length, approximately the same. Friction depends on the load and total bend angle of each cable.

In this illustrative embodiment, 18 cable guide tubes are shown. To control distal DOFs, the theoretical minimum number of tension cables is DOFs+1. More cables can be used for simplicity, to increase strength or stiffness, or to constrain joint behavior. In an illustrative 5 mm wrist mechanism as shown above, for example, two of the hinges are slaved through cables to two other hinges. In this example, 18 cables would be used to control 4 distal DOFs plus end effector grip. In some embodiments there is no roll control for the wrist mechanism. End effector roll is provided by rolling the instrument body shaft inside the guide tube. With coordinated movement of the other joints, rolling the instrument body shaft will roll the end effector around its end point.

Figure 19E:
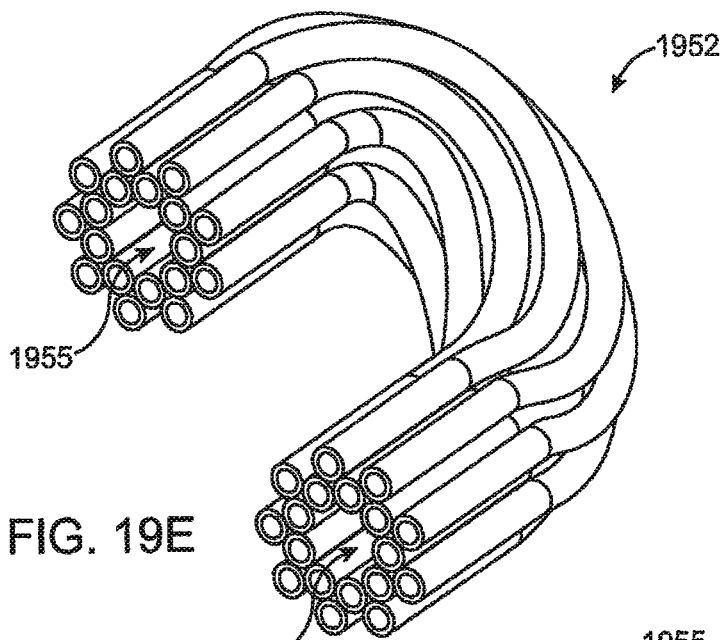
FIG. 19E is a perspective view of cable guide tubes.

FIG. 19E is a perspective view of an illustrative embodiment of the cable guide tubes 1952. A total of 18 cable guide tubes are shown. The cable guide tubes are arranged so as to form a central channel 1955, through which may be routed control cables for an end effector, surgical implements for suction, irrigation, or electrocautery, and the like. An optional sleeve (not shown) may be inserted within channel 1955 to reduce friction. Other numbers of guide tubes (e.g., 9) may be used.

Figure 19F:
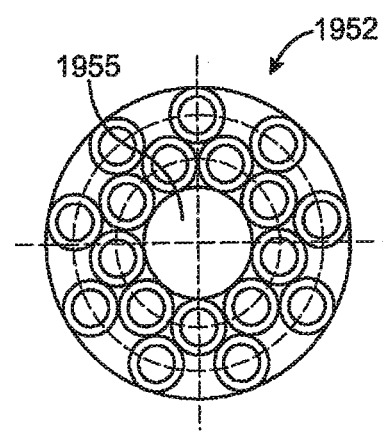
FIG. 19F is an end elevation view of cable guide tubes.

FIG. 19F is an end elevation view that shows the arrangement of guide tubes 1952 around the central channel 1955.

Figure 19G:
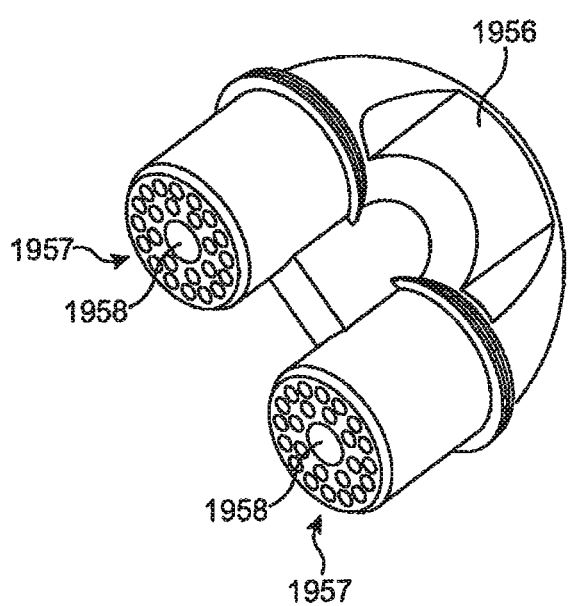
FIG. 19G is a perspective view of a cable guide piece.

FIG. 19G is a perspective view of an illustrative embodiment of an alternate way of routing cables around the U-Turn. Instead of using the multiple cable guide tubes 1952 and brace 1954, they are constructed as a single part 1956. Metal casting or rapid metal prototyping is used to make the part, which includes individual channels 1957 through which the cables are routed, and a central channel 1958 through which other components may be routed as discussed above.

Figure 19H:
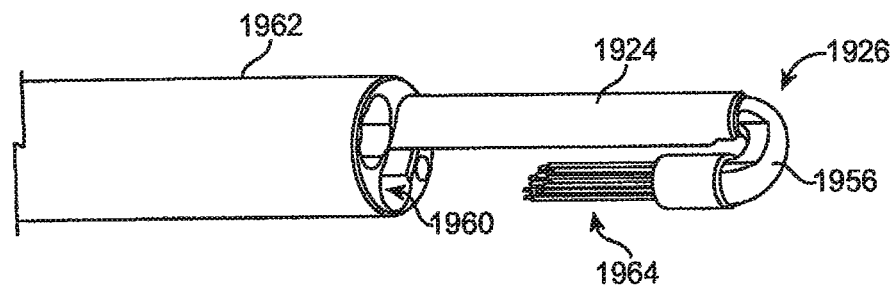
FIG. 19H is a perspective view that illustrates aspects of a surgical instrument passing through and exiting from a guide tube.

FIG. 19H is a perspective view that illustrates aspects of a surgical instrument with a U-Turn mechanism passing through and exiting from a guide tube. A single channel 1960 in guide tube 1962 is shaped to accommodate both the instrument's main body segment 1924 and the retrograde segment 1964 (only the control cables for the retrograde segment are shown; see e.g., FIG. 19B), which is folded back towards the main body segment as the instrument moves within the channel. The channel is pinched in the middle, so that when the U-Turn mechanism and retrograde segment exit the guide tube, the portion of the channel through which the main body segment passes still securely holds the main body segment. The single piece U-Turn part 1956 is also pinched as shown so that they slide within channel 1960. Once retrograde segment 1964 has exited guide tube 1962, a second instrument may be inserted through the portion of channel 1960 through which retrograde segment 1964 passed. Various other channel shapes that allow multiple instruments to be inserted through the guide tube are described in more detail below.

Figure 19I:
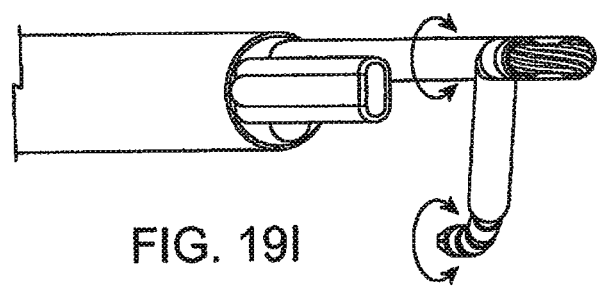
FIG. 19I is a perspective view that illustrates aspects of a surgical instrument's motion after exiting from a guide tube.

FIG. 19I is a perspective view that illustrates that once the U-Turn instrument exits the guide tube it may be rolled within the channel, and then the forearm link can be moved so that the end effector is positioned within the imaging system's field of view. In one aspect, keeping the end effector in position and rolling the instrument body within the guide tube rolls the end effector, as shown by the rotational arrows, because of the nature of the joints.

Figure 19J:
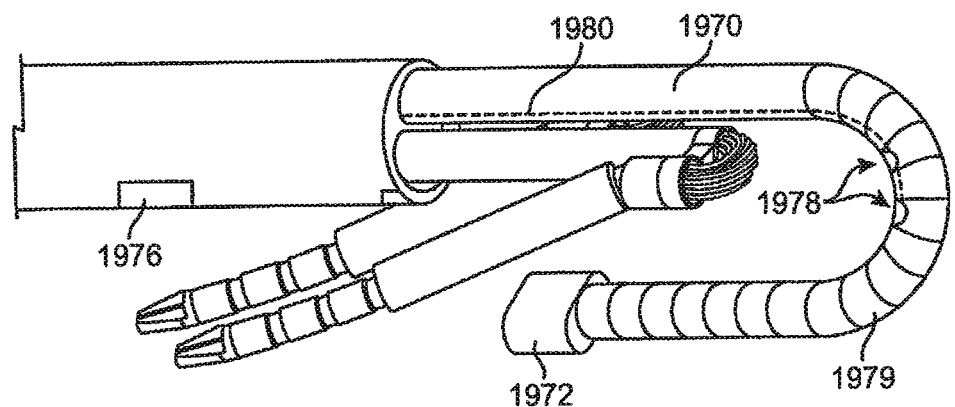
FIG. 19J is a perspective view that illustrates aspects of a surgical instrument assembly with two retrograde surgical instruments.

FIG. 19J is a perspective view that illustrates aspects of a surgical instrument assembly embodiment that uses more than one U-Turn retrograde surgical instrument. Using two U-Turn instruments allows the end effectors to work back closely to the guide tube. In order to provide image capture for the surgeon, an illustrative independent imaging system 1970 is shown with an image capture component 1972 mounted at the end of an illustrative flexible mechanism 1974. A U-Turn mechanism or a series of rigid links may be used instead of a flexible mechanism. Retroflexing the imaging system allows image capture component 1972's field of view to encompass the two U-Turn instrument end effectors. Alternatively, an imaging system 1976 may be positioned at the side of the guide tube if the end effectors are to work generally to the side of the instrument assembly.

FIG. 19K is a plan view that illustrates another aspect of the U-turn mechanism 1990, which uses small levers, for example, to transmit forces from the main instrument body to the distal forearm link, wrist mechanism, and end effector. Various cables, wires, rods, hypotubes, and the like, and combinations of these components, may be used in the main body and forearm and are coupled to the force transmission components.

Depending on the location of the surgical work site in relation to the instrument assembly and instruments to be used, illumination for the imaging system may be positioned at various places in side- and retroflexive-working systems. In addition to, or instead of, having one or more illumination output ports near the image capture component as described above, one or more illumination LEDs may be placed on the body of the retroflexive tool. Referring to FIG. 19C, for example, one or more LEDs may be placed at an illustrative position 1942, along instrument main body segment 1920. Or, LEDs may be placed along the forearm segment at, e.g., 1938 as shown in FIG. 19B. Likewise, LEDs may be placed at the inner curve of a retroflexing flexible mechanism, such as at positions 1978 shown in FIG. 19J. An advantage of placing additional illumination some distance away from the imaging apertures is that the additional illumination may provide shadows, which provides better depth cues. Illumination near or surrounding the imaging apertures, however, prevents the shadows from becoming so deep that details are not visible in the shadowed areas. Accordingly, in some aspects illumination both near to and far from the imaging apertures is used.

One or more channels, illustrated by dashed lines 1944 (FIG. 19C) or 1980 (FIG. 19J), in the structure on which the LEDs are mounted may carry cooling fluid (e.g., water) past the LEDs. The LED die (or multiple LED die) can be mounted on the obverse side of a thermally conductive substrate (e.g., an aluminum plate, a plated ceramic), which is bonded to the cooling channel so that the reverse side of the substrate is exposed to the cooling flow. Techniques for bonding LEDs to substrates are well known and can be adapted for use with liquid cooling. The cooling fluid may circulate in a closed system, or it may empty either inside or outside the patient. For an open cooling system that empties into the patient, a sterile, biocompatible fluid (e.g., sterile isotonic saline) is used. Suction may be used to remove the cooling fluid from the patient. In addition, the cooling fluid discharged into the patient may be used to perform other functions. For example, the discharged cooling fluid may be directed across the imaging lenses. The fluid may clean the lenses or prevent body fluids, smoke, or surgical debris from sticking to the lenses.

The amount of cooling fluid to keep an LED within an acceptable temperature range is fairly small. For example, an LED that dissipates about 4 Watts of electrical power as heat can be cooled with a flow of about 0.1 cc/sec of water through 0.020-inch OD plastic tubing (e.g., 12 feet total length; 6 feet supply and 6 feet return), and the water will experience only about a 10-degree Celsius temperature rise.

The use of LEDs as described above is an example of alternative illumination placement on the instruments. In some aspects, fiber light guides may be used, in which case cooling considerations do not apply.

As discussed above, in some aspects the cross-sectional area of a guide tube must accommodate instruments which themselves have distal portions with a relatively large cross-sectional area. In order to minimize the guide tube's cross-sectional area, in one aspect more than one instrument is inserted through a single specially shaped channel.

Figure 20A:
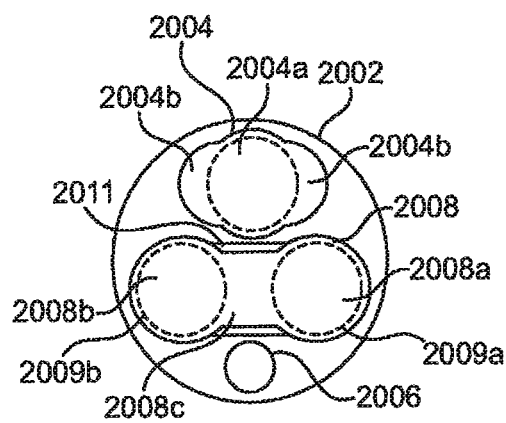
FIG. 20A is an end elevation view of the distal end face of a guide tube.

FIG. 20A is an end elevation view of the distal end face of illustrative guide tube 2002. Guide tube 2002's lateral cross section is similarly configured (i.e., the channels depicted extend through the entire guide tube). As shown in FIG. 20A, guide tube 2002 has three channels (more or fewer channels may be used). Channel 2004 accommodates an endoluminal imaging system and may have various cross-sectional shapes (e.g., round, oval, rounded polygon, etc.). The shape illustrated in FIG. 20A is a circle overlaid and centered on a rounded rectangle. The circular bore 2004a of channel 2004 accommodates the imaging system's body (illustrated by dashed lines), and the slots 2004b (the ends of the rounded rectangle) on either side of the circular bore 2004a allow the image capture element, which is wider than the cylindrical body segment, to pass through channel 2004. Since the circular bore 2004a has a slightly larger diameter than slots 2004b (the channel 2004 cross section is an oblong, biconvex shape), the imaging system's body segment is held in place within channel 2004 after the image capture element exits guide tube 2002's distal end.

Channel 2006, depicted as a single, circular bore, is an optional auxiliary channel and may be used for irrigation, suction, small (e.g., 3 mm diameter) instruments, etc.

Channel 2008 is uniquely shaped to simultaneously accommodate two surgical instruments in which one has a distal end segment larger than its body segment, such as instruments 1902 and 1904 (FIG. 19). As shown in FIG.

20A, channel 2008's cross-sectional shape is generally oblong with a pinched center across the major axis (the cross section is an oblong, biconcave shape). Channel 2008 includes two cylindrical bores 2008a,2008b through which cylindrical instrument bodies are inserted. The bores 2008a, 2008b are interconnected by a slot 2008c. As an instrument body (illustrated by the circular dashed line 2009a) is inserted through bore 2008a, for example, the instrument's distal portion, which is larger than its proximal body segment, passes through at least part of slot 2008c and possibly some or all of bore 2008b. FIG. 19H illustrates this aspect. Once the instrument's distal portion has been inserted beyond the guide tube's distal end, the instrument's proximal body segment is rotated within bore 2008a, which holds the proximal body segment in place. Consequently, another instrument (illustrated by the circular dashed line 2009b), either cylindrical or with an enlarged distal portion that fits through slot 2008c, can be inserted through bore 2008b. This channel configuration and insertion process can be used for various instruments with odd-shaped distal portions, such as staplers, clip appliers, and other special task instruments, as well as for the retrograde working instruments described herein. In addition, an imaging device having a distal image capture component cross section larger than its body cross section and shaped to pass through the channel's oblong cross section may be similarly inserted, followed by one or more other instruments. The lip 2011 of channel 2008, or any channel, is in some instances rounded or beveled as shown to facilitate instrument withdrawal into the guide tube.

Figure 20B:
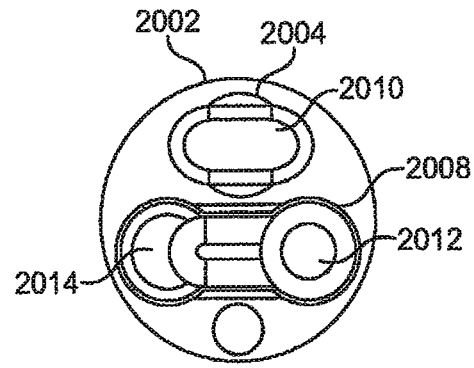
FIG. 20B is an end elevation view of the distal end face of guide tube shown in FIG. 20A, with an imaging system and two surgical instruments.

FIG. 20B is an end elevation view of the distal end face of guide tube 2002 with an illustrative imaging system 2010 and two surgical instruments 2012,2014, all extending from their insertion channels 2004,2008. Instrument 2012 is a U-Turn mechanism type retrograde working instrument, similar to the illustrative embodiment shown in FIGS. 19 and 19A. Instrument 2014 is generally circular in cross section during insertion, although during insertion a portion of instrument 2014 may extend into any portion of slot 2008c that instrument 2012 does not occupy. As another example, an instrument with the multiple cable guide tube U-Turn mechanism, similar to the embodiments shown in FIGS. 19B-19I, may be inserted through channel 2008, with the body and distal portions of the instrument passing through the bores and the pinched portion of the U-Turn mechanism passing through the slot between the bores.

Figure 20C:
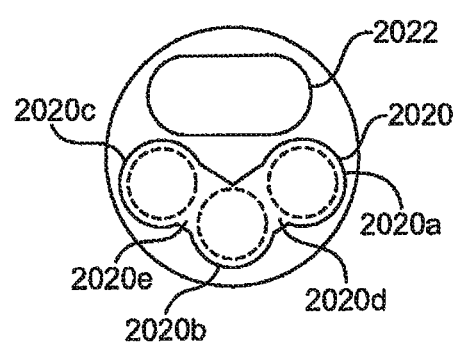
FIG. 20C is an end elevation view that illustrates a guide tube with an instrument channel that includes grooves arranged in a "V" shape.

The channel topography illustrated in FIG. 20A can be adapted to allow, e.g., two instruments with large distal ends to be inserted through a guide tube, possibly adding a third instrument as well. FIG. 20C is an end elevation view that illustrates aspects in which an instrument channel includes bores arranged in a "V" shape, although the "V" may be flattened so that three or more channel bores are side-by-side in a line. As shown, channel 2020 includes three cylindrical bores 2020a,2020b,2020c, with slot 2020d joining bores 2020a and 2020b, and slot 2020e joining bores 2020b and 2020c. Bores 2020a and 2020c are shown at the ends of the "V" shape, and bore 2020b is shown at the vertex of the "V" shape. Illustratively, a first retrograde working instrument with a U-Turn mechanism is inserted via bores 2020a and 2020b, and then a second retrograde working instrument with a U-Turn mechanism is inserted via bores 2020c and 2020b. Once inserted, the three bores allow either of the instruments to be independently removed—one instrument does not have to be removed to allow the other instrument to be removed. An optional third instrument may be inserted via bore 2020b once two other instruments are inserted with their proximal body segments held in place within bores 2020a and 2020c. It can be seen that two large-ended instruments and an optional third instrument may be inserted via channel 2020 in various combinations. An imaging system may be inserted via channel 2022, which may be a rounded rectangle as shown, circular, or various other shapes as illustrated herein (e.g., 2004 in FIG. 20A). Alternatively, if an imaging system has a suitably shaped distal end, it may be inserted via channel 2020. An assembly with two retrograde working instruments and an imaging system is illustrated in FIG. 19J.

Figure 20D:
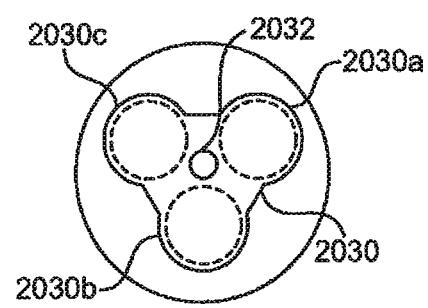
FIGS. 20D, 20E, and 20F are each end elevation views that illustrate other guide tube channel configurations.
Figure 20E:
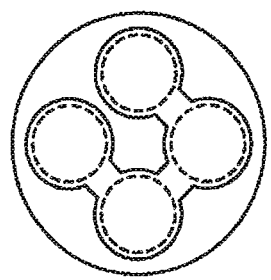
Figure 20F:
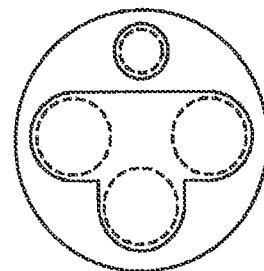

FIGS. 20D, 20E, and 20F are each end elevation views that illustrate aspects of other channel configurations that may be used to accommodate one or more instruments with large distal ends. FIG. 20D shows channel 2030 with three bores 2030a,2030b,2030c in a triangular arrangement. The slots that interconnect adjacent bores merge into a single opening that connects each bore with the other two (i.e., the top of the "V" shape illustrated in FIG. 20C is joined by a third slot. The channel has a generally triangular cross section, and the bores are at the triangle's vertices). Also shown is an illustrative spacer 2032, shown centered in channel 2030, which helps keep the instrument bodies in their bores or positioned at their vertexes if the channel sides between the bores are not sufficiently pinched to hold the instrument bodies in place within the bores. FIG. 20E illustrates that the channel can have any number of bores to accept surgical instruments (four are shown with the bores arranged at the corners of a square). FIG. 20F illustrates a channel with a "T" shape, the bores for the instruments being the three ends of the "T". A spacer such as shown in FIG. 20D may be used to keep instruments properly positioned within the "T", or the connecting openings between the bores may be slightly pinched to keep the instruments in their bores. Other cross-sectional channel shapes (e.g., a cross or "X" shape; it can be seen that a "T" shape is part of such a cross or "X" shape) may be used with a cross-sectional configuration or a separate component that keeps a surgical instrument's body or shaft in place within the channel.

In FIGS. 20A-20F, the bores that hold the proximal segments of the instrument and imaging system bodies are shown as circular, which allows the bodies to roll within the bores. In some aspects, however, some or all the bores may have non-circular cross sections to prevent the body segments from rolling within the bores. For example, one non-circular bore may be dedicated to holding the proximal body segment of an imaging system, which is kept from rolling. Or, specifically shaped bores may be used to ensure that only a particular device may be inserted into a particular bore. In some aspects, however, any surgical instrument or imaging system may be inserted via any bore.

Support and Control Aspects

Figure 21A:
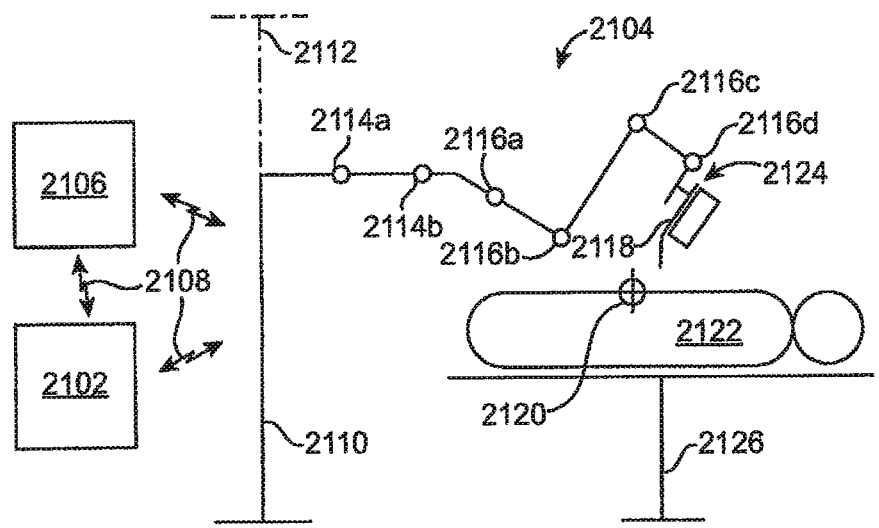
FIG. 21A is a schematic view of a robot-assisted minimally invasive telesurgical system.

FIG. 21A is a schematic view that illustrates aspects of a robot-assisted (telemanipulative) minimally invasive surgical system that uses aspects of the minimally invasive surgical instruments, instrument assemblies, and manipulation and control systems described herein. This system's general architecture is similar to the architecture of other such systems such as Intuitive Surgical, Inc.'s da Vinci® Surgical System and the Zeus® Surgical System. The three main components are a surgeon's console 2102, a patient side support system 2104, and a video system 2106, all interconnected 2108 by wired or wireless connections as shown. One or more electronic data processors may be variously located in these main components to provide system functionality.

The surgeon's console 2102 includes, e.g., multiple DOF mechanical input ("master") devices that allow the surgeon to manipulate the surgical instruments, guide tubes, and imaging system ("slave") devices as described herein. These input devices may in some aspects provide haptic feedback from the instruments and instrument assembly components to the surgeon. Console 2102 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference above. Control during insertion may be accomplished, for example, in a manner similar to telemanipulated endoscope control in the da Vinci® Surgical System—in one aspect the surgeon virtually moves the image with one or both of the masters; she uses the masters to move the image side to side and to pull it towards herself, consequently commanding the imaging system and its associated instrument assembly (e.g., a flexible guide tube) to steer towards a fixed center point on the output display and to advance inside the patient. In one aspect the camera control is designed to give the impression that the masters are fixed to the image so that the image moves in the same direction that the master handles are moved, as in the da Vinci® surgical system. This design causes the masters to be in the correct location to control the instruments when the surgeon exits from camera control, and consequently it avoids the need to clutch (disengage), move, and declutch (engage) the masters back into position prior to beginning or resuming instrument control. In some aspects the master position may be made proportional to the insertion velocity to avoid using a large master workspace. Alternatively, the surgeon may clutch and declutch the masters to use a ratcheting action for insertion. In some aspects, insertion (e.g., past the glottis when entering via the esophagus) may be controlled manually (e.g., by hand operated wheels), and automated insertion (e.g., servomotor driven rollers) is then done when the distal end of the surgical instrument assembly is near the surgical site. Preoperative or real time image data (e.g., MRI, X-ray) of the patient's anatomical structures and spaces available for insertion trajectories may be used to assist insertion.

The patient side support system 2104 includes a floor-mounted base 2110, or alternately a ceiling mounted base 2112 as shown by the alternate lines. The base may be movable or fixed (e.g., to the floor, ceiling, or other equipment such as an operating table). In one embodiment the manipulator arm assembly is a modified da Vinci® Surgical System arm assembly. The arm assembly includes two illustrative passive rotational setup joints 2114a,2114b, which allow manual positioning of the coupled links when their brakes are released. A passive prismatic setup joint (not shown) between the arm assembly and the base may be used to allow for large vertical adjustments. In addition, the arm assembly includes illustrative active roll joint 2116a and active yaw joint 2116b. Joints 2116c and 2116d act as a parallel mechanism so that a guide tube (of a surgical instrument assembly) held by guide manipulator 2118 moves around remote center 2120 at an entry port, such as patient 1222's umbilicus. An active prismatic joint 2124 is used to insert and withdraw the guide tube. One or more surgical instruments and an endoscopic imaging system are independently mounted to guide manipulator 2118. The various setup and active joints allow the manipulators to move the guide tube, instruments, and imaging system when patient 2122 is placed in various positions on movable table 2126.

Figures 21B, 21C:
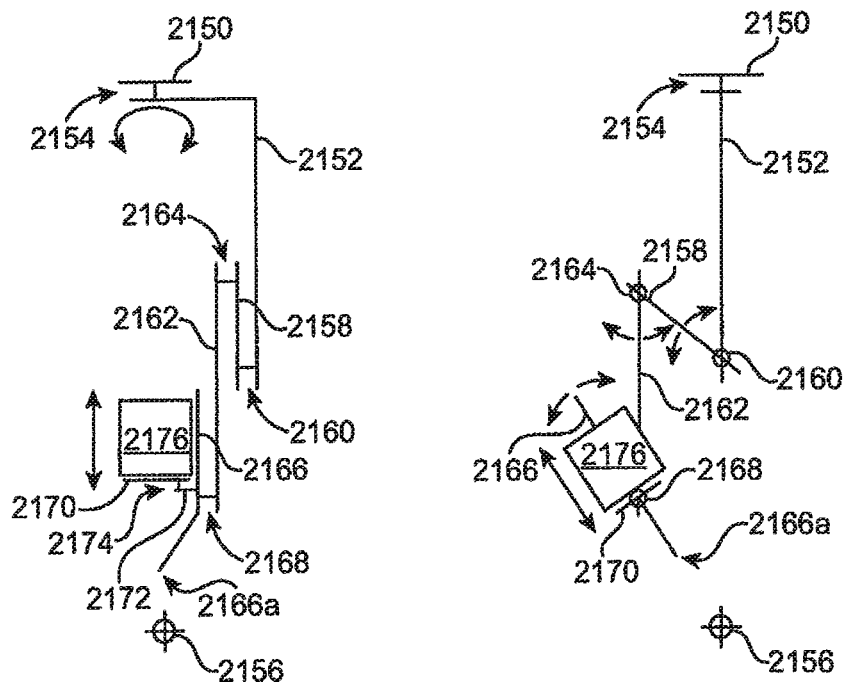
FIGS. 21B and 21C are schematic views of a patient side support system in a telesurgical system.

FIGS. 21B and 21C are schematic side and front elevation views of another illustrative embodiment of a patient side support system. Base 2150 is fixed (e.g., floor or ceiling mounted). Link 2152 is coupled to base 2150 at passive rotational setup joint 2154. As shown, joint 2154's rotational axis is aligned with remote center point 2156, which is generally the position at which a guide tube (of a surgical instrument assembly; not shown) enters the patient (e.g., at the umbilicus for abdominal surgery). Link 2158 is coupled to link 2152 at rotational joint 2160. Link 2162 is coupled to link 2158 at rotational joint 2164. Link 2166 is coupled to link 2162 at rotational joint 2168. The guide tube is mounted to slide through the end 2166a of link 2166. Manipulator platform 2170 is supported and coupled to link 2166 by a prismatic joint 2172 and a rotational joint 2174. Prismatic joint 2172 inserts and withdraws the guide tube as it slides along link 2166. Joint 2174 includes a bearing assembly that holds a "C" shaped ring cantilever. As the "C" ring slides through the bearing it rotates around a center point inside the "C", thereby rolling the guide tube. The opening in the "C" allows guide tubes to be mounted or exchanged without moving overlying manipulators. Manipulator platform 2170 supports multiple manipulators 2176 for surgical instruments and an imaging system, described below.

These illustrative manipulator arm assemblies are used, for example, for instrument assemblies that include a rigid guide tube and are operated to move with reference to a remote center. Certain setup and active joints in the manipulator arm may be omitted if motion around a remote center is not required. It should be understood that manipulator arms may include various combinations of links, passive, and active joints (redundant DOFs may be provided) to achieve a necessary range of poses for surgery.

Referring again to FIG. 21A, video system 2106 performs image processing functions for, e.g., captured endoscopic imaging data of the surgical site and/or preoperative or real time image data from other imaging systems external to the patient. Imaging system 2106 outputs processed image data (e.g., images of the surgical site, as well as relevant control and patient information) to the surgeon at the surgeon's console 2102. In some aspects the processed image data is output to an optional external monitor visible to other operating room personnel or to one or more locations remote from the operating room (e.g., a surgeon at another location may monitor the video; live feed video may be used for training; etc.).

Figure 22A:
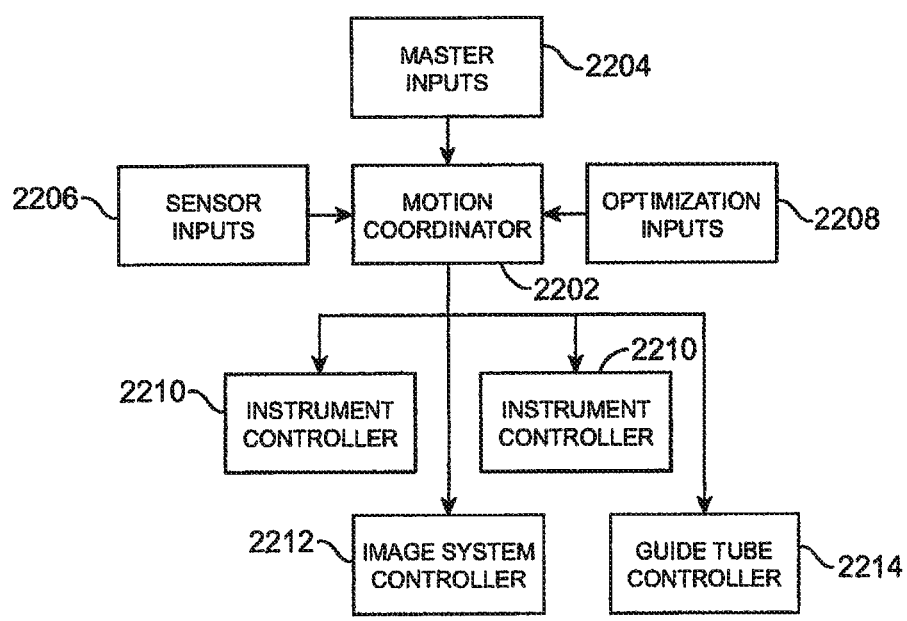
FIG. 22A is a diagrammatic view of a centralized motion control system for a minimally invasive telesurgical system.

FIG. 22A is a diagrammatic view that illustrates aspects of a centralized motion control and coordination system architecture for minimally invasive telesurgical systems that incorporate surgical instrument assemblies and components described herein. A motion coordinator system 2202 receives master inputs 2204, sensor inputs 2206, and optimization inputs 2208.

Master inputs 2204 may include the surgeon's arm, wrist, hand, and finger movements on the master control mechanisms. Inputs may also be from other movements (e.g., finger, foot, knee, etc. pressing or moving buttons, levers, switches, etc.) and commands (e.g., voice) that control the position and orientation of a particular component or that control a task-specific operation (e.g., energizing an electrocautery end effector or laser, imaging system operation, and the like).

Sensor inputs 2206 may include position information from, e.g., measured servomotor position or sensed bend information. U.S. patent application Ser. No. 11/491,384 (Larkin, et al.) entitled "Robotic surgery system including position sensors using fiber Bragg gratings", incorporated by reference, describes the use of fiber Bragg gratings for position sensing. Such bend sensors may be incorporated into the various instruments and imaging systems described herein to be used when determining position and orientation information for a component (e.g., an end effector tip). Position and orientation information may also be generated by one or more sensors (e.g., fluoroscopy, MRI, ultrasound, and the like) positioned outside of the patient, and which in real time sense changes in position and orientation of components inside the patient.

As described below, the user interface has three coupled control modes: a mode for the instrument (s), a mode for the imaging system, and a mode for the guide tube. These coupled modes enable the user to address the system as a whole rather than directly controlling a single portion. Therefore, the motion coordinator must determine how to take advantage of the overall system kinematics (i.e., the total DOFs of the system) in order to achieve certain goals. For example, one goal may be to optimize instrument workspace for a particular configuration. Another goal may be to keep the imaging system's field of view centered between two instruments. Therefore, optimization inputs 2208 may be high-level commands, or the inputs may include more detailed commands or sensory information. An example of a high level command would be a command to an intelligent controller to optimize a workspace. An example of a more detailed command would be for an imaging system to start or stop optimizing its camera. An example of a sensor input would be a signal that a workspace limit had been reached.

Motion coordinator 2202 outputs command signals to various actuator controllers and actuators (e.g., servomotors) associated with manipulators for the various telesurgical system arms. FIG. 22A depicts an example of output signals being sent to two instrument controllers 2210, to an imaging system controller 2212, and to a guide tube controller 2214. Other numbers and combinations of controllers may be used.

As an example, such a motion coordination system may be used to control surgical instrument assembly 1700 (FIG. 17). Instrument controllers 2210 are associated with instruments 1702a,1702b, imaging system controller 2212 is associated with imaging system 1704, and guide tube controller 2214 is associated with guide tube 1708. Accordingly, in some aspects the surgeon who operates the telesurgical system will simultaneously and automatically access at least the three control modes identified above: an instrument control mode for moving the instruments, an imaging system control mode for moving the imaging system, and a guide tube control mode for moving the guide tube. A similar centralized architecture may be adapted to work with the various other mechanism aspects described herein.

Figure 22B:
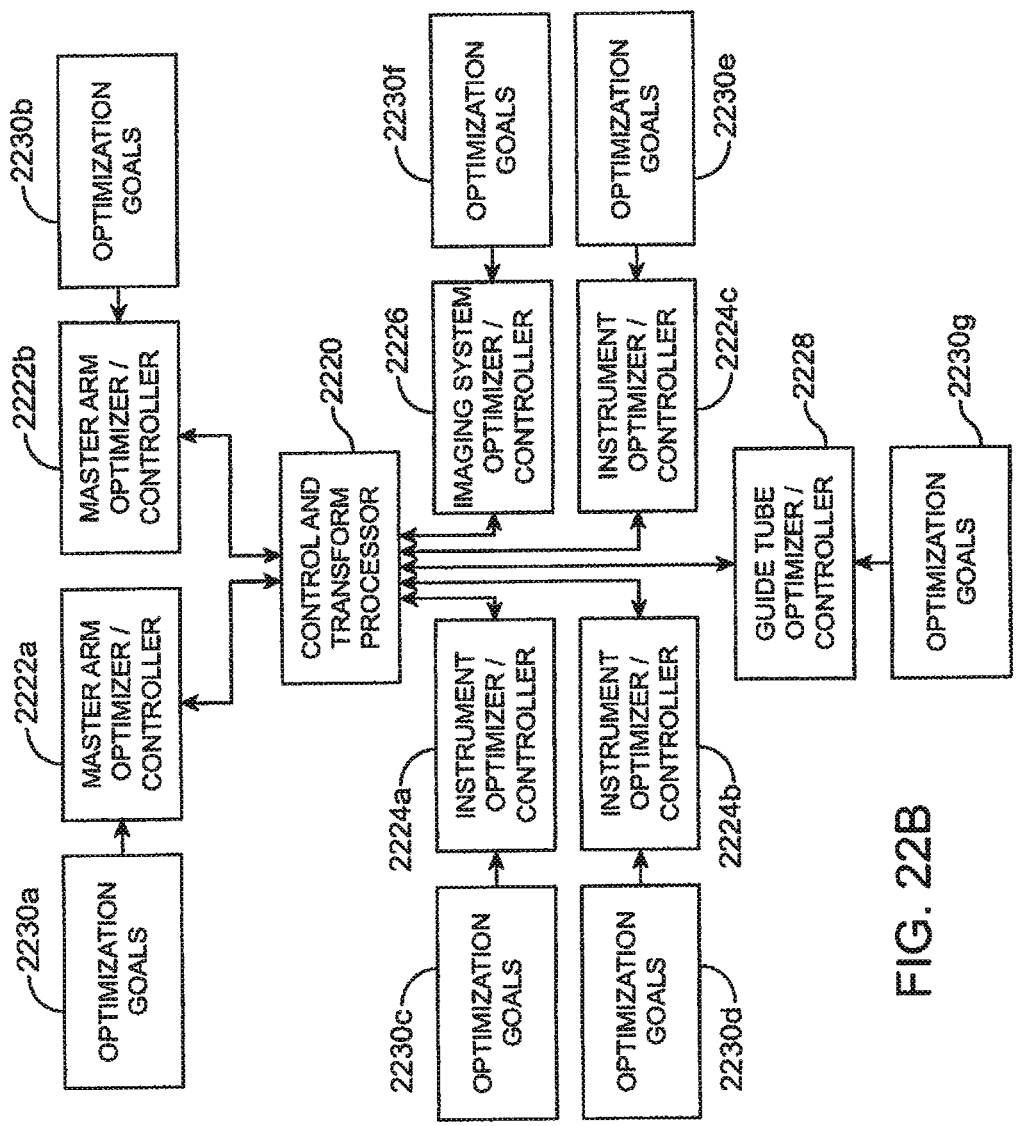
FIG. 22B is a diagrammatic view of a distributed motion control system for a minimally invasive telesurgical system.

FIG. 22B is a diagrammatic view that illustrates aspects of a distributed motion control and coordination system architecture for minimally invasive telesurgical systems that incorporate surgical instrument assemblies and components described herein. In the illustrative aspects shown in FIG. 22B, control and transform processor 2220 exchanges information with two master arm optimizer/controllers 2222a, 2222b, with three surgical instrument optimizer/controllers 2224a,2224b,2224c, with an imaging system optimizer/controller 2226, and with a guide tube optimizer/controller 2228. Each optimizer/controller is associated with a master or slave arm (which includes, e.g., the camera (imaging system) arm, the guide tube arm, and the instrument arms) in the telesurgical system. Each of the optimizer/controllers receives arm-specific optimization goals 2230a-2230g.

The double-headed arrows between control and transform processor 2220 and the various optimizer/controllers represents the exchange of Following Data associated with the optimizer/controller's arm. Following Data includes the full Cartesian configuration of the entire arm, including base frame and distal tip frame. Control and transform processor 2220 routes the Following Data received from each optimizer/controller to all the optimizer/controllers so that each optimizer/controller has data about the current Cartesian configuration of all arms in the system. In addition, the optimizer/controller for each arm receives optimization goals that are unique for the arm. Each arm's optimizer/controller then uses the other arm positions as inputs and constraints as it pursues its optimization goals. In one aspect, each optimization controller uses an embedded local optimizer to pursue its optimization goals. The optimization module for each arm's optimizer/controller can be independently turned on or off. For example, the optimization module for only the imaging system and the guide tube may be turned on.

The distributed control architecture provides more flexibility than the centralized architecture, although with the potential for decreased performance. It easier to add in a new arm and to change the overall system configuration if such a distributed control architecture is used rather than if a centralized architecture is used. In this distributed architecture, however, the optimization is local versus the global optimization that can be performed with the centralized architecture, in which a single module is aware of the full system's state.

Figure 23:
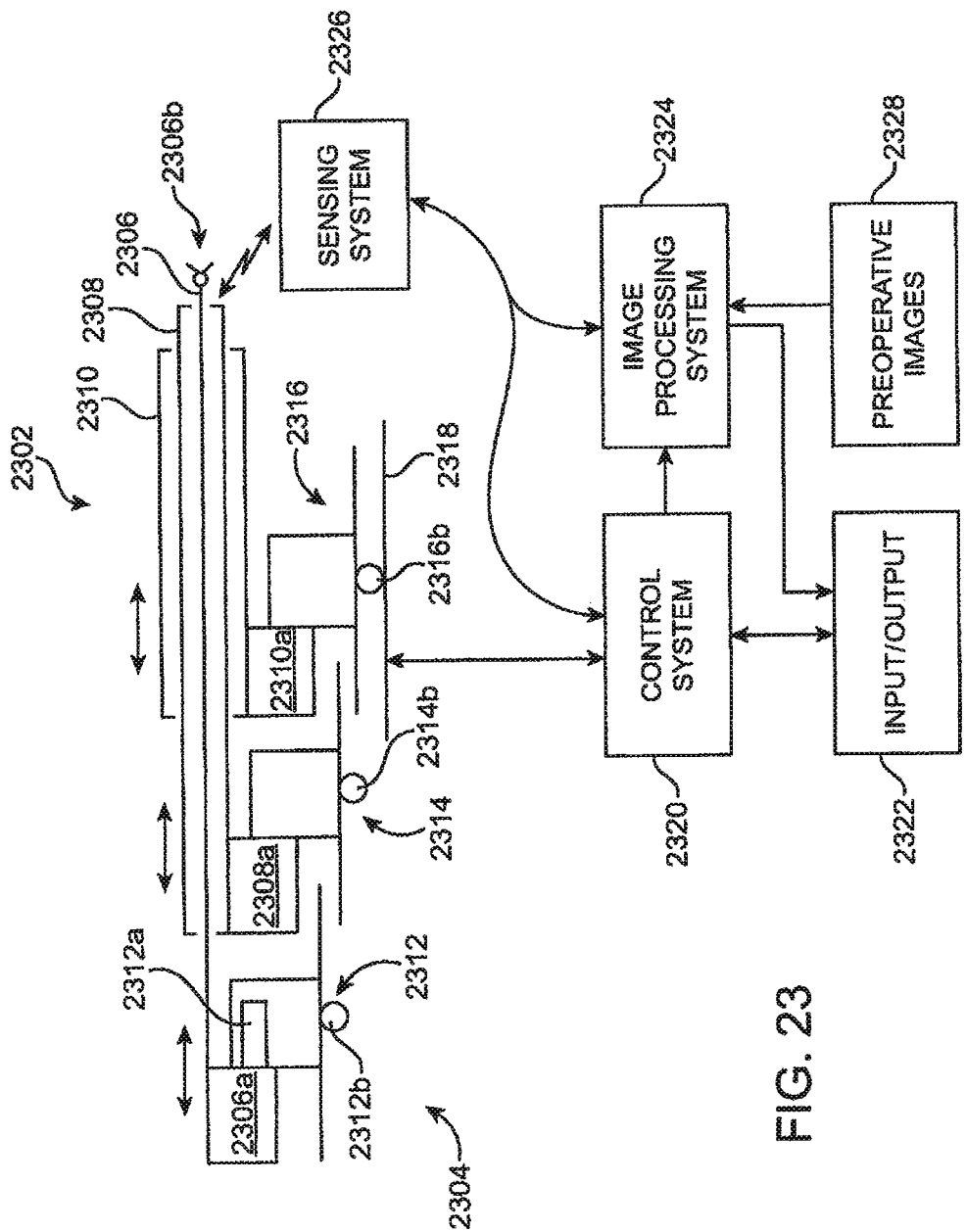
FIG. 23 is a schematic view of an interface between a surgical instrument assembly and an actuator assembly.

FIG. 23 is a schematic view that illustrates aspects of an interface between surgical instrument assembly 2302, which represents flexible and rigid mechanisms as variously described herein, and an illustrative actuator assembly 2304. For the purposes of this example, instrument assembly 2302 includes surgical instrument 2306, primary guide tube 2308 that surrounds instrument 2306, and secondary guide tube 2310 that surrounds primary guide tube 2308.

As shown in FIG. 23, a transmission mechanism is positioned at the proximal ends of each instrument or guide tube: transmission mechanism 2306a for instrument 2306, transmission mechanism 2308a for primary guide tube 2308, and transmission mechanism 2310a for secondary guide tube 2310. Each transmission mechanism is mechanically and removably coupled to an associated actuator mechanism: transmission mechanism 2306a to actuator mechanism 2312, transmission mechanism 2308a to actuator mechanism 2314, transmission mechanism 2310a to actuator mechanism 2316. In one aspect, mating disks are used as in the da Vinci® Surgical System instrument interface, as shown in more detail below. In another aspect, mating gimbal plates and levers are used. Various mechanical components (e.g., gears, levers, cables, pulleys, cable guides, gimbals, etc.) in the transmission mechanisms are used to transfer the mechanical force from the interface to the controlled element. Each actuator mechanism includes at least one actuator (e.g., servomotor (brushed or brushless)) that controls movement at the distal end of the associated instrument or guide tube. For example, actuator 2312a is an electric servomotor that controls surgical instrument 2306's end effector 2306b grip DOF. An instrument (including a guide probe as described herein) or guide tube (or, collectively, the instrument assembly) may be decoupled from the associated actuator mechanism(s) and slid out as shown. It may then be replaced by another instrument or guide tube. In addition to the mechanical interface there is an electronic interface between each transmission mechanism and actuator mechanism. This electronic interface allows data (e.g., instrument/guide tube type) to be transferred.

In some instances one or more DOFs may be manually actuated. For instance, surgical instrument 2306 may be a passively flexible laparoscopic instrument with a hand-actuated end effector grip DOF, and guide tube 2308 may be actively steerable to provide wrist motion as described above. In this example, the surgeon servocontrols the guide tube DOFs and an assistant hand controls the instrument grip DOF.

In addition to the actuators that control the instrument and/or guide tube elements, each actuator assembly may also include an actuator component (e.g., motor-driven cable, lead screw, pinion gear, etc.; linear motor; and the like) that provides motion along instrument assembly 2302's longitudinal axis (surge). As shown in the FIG. 23 example, actuator mechanism 2312 includes linear actuator 2312b, actuator mechanism 2314 includes linear actuator 2314b, and actuator mechanism 2316 includes linear actuator 2316b, so that instrument 2306, primary guide tube 2308, and secondary guide tube 2310 can each be independently coaxially moved. As further shown in FIG. 23, actuator assembly 2316 is mounted to setup arm 2318, either passively or actively as described above. In active mounting architectures, the active mounting may be used to control one or more component DOFs (e.g., insertion of a rigid guide tube).

Control signals from control system 2320 control the various servomotor actuators in actuator assembly 2304. The control signals are, e.g., associated with the surgeon's master inputs at input/output system 2322 to move instrument assembly 2302's mechanical slave components. In turn, various feedback signals from sensors in actuator assembly 2304, and/or instrument assembly 2302, and/or other components are passed to control system 2320. Such feedback signals may be pose information, as indicated by servomotor position or other position, orientation, and force information, such as may be obtained with the use of fiber Bragg grating-based sensors. Feedback signals may also include force sensing information, such as tissue reactive forces, to be, e.g., visually or haptically output to the surgeon at input/output system 2322.

Image data from an endoscopic imaging system associated with instrument assembly 2302 are passed to image processing system 2324. Such image data may include, e.g., stereoscopic image data to be processed and output to the surgeon via input/output system 2322 as shown. Image processing may also be used to determine instrument position, which is input to the control system as a form of distal position feedback sensor. In addition, an optional sensing system 2326 positioned outside and near the patient may sense position or other data associated with instrument assembly 2302. Sensing system 2326 may be static or may be controlled by control system 2320 (the actuators are not shown, and may be similar to those depicted or to known mechanical servo components), and it may include one or more actual sensors positioned near the patient. Position information (e.g., from one or more wireless transmitters, RFID chips, etc.) and other data from sensing system 2326 may be routed to control system 2320. If such position information or other data is to be visually output to the surgeon, control system 2320 passes it in either raw or processed form to image processing system 2324 for integration with the surgeon's output display at input/output system 2322. Further, any image data, such as fluoroscopic or other real-time imaging (ultrasound, X-ray, MRI, and the like), from sensing system 2326 are sent to image processing system 2324 for integration with the surgeon's display. And, real-time images from sensing system 2326 may be integrated with preoperative images accessed by image processing system 2324 for integration with the surgeon's display. In this way, for instance, preoperative images of certain tissue (e.g., brain tissue structures) are received from a data storage location 2328, may be enhanced for better visibility, the preoperative images are registered with other tissue landmarks in real time images, and the combined preoperative and real time images are used along with position information from instrument and actuator assemblies 2302, 2304 and/or sensing system 2326 to present an output display that assists the surgeon to maneuver instrument assembly 2302 towards a surgical site without damaging intermediate tissue structures.

Figure 24A:
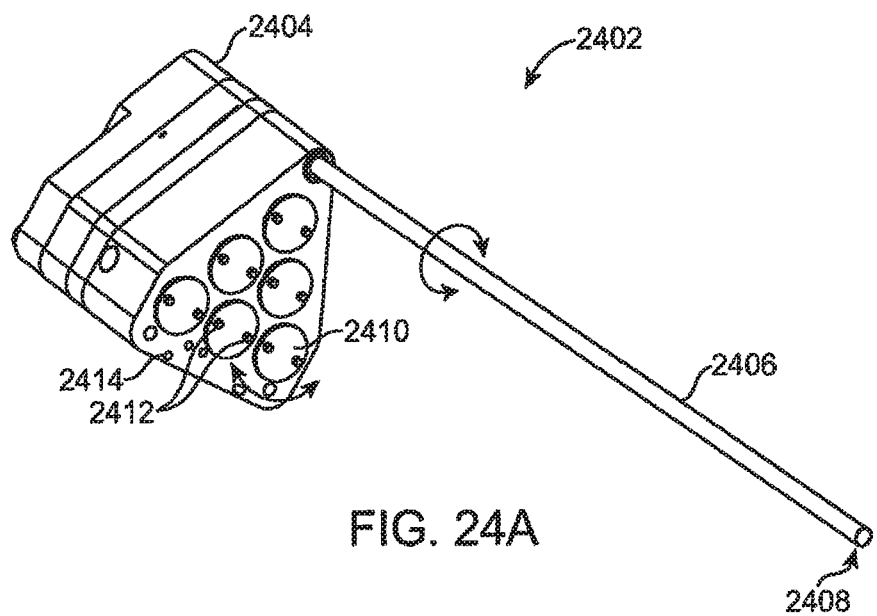
FIG. 24A is a perspective view of the proximal segment of a minimally invasive surgical instrument.

FIG. 24A is a perspective view of the proximal portion of a minimally invasive surgical instrument 2402. As shown in FIG. 24A, instrument 2402 includes a transmission mechanism 2404 coupled to the proximal end of an instrument body tube 2406. Components at body tube 2406's distal end 2408 are omitted for clarity and may include, e.g., the 2 DOF parallel motion mechanism, wrist, and end effector combination as described above; joints and an endoscopic imaging system as described above; etc. In the illustrative embodiment shown, transmission mechanism 2404 includes six interface disks 2410. One or more disks 2410 are associated with a DOF for instrument 240. For instance, one disk may be associated with instrument body roll DOF, and a second disk may be associated with end effector grip DOF. As shown, in one instance the disks are arranged in a hexagonal lattice for compactness—in this case six disks in a triangular shape. Other lattice patterns or more arbitrary arrangements may be used. Mechanical components (e.g., gears, levers, gimbals, cables, etc.) inside transmission mechanism 2404 transmit roll torques on disks 2410 to e.g., body tube 2406 (for roll) and to components coupled to distal end mechanisms. Cables and/or cable and hypotube combinations that control distal end DOFs run through body tube 2406. In one instance the body tube is approximately 7 mm in diameter, and in another instance it is approximately 5 mm in diameter. Raised pins 2412, spaced eccentrically, provide proper disk 2410 orientation when mated with an associated actuator disk. One or more electronic interface connectors 2414 provide an electronic interface between instrument 2402 and its associated actuator mechanism. In some instances instrument 2402 may pass information stored in a semiconductor memory integrated circuit to the control system via its associated actuator mechanism. Such passed information may include instrument type identification, number of instrument uses, and the like. In some instances the control system may update the stored information (e.g., to record number of uses to determine routine maintenance scheduling or to prevent using an instrument after a prescribed number of times). U.S. Pat. No. 6,866,671 (Tierney et al.), which discusses storing information on instruments, is incorporated by reference. The electronic interface may also include power for, e.g., an electrocautery end effector. Alternately, such a power connection may be positioned elsewhere on instrument 2402 (e.g., on transmission mechanism 2404's housing). Other connectors for, e.g., optical fiber lasers, optical fiber distal bend or force sensors, irrigation, suction, etc. may be included. As shown, transmission mechanism 2404's housing is roughly wedge- or pie-shaped to allow it to be closely positioned to similar housings, as illustrated below.

Figure 24B:
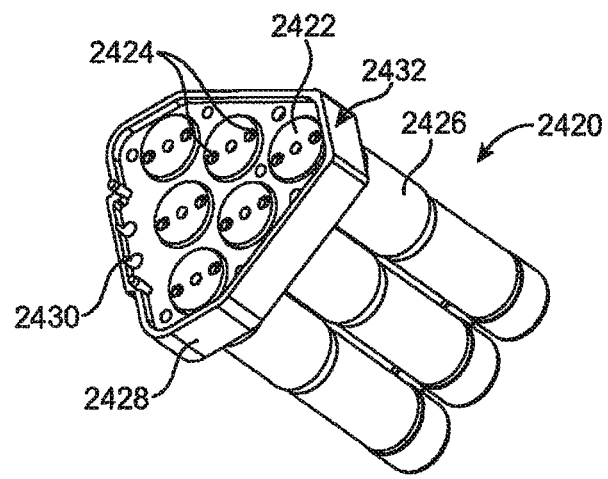
FIG. 24B is a perspective view of a segment of an actuator assembly 2420 that mates with and actuates the instrument shown in FIG. 24A.

FIG. 24B is a perspective view of a portion of an actuator assembly 2420 that mates with and actuates components in surgical instrument 2402. Actuator disks 2422 are arranged to mate with interface disks 2410. Holes 2424 in disks 2422 are aligned to receive pins 2412 in only a single 360-degree orientation. Each disk 2422 is turned by an associated rotating servomotor actuator 2426, which receives servo-control inputs as described above. A roughly wedge-shaped mounting bracket 2428, shaped to correspond to instrument 2402's transmission mechanism housing, supports the disks 2422, servomotor actuators 2426, and an electronic interface 2430 that mates with instrument 2402's interface connectors 2414. In one instance instrument 2402 is held against actuator assembly 2420 by spring clips (not shown) to allow easy removal. As shown in FIG. 24B, a portion 2432 of actuator assembly housing 2428 is truncated to allow instrument body tube 2406 to pass by. Alternatively, a hole may be placed in the actuator assembly to allow the body tube to pass through. Sterilized spacers (reusable or disposable; usually plastic) may be used to separate the actuator assembly and the instrument's transmission mechanism to maintain a sterile surgical field. A sterile thin plastic sheet or "drape" (e.g., 0.002-inch thick polyethylene) is used to cover portions of the actuator assembly not covered by the spacer, as well as to cover portions of the manipulator arm. U.S. Pat. No. 6,866,671, incorporated by reference above, discusses such spacers and drapes.

Figure 25A:
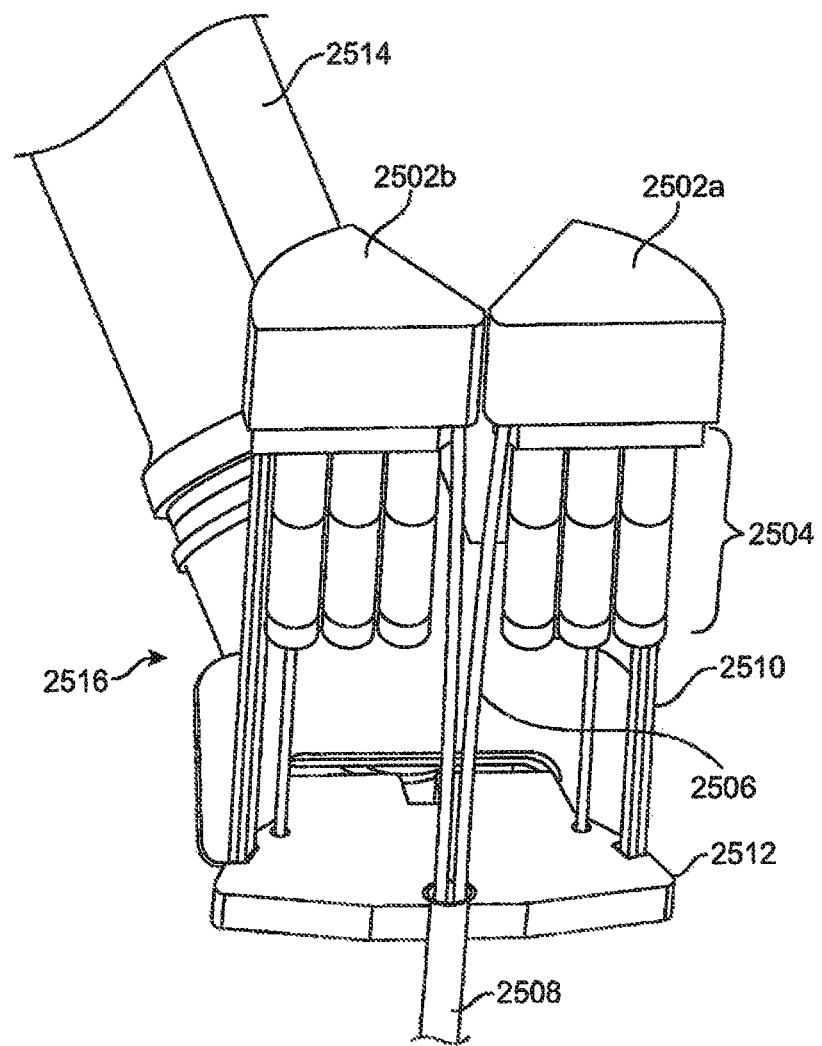
FIG. 25A is a diagrammatic perspective view that illustrates mounting minimally invasive surgical instruments and actuator assemblies at the end of a setup arm.

FIG. 25A is a diagrammatic perspective view that illustrates aspects of mounting minimally invasive surgical instruments and their associated actuator assemblies at the end of a setup/manipulator arm. As shown in FIG. 25A, surgical instrument 2502a is mounted on actuator assembly 2504, so that the transmission mechanism mates with the actuator assembly (optional spacer/drape is not shown) as described above. Instrument 2502a's body tube 2506 extends past actuator assembly 2504 and enters a port in rigid guide tube 2508. As depicted, body tube 2506, although substantially rigid, is bent slightly between the transmission mechanism housing and the guide tube as discussed above with reference to FIG. 16. This bending allows the instrument body tube bores in the entry guide to be spaced closer than the size of their transmission mechanisms would otherwise allow. Since the bend angle in the rigid instrument body tube is less than the bend angle for a flexible (e.g., flaccid) instrument body, cables can be stiffer than in a flexible body. High cable stiffness is important because of the number of distal DOFs being controlled in the instrument. Also, the rigid instrument body is easier to insert into a guide tube than a flexible body. In one embodiment the bending is resilient so that the body tube assumes its straight shape when the instrument is withdrawn from the guide tube (the body tube may be formed with a permanent bend, which would prevent instrument body roll). Actuator assembly 2504 is mounted to a linear actuator 2510 (e.g. a servocontrolled lead screw and nut or a ball screw and nut assembly) that controls body tube 2506's insertion within guide tube 2508. The second instrument 2502b is mounted with similar mechanisms as shown. In addition, an imaging system (not shown) may be similarly mounted.

FIG. 25A further shows that guide tube 2508 is removably mounted to support platform 2512. This mounting may be, for example, similar to the mounting used to hold a cannula on a da Vinci® Surgical System manipulator arm. Removable and replaceable guide tubes allow different guide tubes that are designed for use with different procedures to be used with the same telemanipulative system (e.g., guide tubes with different cross-sectional shapes or various numbers and shapes of working and auxiliary channels). In turn, actuator platform 2512 is mounted to robot manipulator arm 2514 (e.g., 4 DOF) using one or more additional actuator mechanisms (e.g., for pitch, yaw, roll, insertion). In turn, manipulator arm 2514 may be mounted to a passive setup arm, as described above with reference to FIG. 21A.

Figure 25B:
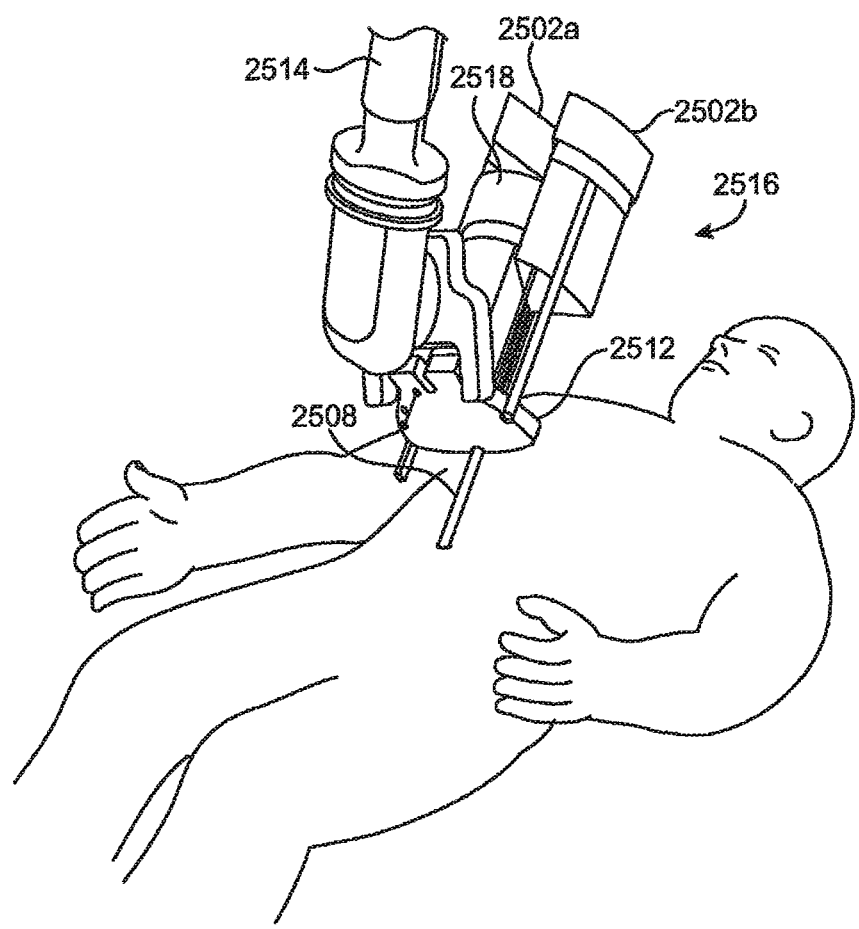
FIG. 25B is another diagrammatic perspective view that illustrates mounting minimally invasive surgical instruments and actuator assemblies at the end of a setup arm.

FIG. 25B is a diagrammatic perspective view that illustrates aspects shown in FIG. 25A from a different angle and with reference to a patient. In FIG. 25B, arm 2514 and platform 2512 are positioned so that guide tube 2508 enters the patient's abdomen at the umbilicus. This entry is illustrative of various natural orifice and incision entries, including percutaneous and transluminal (e.g., transgastric, transcolonic, transrectal, transvaginal, transrectouterine (Douglas pouch), etc.) incisions. FIG. 25B also illustrates how the linear actuators for each instrument/imaging system operate independently by showing imaging system 2518 inserted and instruments 2502a, 2502b withdrawn. These aspects may apply to other surgical instrument assemblies described herein (e.g., flexible guide tubes with end- or side-exit ports, side working tools, etc.). It can be seen that in some instances the manipulator arm moves to rotate guide tube 2508 around a remote center 2520 at the entry port into a patient. If intermediate tissue restricts movement around a remote center, however, the arm can maintain guide tube 2508 in position.

Figure 26A:
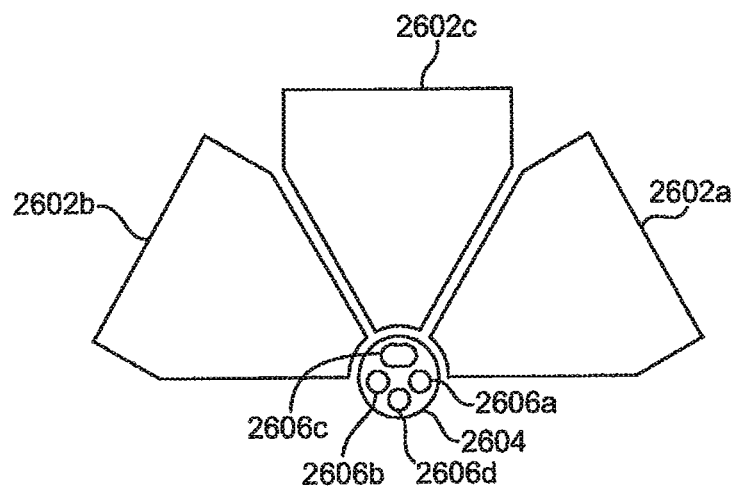
FIG. 26A is a diagrammatic end view of instrument transmission mechanisms and a guide tube.
Figure 26B:
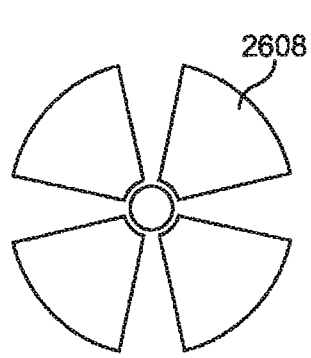
FIGS. 26B, 26C, and 26D are diagrammatic end views of transmission mechanisms spaced around a guide tube.
Figure 26C:
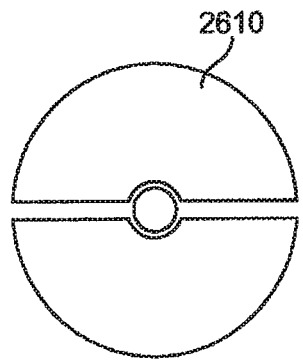
Figure 26D:
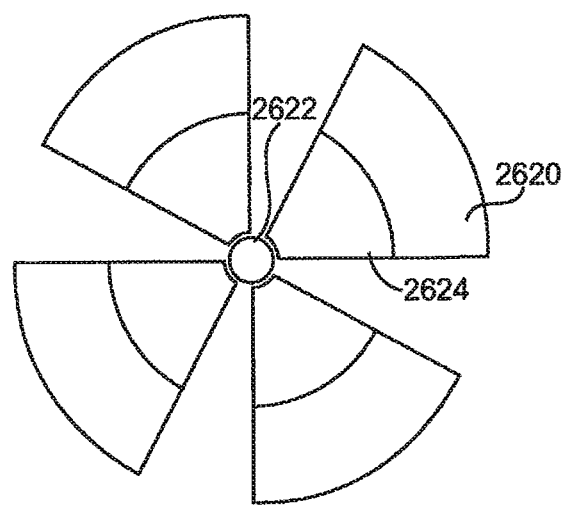

As discussed above, in one aspect the instruments and their transmission mechanisms are arranged around a guide tube in a generally pie-wedge layout as shown in FIG. 26A, which is a diagrammatic end view of instrument transmission mechanisms and a guide tube (the vertices of the wedge shapes are oriented towards an extended centerline of the guide tube). The vertices of the wedge shapes are shown slightly truncated; the wedge shape should be understood to be broadly construed and to include both acute and obtuse vertex angles. Instrument transmission mechanisms 2602a, 2602b transfer control forces from servomotors to instruments inserted via guide tube 2604's working channels 2606a, 2606b. Imaging system transmission mechanism 2608 transfers control forces from servomotors to the multi-DOF imaging system instrument inserted via guide tube 2604's imaging system channel 2606c. One or more optional guide tube channels 2604d allow for manually inserting an instrument, irrigation, suction, etc. FIGS. 26B and 26C are similar diagrammatic end views and illustrate that transmission mechanisms may be spaced around the guide tube in other configurations, such as four wedges 2608 spaced 360-degrees around the guide tube (FIG. 26B), or two half-circle shaped housings 2610 (FIG. 26C). It can also be seen from the aspects illustrated in FIGS. 25A, 25B, 26A, 26B, and 26C that transmission assemblies can not only be spaced around the guide tube but can be stacked one above or behind the other as FIG. 23 schematically illustrates. FIG. 26D is another diagrammatic end view that illustrates that actuator mechanisms 2620 may be placed farther from guide tube 2622's extended centerline than the instrument/guide tube and imaging system transmission mechanisms 2624.

Figure 26E:
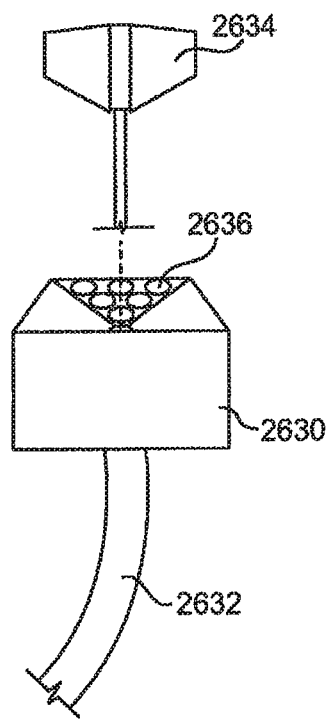
FIG. 26E is a diagrammatic exploded perspective view of an actuator housing and an instrument.

FIG. 26E is a diagrammatic exploded perspective view that illustrates that actuator mechanisms for more than one component may be placed in a single housing. As shown in FIG. 26E, actuator mechanism housing 2630 includes servomotors and associated components (not shown) used to move guide tube 2632. Housing 2630 also includes servomotors and associated components used to operate instrument 2634. Instrument 2634's body and distal segments are inserted through housing 2630 as shown, and interface components 2636 on housing 2630 connect with corresponding components (e.g., disks 2410 (FIG. 24)) on instrument 2634. Such an arrangement may be used for, e.g., the side exit surgical instrument assemblies described herein, in which there are two housings 2634, each associated with one of the side exiting instruments or guide tubes.

Details about the mechanical and electrical interfaces for the various instruments, guide tubes, and imaging systems, and also about sterile draping to preserve the sterile field, are discussed in U.S. Pat. No. 6,866,671 (Tierney et al.) and U.S. Pat. No. 6,132,368 (Cooper), both of which are incorporated by reference. Mechanical interface mechanisms are not limited to the disks shown and described. Other mechanisms such as rocking plates, gimbals, moving pins, levers, cable latches, and other removable couplings may be used.

FIG. 27 is a diagrammatic view that illustrates aspects of transmission mechanisms associated with flexible coaxial guide tubes and instruments. FIG. 27 shows primary guide tube 2702 running coaxially through and exiting the distal end of secondary guide tube 2704. Likewise, secondary guide tube 2704 runs coaxially through and exits the distal end of tertiary guide tube 2706. Transmission and actuator mechanism 2708 is associated with tertiary guide tube 2706. Transmission and actuator mechanism 2710 is associated with secondary guide tube 2704, and a proximal segment of guide tube 2704 extends through (alternatively, adjacent to) transmission and actuator mechanism 2710 before entering tertiary guide tube 2706. Likewise, transmission and actuator mechanism 2712 is associated with primary guide tube 2702, and a proximal segment of guide tube 2702 extends through (alternatively, adjacent to) transmission and actuator mechanisms 2708,2710 before entering secondary and tertiary guide tubes 2704,2706. Transmission mechanisms for instruments and an imaging system (not shown) running through and exiting the distal ends of channels 2714 in primary guide tube 2702 may be similarly stacked generally along the instrument assembly's longitudinal axis, or they may be arranged around guide tube 2702's extended longitudinal axis at its proximal end as described above. Or, the controller positions may be combined side-by-side and stacked, such as for a side-exit assembly in which transmission mechanisms for the side-exiting components are positioned side-by-side, and both are stacked behind the guide tube transmission mechanism. Intermediate exit assemblies may be similarly configured. Instrument and/or imaging system actuators and controls may also be combined within the same housing as an actuator and transmission mechanism for a guide tube.

In many aspects the devices described herein are used as single-port devices—all components necessary to complete a surgical procedure enter the body via a single entry port. In some aspects, however, multiple devices and ports may be used. FIG. 28A is a diagrammatic view that illustrates multi-port aspects as three surgical instrument assemblies enter the body at three different ports. Instrument assembly 2802 includes a primary guide tube, a secondary guide tube, and two instruments, along with associated transmission and actuator mechanisms, as described above. In this illustrative example, instrument assembly 2804 includes a primary guide tube, a secondary guide tube, and a single instrument, along with associated transmission and actuator mechanisms, as described above. Imaging system assembly 2806 includes a guide tube and an imaging system, along with associated transmission and actuator mechanisms, as described above. Each of these mechanisms 2802,2804,2806 enters the body 2808 via a separate, unique port as shown. The devices shown are illustrative of the various rigid and flexible aspects described herein.

FIG. 28B is another diagrammatic view that illustrates multi-port aspects. FIG. 28B shows three illustrative instruments or assemblies 2810 entering different natural orifices (nostrils, mouth) and then continuing via a single body lumen (throat) to reach a surgical site.

Figure 29A:
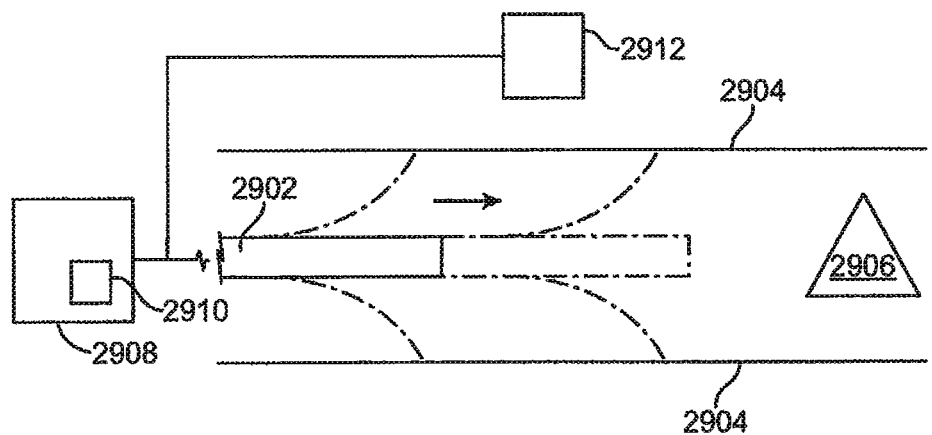
FIGS. 29A and 29B are diagrammatic views of minimally invasive surgical instrument assembly position sensing.
Figure 29B:
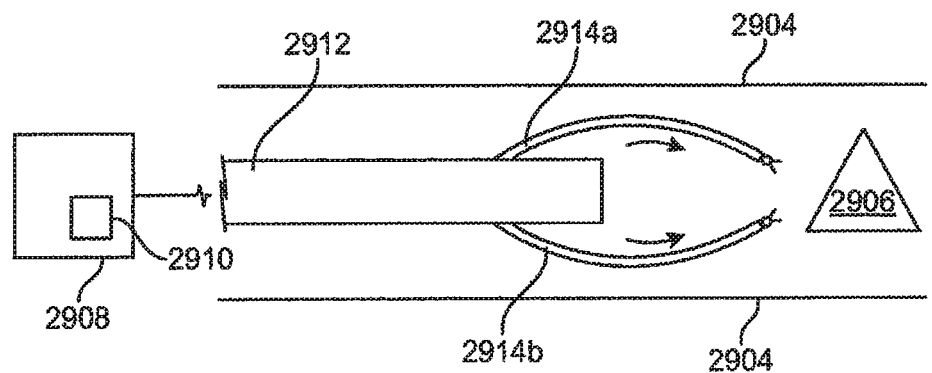

FIGS. 29A and 29B are diagrammatic views that illustrate further aspects of minimally invasive surgical instrument assembly position sensing and motion control. As shown in FIG. 29A, the distal end 2902 of a surgical instrument device or assembly is advanced within the walls 2904 of a body lumen or other cavity towards surgical site 2906. Distal end 2902 is illustrative of various components, such as a guide probe or guide tube as described above. As distal end 2902 advances it is moved (flexed as shown, or pivoted at a joint) up and down and side to side, as depicted by the alternate position lines. As the tip of distal end 2902 touches, or comes close to touching, a position on walls 2904, actuator control system 2908 records the tip's position and stores the position data in memory 2910. Tip position information may come directly from the surgical instrument assembly or from an external sensor 2912, as described above. The tip may be bent in various 3-dimensional directions so that it touches or nearly touches walls 2904 in various patterns (e.g., a series of rings, a helix, a series of various crosses or stars, etc.), either under a surgeon's direct control or under automatic control by control system 2908. Once the lumen's or cavity's interior space is mapped, the space information is used to assist advancing subsequent surgical instrument assembly components, as illustrated in FIG. 29B. As an example, a secondary guide tube 2912 with side exit ports is shown, and control system 2908 uses the map information to prevent primary guide tubes 2914a,2914b and their associated end effectors from interfering with walls 2904 as they are advanced towards surgical site 2906.

Figure 29C:
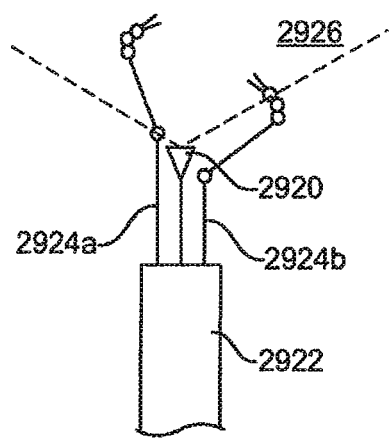
FIGS. 29C-29E are diagrammatic plan views that illustrate further aspects of preventing undesired instrument collision with tissue.
Figure 29D:
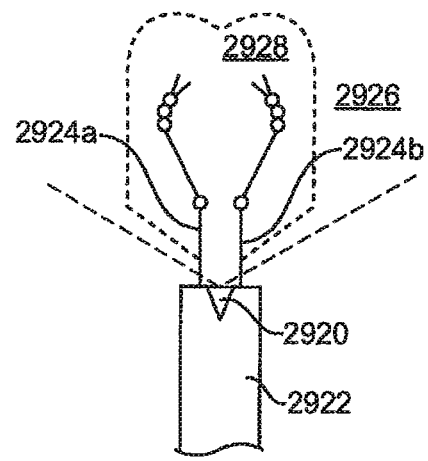
Figure 29E:
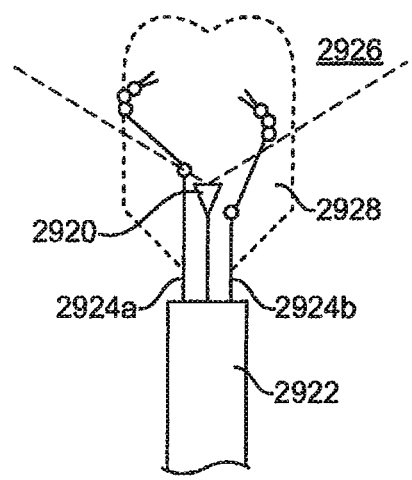

FIGS. 29C-29E are diagrammatic plan views that illustrate further aspects of preventing undesired instrument collision with tissue. Instruments may collide with patient tissue outside of an imaging system's field of view in spaces confined by patient anatomy (e.g., laryngeal surgery). Such collisions may damage tissue. For multi-DOF surgical instruments, some DOFs may be inside the field of view while other, more proximal DOFs may be outside the field of view. Consequently, a surgeon may be unaware that tissue damage is occurring as these proximal DOFs move. As shown in FIG. 29C, for example, an endoscopic imaging system 2920 extends from the end of guide tube 2922. The left side working instrument 2924a is placed so that all DOFs are within imaging system 2920's field of view 2926 (bounded by the dashed lines). The right side working instrument 2924b, however, has proximal DOFs (an illustrative parallel motion mechanism as described above and wrist are shown) that are outside field of view 2926, even though instrument 2924b's end effector is within field of view 2926. This instrument position is illustrative of tasks such as tying sutures.

In one aspect, field of view boundaries can be determined when the camera is manufactured so that the boundaries are known in relation to the camera head (image capture component). The boundary information is then stored in a nonvolatile memory associated with the imaging system that incorporates the camera head. Consequently, the control system can use the imaging system instrument's kinematic and joint position information to locate the camera head relative to the working instruments, and therefore the control system can determine the field of view boundaries relative to the working instruments. Instruments are then controlled to work within the boundaries.

In another aspect for stereoscopic imaging systems, field of view boundaries can be determined relative to the instruments by using machine vision algorithms to identify the instruments and their positions in the field of view. This "tool tracking" subject is disclosed in U.S. Patent Application Publication No. US 2006/0258938 A1 (Hoffman et al.), which is incorporated by reference.

As shown in FIG. 29D, imaging system 2920 is placed so that the camera head is just at the distal end of guide tube 2922. Instruments 2924a and 2924b are extended from the distal end of the guide tube and within imaging system 2920's field of view. An "Allowable Volume" is defined to be coincident with the field of view boundaries. The control system prevents any part of instruments 2924a and 2924b from moving outside the Allowable Volume. Since the surgeon can see all distal moving parts of instruments 2924a and 2924b, the surgeon then moves the instruments without colliding with surrounding tissue. The instrument movements are recorded, and an "Instrument Volume" 2928 (bounded by the dotted lines), which is bounded by the farthest movements of the instruments, is determined. The Instrument Volume is a convex volume within which instruments may be moved without colliding with tissue.

Next, imaging system 2920 is inserted as shown in FIG. 29E. As a result, field of view 2926 is also inserted, and parts of instruments 2924a,2924b are outside of the inserted field of view 2926. A new Allowable Volume is determined to be the newly inserted field of view plus the previously determined Instrument Volume that is outside of the field of view. Therefore, the control system will allow the surgeon to move an instrument anywhere within the new Allowable Volume. The process may be repeated for further field of view insertions or for guide tube 2922 movements. This scheme allows a surgeon to define the allowable instrument range of motion in real time without requiring a tissue model. The surgeon is only required to trace the boundaries of the instrument range of motion inside the field of view, and the control system will record this information as the field of view is changed.

Figure 29F:
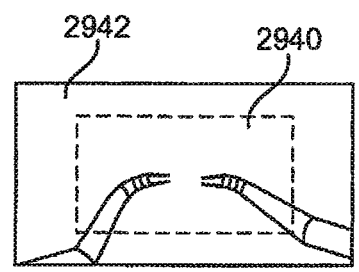
FIG. 29F is a diagrammatic view of an image mosaiced output display for a surgeon.

Another way to prevent unwanted instrument/tissue collision is by using image mosaicing. FIG. 29F is a diagrammatic view of a display (e.g., stereoscopic) that a surgeon sees during a surgical procedure. As shown in FIG. 29F, the image from the new, more inserted field of view 2940 (bounded by the dashed lines) is registered and mosaiced with the image from the old, more withdrawn field of view 2942. Image mosaicing is known (see e.g., U.S. Pat. No. 4,673,988 (Jansson et al.) and U.S. Pat. No. 5,999,662 (Burt et al.), which are incorporated by reference) and has been applied to medical equipment (see e.g., U.S. Pat. No. 7,194,118 (Harris et al.), which is incorporated by reference). As a result, the surgeon sees an area larger than the current, more inserted field of view. A kinematically accurate graphical simulation of the instruments is shown in the old field of view 2942 so that the surgeon can see possible collisions in this region as the instruments move.

Figure 30:
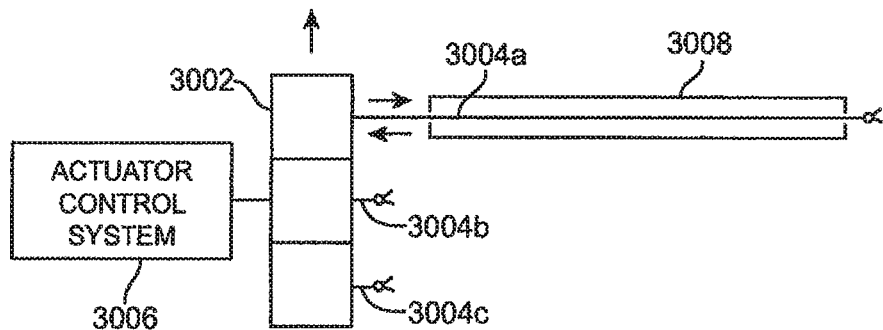
FIG. 30 is a schematic view of a mechanism for automatically exchanging minimally invasive surgical instruments.

In some aspects, minimally invasive surgical instrument assembly components may be replaced by hand during surgery. In other aspects, components may be automatically replaced. FIG. 30 is a schematic view that illustrates a mechanism for automatically exchanging minimally invasive surgical instruments (e.g., those of approximately 3 mm diameter, such as flexible laparoscopic instruments with a single grip DOF) during surgery. As shown in FIG. 30, an instrument magazine 3002 has several instruments 3004a, 3004b,3004c stored (e.g., three, as depicted). The instruments may be stored on a drum, linearly extended, or otherwise. In some aspects, the instruments in magazine 3002 are selected for each surgical procedure—that is, the surgeon determines the instruments to be used for a specific procedure, and magazine 3002 is configured accordingly. As FIG. 30 illustrates, magazine 3002 is positioned to allow actuator control system 3006 to advance instrument 3004a into guide tube 3008. To exchange an instrument, control system 3006 withdraws instrument 3004a from guide tube 3008 and repositions magazine 3002 to advance either instrument 3004b or 3004c into guide tube 3008. The magazine, instruments, and guide tube shown in FIG. 30 are illustrative of various components described herein (e.g., instruments, primary and secondary guide tubes, guide probes, imaging systems (optical, infrared, ultrasound), and the like).

Figure 30A:
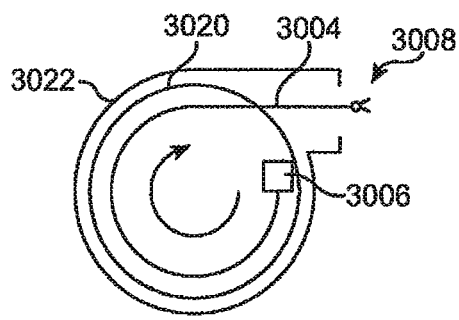
FIG. 30A is a schematic view of storing an instrument or other component on a drum.
Figure 30B:
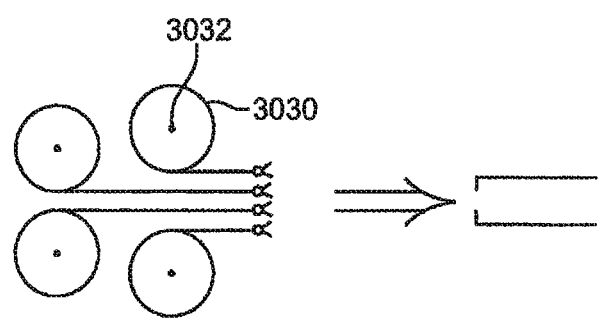
FIG. 30B is a schematic view of storing automatically replaceable instruments on spools.

FIG. 30A is a schematic view that illustrates aspects of storing an instrument or other component on a drum. Instrument 3004 is extended as drum 3020 rotates inside magazine housing 3022. Actuator 3006 for instrument 3004's end effector 3008 is positioned on drum 3020. Actuator 3006 is illustrative of other actuator assemblies that may be used if, for example, a steerable guide tube is to be advanced instead. Instrument 3004 is coiled loosely enough so that the cable actuator for end effector 3008 does not bind within its flexible cover. FIG. 30B is a schematic view that illustrates aspects of storing automatically replaceable instruments on spools 3030 mounted on individual capstans 3032.

Figure 31:
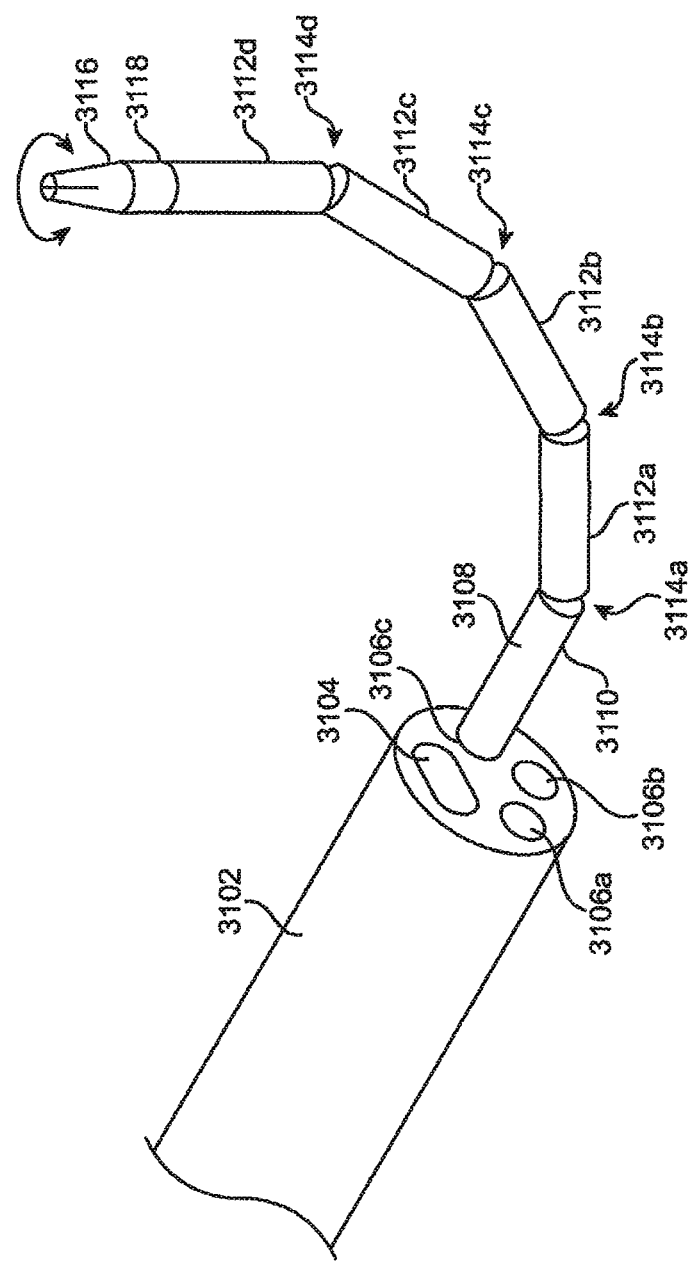
FIG. 31 is a diagrammatic perspective view of an illustrative minimally invasive surgical instrument assembly that includes a multi-jointed instrument dedicated to retraction.

FIG. 31 is a diagrammatic perspective view that shows aspects of an illustrative minimally invasive surgical instrument assembly that includes a multi-jointed instrument dedicated to retraction. As shown in FIG. 31, guide tube 3102 includes a channel 3104, through which an imaging system is inserted, and three channels 3106a,3106b,3106c, through which surgical instruments may be inserted. Retraction instrument 3108 is shown extending through channel 3106c.

As depicted, retraction instrument 3108 includes a proximal instrument body 3110 and four serial links 3112a-d. Four joints 3114a-d couple proximal instrument body 3110 and links 3112a-d together. In one aspect, each joint 3114a-d is an independently controllable single DOF pitch joint. In other aspects the joints may have additional DOFs. An actively controlled (either hand or telemanipulated) gripper 3116 is mounted at the distal end of the most distal link 3112d via a passive roll joint 3118. In some aspects other end effectors, or none, may be substituted for the gripper. In one aspect the combined length of links 3112a-d and gripper 3116 is sufficient to retract tissue beyond the working envelope of instruments that extend through channels 3106a and 3106b. For example, the combined lengths of the links and the gripper may be approximately equal to the full insertion range (e.g., approximately 5 inches) of the instruments. Four links and joints are shown, and other numbers of links and joints may be used. Retraction is done using various combinations of pitching joints 3114a-d and rolling instrument 3108 within channel 3106c.

For retraction, instrument 3108 is inserted so that each joint 3114a-d is exposed one after the other. Insertion depth may be varied so that retraction can begin at various distances from the distal end of the guide tube with various numbers of joints as the joints exit from the guide tube's distal end. That is, for example, retraction may begin as soon as joint 3114d is inserted past the distal end of the guide tube. For retraction, gripper 3116 may grip tissue. Passive roll joint 3118 prevents the gripped tissue from being torqued as instrument 3108 is rolled within channel 3106*c*. In one aspect, the control system couples the motions of instrument 3108 and guide tube 3102. This coupled control of motion allows tissue to be held in place by gripper 3116 as the guide tube is moved to the left or right "underneath" the retracted tissue. For example, as the distal end of guide tube 3102 is moved to the left, instrument 3108 is rolled (and joint 3114*a-d* pitch may be changed) to move gripper 3116 to the right.

FIG. 31 further illustrates an aspect of instrument position and control within guide tubes. The working surgical instruments need not be inserted though guide tube channels that correspond to or are aligned with their working position. For example, as shown in FIG. 31 the left side working instrument does not have to be inserted through the left-most channel 3106*c*. Instead, the left side working instrument may be inserted via the "bottom" channel 3106*b*. The right side working instrument may then be inserted via the right-most channel 3106*a*. Then, the left and right side working instruments may be controlled to work at a surgical site in alignment with the field of view of an imaging system inserted via channel 3104 that has not been rolled or yawed. Stated another way, the left-right axis between the working instruments' insertion channels does not have to be aligned with the left-right axis between the working instruments' end effectors at the surgical site or with the left-right axis interpupillary axis of the stereoscopic imaging system. Further, by the control system recognizing which instrument is coupled to each particular actuator, left-right instrument position may be varied. For example, retraction instrument 3108 may be inserted via channel 3106*a*, the right side working instrument may be inserted via channel 3106*b*, and the left side working instrument may be inserted via channel 3106*c*. In some aspects, with appropriately shaped channels and/or imaging systems, the imaging system may be inserted via one of several channels. For example, "top" channel 3104 and "bottom" channel 3106*b* may be oblong shaped with a center bore that holds a cylindrical instrument body, as shown in FIG. 20A. Consequently, an imaging system may be inserted via the "top" or "bottom" channel, and a working instrument may be inserted via the other "top" or "bottom" channel.

These descriptions of examples of various minimally invasive surgical systems, assemblies, and instruments, and of the associated components, are not to be taken as limiting. It should be understood that many variations that incorporate the aspects described herein are possible. For example, various combinations of rigid and flexible instruments and instrument components, and of guide tubes and guide tube components, fall within the scope of this description. The claims define the invention.

We claim:

1. A surgical instrument assembly comprising:
a guide tube comprising a proximal end, a distal end, and an intermediate position between the proximal and distal ends; and
a surgical instrument, wherein the surgical instrument is configured to pass through the guide tube, and wherein the surgical instrument is configured to exit the guide tube at the intermediate position;
wherein:
the surgical instrument comprises a parallel motion mechanism, the entire parallel motion mechanism of the surgical instrument being distal to the intermediate position in a first configuration; and
the parallel motion mechanism of the surgical instrument is configured to heave and sway a distal end of the parallel motion mechanism while preventing changing of a pitch or a yaw of the distal end of the parallel motion mechanism relative to a proximal end of the parallel motion mechanism.

2. The surgical instrument assembly of claim 1, wherein the surgical instrument comprises an end effector.

3. The surgical instrument assembly of claim 1, wherein the surgical instrument comprises an endoscopic image capture component.

4. The surgical instrument assembly of claim 1, wherein:
the surgical instrument comprises a first body segment;
the parallel motion mechanism comprises a first joint, a second joint, and a rigid second body segment;
the first joint, the second body segment, and the second joint being connected in series;
the first joint comprises a first hinge and a second hinge, the first and second hinges being configured to pivot around orthogonal axes, the first hinge being coupled to a distal end of the first body segment, the second hinge being connected directly to the first hinge, and the second hinge being coupled to the rigid second body segment; and
the second joint comprises a third hinge, the first hinge being connected to the third hinge so that if the first hinge moves in one of yaw or pitch in a first direction, the third hinge moves in the one of yaw or pitch in a second direction opposite to the first direction.

5. The surgical instrument assembly of claim 4, wherein the second joint further comprises a fourth hinge, the third and fourth hinges pivoting around orthogonal axes, wherein the second hinge is connected to the fourth hinge so that if the second hinge moves in an other of pitch or yaw in a third direction, the fourth hinge moves in the other of pitch or yaw in a fourth direction opposite to the third direction.

6. The surgical instrument assembly of claim 4, further comprising:
a wrist joint coupled to the second joint of the parallel motion mechanism; and
a distal end component coupled to the wrist joint.

7. The surgical instrument assembly of claim 6, further comprising a transmission mechanism positioned proximal to the first body segment, the transmission mechanism being configured to change a heave or a sway of the distal end component with reference to a longitudinal axis of the first body segment without changing pitch or yaw of the distal end component.

8. The surgical instrument assembly of claim 1, further comprising a stereoscopic image capture component positioned on the guide tube between the intermediate position and the distal end of the guide tube, wherein a field of view of the image capture component is generally perpendicular to a longitudinal axis of the guide tube near the image capture component.

9. The surgical instrument assembly of claim 1, wherein the guide tube comprises one or more channels extending from the proximal end of the guide tube to the distal end of the guide tube, the one or more channels being configured to allow one or more instruments to be passed through the distal end of the guide tube and extend beyond the distal end of the guide tube.

10. The surgical instrument assembly of claim 9, wherein a first channel of the one or more channels is configured to provide suction or irrigation.

11. The surgical instrument assembly of claim 9, wherein a first instrument of the one or more instruments comprises a second parallel motion mechanism, the entire second parallel motion mechanism being distal to the distal end of the guide tube in the first configuration.

\* \* \* \* \*